US012584121B2

(12) United States Patent
Wichelecki et al.

(10) Patent No.: US 12,584,121 B2
(45) Date of Patent: *Mar. 24, 2026

(54) ENZYMATIC PRODUCTION OF HEXOSES

(71) Applicant: BONUMOSE, INC., Charlottesville, VA (US)

(72) Inventors: Daniel Joseph Wichelecki, Charlottesville, VA (US); Edwin O. Rogers, Charlottesville, VA (US)

(73) Assignee: BONUMOSE, INC., Charlottesville, VA (US)

( * ) Notice: Subject to any disclaimer, the term of this patent is extended or adjusted under 35 U.S.C. 154(b) by 87 days.

This patent is subject to a terminal disclaimer.

(21) Appl. No.: 18/641,530

(22) Filed: Apr. 22, 2024

(65) Prior Publication Data

US 2024/0352440 A1 Oct. 24, 2024

Related U.S. Application Data

(60) Continuation of application No. 17/825,484, filed on May 26, 2022, now Pat. No. 11,993,796, which is a division of application No. 16/493,519, filed as application No. PCT/US2018/022185 on Mar. 13, 2018, now Pat. No. 11,345,909.

(60) Provisional application No. 62/470,620, filed on Mar. 13, 2017, provisional application No. 62/470,605, filed on Mar. 13, 2017, provisional application No. 62/480,798, filed on Apr. 3, 2017, provisional application No. 62/482,148, filed on Apr. 5, 2017.

(51) Int. Cl.

| | |
|---|---|
| *C12N 9/90* | (2006.01) |
| *C12N 9/10* | (2006.01) |
| *C12N 9/16* | (2006.01) |
| *C12N 9/92* | (2006.01) |
| *C12P 19/02* | (2006.01) |
| *C12P 19/14* | (2006.01) |
| *C12P 19/18* | (2006.01) |
| *C12P 19/24* | (2006.01) |

(52) U.S. Cl.
CPC ............. *C12N 9/90* (2013.01); *C12N 9/1051* (2013.01); *C12N 9/16* (2013.01); *C12N 9/92* (2013.01); *C12P 19/02* (2013.01); *C12P 19/14* (2013.01); *C12P 19/18* (2013.01); *C12P 19/24* (2013.01); *C12Y 204/01001* (2013.01); *C12Y 301/03011* (2013.01); *C12Y 503/01009* (2013.01); *C12Y 504/02002* (2013.01)

(58) Field of Classification Search
CPC ...................................................... C12N 9/90
See application file for complete search history.

(56) References Cited

U.S. PATENT DOCUMENTS

| | | | |
|---|---|---|---|
| 5,767,378 | A | 6/1998 | Bojsen et al. |
| 7,094,582 | B2 | 8/2006 | Bao et al. |
| 2002/0164588 | A1 | 11/2002 | Eisenberg et al. |
| 2003/0135870 | A1 | 7/2003 | Cheikh et al. |
| 2007/0009900 | A1 | 1/2007 | Doucette-Stamm et al. |
| 2007/0039069 | A1 | 2/2007 | Rogers et al. |
| 2012/0156746 | A1 | 6/2012 | Caimi et al. |
| 2012/0266329 | A1 | 10/2012 | Mathur et al. |
| 2016/0186162 | A1 | 6/2016 | Oh et al. |
| 2016/0186168 | A1 | 6/2016 | Konieczka et al. |
| 2016/0244769 | A1 | 8/2016 | Xia et al. |
| 2017/0016038 | A1 | 1/2017 | Maertens et al. |

FOREIGN PATENT DOCUMENTS

| | | |
|---|---|---|
| CN | 106399427 A | 2/2017 |
| JP | 11-266896 A | 10/1999 |
| JP | 2002-517256 A | 6/2002 |
| JP | 2014-239651 A | 12/2014 |
| WO | 02/077183 A2 | 10/2002 |
| WO | 2015/147644 A1 | 10/2015 |
| WO | 2016/201110 A1 | 12/2016 |
| WO | 2017/002978 A1 | 1/2017 |
| WO | 2018/129275 A1 | 7/2018 |
| WO | 2019/144944 A1 | 8/2019 |

OTHER PUBLICATIONS

Li et al., Biosynthesis of rare hexoses using microorganisms and related enzymes. Beilstein Journal of Organic Chemistry, Nov. 12, 2013, vol. 9, pp. 2434-2445.

Lim, Y-R. and Oh, D-K., Microbial metabolism and biotechnological production of D-allose. Applied Microbiology and Biotechnology, Jun. 8, 2011, vol. 91, No. 2, pp. 229-235.

Fushinobu et al., Nature, 2011, 478:538-542.

International Search Report and Written Opinion in International Application No. PCT/US2018/022185, dated Jun. 20, 2018.

Berrisford et al., "Crystal Structure of Pyrococcus furious Phosphoglucose Isomerase", Journal of Biological Chemistry, vol. 278, No. 35, 3003, pp. 33290-33297.

Tyrel Bryan "Criteria for Evolution of Successful Protein: Fold Fitness and Domain Dynamics Explored", Thesis, University of New Mexico, Sep. 12, 2014, pp. 1-99.

Chan et al., Biochemistry, 2008, vol. 47, No. 36, pp. 9608-9617.

Bruce M. Chassy and John Thompson "Regulation and Characterization of the Galactose-Phosphoenolpyruvate-Dependent Phosphotransferase System in Lactobacillus casei", J. Bacteriology, 1983, vol. 154, No. 3, pp. 1204-1214.

Fekete et al., "The alternative D-galactose degrading pathway of Aspergillus nidulans proceeds via L-sorbose", Arch. Microbiol., 2004, 181, pp. 35-44.

(Continued)

*Primary Examiner* — Suzanne M Noakes

(74) *Attorney, Agent, or Firm* — RAPHAEL BELLUM PLLC

(57) ABSTRACT

Disclosed herein are methods of producing hexoses from saccharides by enzymatic processes. The methods utilize fructose 6-phosphate and at least one enzymatic step to convert it to a hexose.

16 Claims, 20 Drawing Sheets

Specification includes a Sequence Listing.

(56)                    References Cited

OTHER PUBLICATIONS

Jung et al., "Crystal Structre and Substrate Specificity of D-Galactose-6-Phosphate Isomerase Complexed with Substrates", PLOS One, 2013, vol. 8, Issue 8, e72902, pp. 1-10.

Kano et al., "The rare sugar D-allose acts as a triggering molecule of rice deference via ROS generation", J. Experimental Botany, vol. 64, No. 16, 2013, pp. 4939-4951.

Kemp et al., "Microbial growth on C1 compounds, Incorporation of C1 units into allulose phosphate by extracts of Pseudomonas methanica", Biochem. J., 1966, 99, 41.

Ruijter et al., "Mannitol is Required for Stress Tolerance in Aspergillus niger Conidiospores", Eukaryotic Cell, 2003, vol. 2, No. 4, pp. 690-698.

Solopova et al., "A specific mutation in the promoter region of the silent cel cluster accounts for the appearance of lactose-utilizing lactococcus lactis MG1363", Applied and Environmental Microbiology, 2012, vol. 78, No. 16, pp. 5612-5621.

Van Rooijen et al., "Molecular Cloning, Characterization, and Nucleotide Sequence of the Tagatose 6-Phosphate Pathway Gene Cluster of the Lactose Operon of Lactococcus lactis", J. Biological Chem., vol. 266, No. 11, 1991, pp. 7176-7181.

Wichelecki et al. "ATP-binding cassette (ABC) transport system solute-binding protein-guided identification of novel d-altritol and galactitol catabolic pathways in Agrobacterium tumefaciens C58." Journal of Biological Chemistry 290.48 (2015): 28963-28976.

Zhang et al., The 2.2 A Resolution Structure of RpiB/AlsB from *Escherichia coli* Illustrates a New Approach to the Ribose-5-phosphate Isomerase Reaction, J Mol Biol. Oct. 3, 2003; 332(5): 1083-1094.

Roos et al. "D-ribose-5-phosphate isomerase B from *Escherichia coli* is also a functional D-allose-6-phosphate isomerase, while the *Mycobacterium tuberculosis* enzyme is not." Journal of molecular biology 382.3 (2008): 667-679.

Simier et al., Characteristics of the Mannitol Pathway in a Root Hemiparasitic Species, *Thesium humile* Vahl (Santalaceae), J. Plant Physiol. vol. 143, pp. 33-38 (1994).

Moradian et al. "A biomimetic biotechnological process for converting starch to fructose: thermodynamic and evolutionary considerations in applied enzymology", Journal of the American Chemical Society, Aug. 1992, pp. 6980-6987, 114(18).

Huang et al. "Panoramic view of a superfamily of phosphatases through substrate profiling", Proceedings of the National Academy of Sciences, Apr. 2015, 112(16).

Fructose 6-phosphate

PGI

Psicose 6-phosphate

P6PE

Allose 6-phosphate

A6PI

A6PP

Allose

Starch

IA or PA

Amylodextrin

P$_i$    αGP    Maltose

Glucose 1-phosphate    P$_i$    MP    Glucose

PGM

Glucose 6-phosphate    (P$_i$)$_n$    PPGK    (P$_i$)$_{n-1}$

Starch

IA or PA

Amylodextrin

P$_i$

αGP

Maltose

Glucose 1-phosphate

P$_i$

MP

PGM

Glucose

Glucose 6-phosphate (P$_i$)$_n$

PPGK (P$_i$)$_{n-1}$

Starch

IA or PA

Amylodextrin $P_i$

αGP

Maltose

Glucose 1-phosphate $P_i$

MP

PGM

Glucose

Glucose 6-phosphate $(P_i)_n$

PPGK $(P_i)_{n-1}$

ENZYMATIC PRODUCTION OF HEXOSES

CROSS REFERENCE TO RELATED APPLICATIONS

This application is a Continuation application of U.S. application Ser. No. 17/825,484, filed May 26, 2022; which is a Divisional application of U.S. application Ser. No. 16/493,519, filed Sep. 12, 2019, now U.S. Pat. No. 11,345, 909; which is a national phase of PCT International Application No. PCT/US2018/022185, filed on Mar. 13, 2018; which claims priority to U.S. Application No. 62/470,605, filed on Mar. 13, 2017, U.S. Application No. 62/470,620, filed on Mar. 13, 2017, U.S. Application No. 62/482,148, filed on Apr. 5, 2017, and U.S. Application No. 62/480,798, filed on Apr. 3, 2017, which are hereby incorporated by reference in their entirety.

SEQUENCE LISTING

The Sequence Listing submitted herewith as an Extensible Markup Language (XML) file (2024-04-22_Sequence-_Listing.xml; created on Apr. 19, 2024; 24,909 bytes) via Patent Center is hereby incorporated by reference.

FIELD OF THE INVENTION

The invention relates to preparation of hexose monosaccharides. More specifically, the invention relates to methods of preparing a D-hexose (or hexose) from saccharides (e.g., polysaccharides, oligosaccharides, disaccharides, sucrose, D-glucose, and D-fructose) including a step in which fructose 6-phosphate is converted to the hexose by one or more enzymatic steps.

BACKGROUND

Hexoses are monosaccharides with six carbon atoms. Hexoses can be classified by functional group, with aldohexoses having an aldehyde at position 1, and ketohexoses having that ketone at position 2. Aldohexoses (or aldoses) include allose, altrose, glucose, gulose, galactose, idose, talose, and mannose. Ketohexoses (or ketoses) include psicose (allulose), fructose, tagatose, and sorbose. Various aspects of these aldohexoses and ketohexoses are mentioned in the following paragraphs.

For example, D-allose (allose hereafter) is a low-calorie, natural sweetener that has ~80% the sweetness of sucrose and is described as a noncaloric sweetening and bulking agent. It is a naturally occurring monosaccharide hexose that is present in only small amounts in specific shrubs and algae. Allose boasts several potential medical and agriculture benefits including cryoprotective, anti-oxidative, anti-hypertensive, immunosuppressive, anti-inflammatory, anti-tumor, and anti-cancer activities. It also has similar functionality in foods and beverages to sucrose. As such, allose clearly has a variety of applications in the food and beverage industries. However, due to allose's high selling prices, its use as a sweetener has been limited.

Currently allose is produced predominantly through the enzymatic isomerization of D-psicose (WO 2014069537). Overall, the method suffers because of higher feedstock cost, the costly separation of allose from D-psicose, and relatively low product yields (~23%).

Altrose is another unnatural aldohexose and C-3 epimer of mannose. D-Altrose ((2S,3R,4R,5R)-2,3,4,5,6-Pentahydroxyhexanal) can be used as a substrate to identify, differentiate and characterize aldose isomerases such as L-fucose isomerase from *Caldicellulosiruptor saccharolyticus* and d-Arabinose isomerase (d-AI) from *Bacillus pallidus* (*B. pallidus*) and *Klebsiella pneumoniae*. Recently, sugar chains such as oligosaccharides and polysaccharides, which perform functions useful as a physiologically active substance, have attracted attention in the field of fine chemicals such as medicines and agricultural chemicals. Presently, the objects of researches on the sugar chain are restricted to those consisting of monosaccharides present in nature in large amounts and readily available to researchers, such as D-glucose, D-mannose and D-galactose. However, it is expected that various monosaccharides other than those present in nature will be required in the future in research on the synthesis of sugar chains performing more useful functions. Under the circumstances, it is highly significant and necessary to develop a method which permits preparing D-altrose, which is a rare sugar difficult to obtain, in high yield while diminishing the number of treating steps. U.S. Pat. No. 5,410,038.

D-Gulose is useful, for example, as an excipient, a chelating agent, a pharmaceutical intermediate, a cleaning agent for glass and metals, a food additive, and as an additive for detergents. U.S. Pat. No. 5,215,591.

D-galactose (galactose hereafter) is a natural sweetener that has ~33% the sweetness of sucrose and is described as a nutritive sweetener. It is a naturally occurring monosaccharide hexose that is present in dairy products, legumes, grains, nuts, tubers and vegetables. Galactose is used by the baking industry to limit tartness and acidity in foods. Also, it is used as an energy source to increase endurance in the exercise supplement industry. In the pharmaceutical industry it is an intermediate for several medicines and is also used as a cell metabolism modulator in the optimization of protein therapeutics bioproduction. Additionally, galactose has been shown to be effective as a control agent against plant disease caused by certain plant pathogens, such as those affecting cucumber, carrot, potato and tomato plants. Due to dietary concerns (e.g. veganism) and health concerns (e.g. BSE disease) non-animal sources of galactose are of interest to industry. As such, galactose clearly has a variety of applications in the food, beverage, exercise, agriculture, and pharmaceutical industries. However, due to galactose's high selling prices, its use has been limited.

Galactose is produced predominantly through the hydrolysis of lactose (WO 2005039299A3). This method is less desirable due to a more costly feed stock and the expensive separation of glucose from galactose. Alternatively, galactose can be produced via the hydrolysis of plant-based biomass (WO 2005001145A1). This method suffers from the costly separation of galactose from the multiple other sugars released during biomass hydrolysis (e.g. xylose, arabinose, mannose, glucose, and rhamnose) and low yields (~4.6% of the dry mass of common biomass sources is galactose).

Idose is not found in nature, but its uronic acid, iduronic acid, is important. It is a component of dermatan sulfate and heparan sulfate, which are glycosaminoglycans. (en.wikipedia.org/wiki/Idose—accessed Mar. 7, 2018).

Talose is an unnatural aldohexose that is soluble in water and slightly soluble in methanol. It is a C-2 epimer of galactose and C-4 epimer of mannose. Talose can be used as a substrate to identify, differentiate, and characterize ribose-5-phosphate isomerase(s) of Clostridia.

D-mannose (mannose hereafter) is a mildly sweet, naturally-occurring monosaccharide that is found in many fruits, vegetables, plant materials, and even the human body.

Mannose boasts multiple health benefits and pharmaceutical applications. For example, mannose can be used to treat carbohydrate-deficient glycoprotein syndrome type 1b and, more commonly, urinary tract infections. Furthermore, mannose is a verified prebiotic, does not raise blood glucose levels, and shows anti-inflammatory properties. Additionally, it has been shown to enhance carcass yields in pigs and is a widely used auxiliary moisturizing agent for skin-care products. As such, mannose has a variety of applications in the pharmaceutical, cosmetic, beverage, food product, dairy, confectionery, and livestock industries. However, due to mannose's high selling prices, its use in everyday products has been limited.

Mannose is primarily produced through extraction from plants. Common methods include acid hydrolysis, thermal hydrolysis, enzymatic hydrolysis, microbial fermentation hydrolysis, and mixtures thereof. Less common methods include chemical and biological transformations. Overall, these methods are problematic due to harsh conditions, high capital expenditures, higher feedstock cost, costly separation of mannose from isomerization reactions, and relatively low product yields (15-35%).

D-allulose (also known as D-psicose) (psicose hereafter) is a low-calorie, natural sweetener that has 70% the sweetness of sucrose, but only 10% of the calories. It is a naturally occurring monosaccharide hexose that is present in only small amounts in wheat and other plants. Psicose was approved as a food additive by the Food and Drug Administration (FDA) in 2012, which designated it as generally recognized as safe (GRAS). However, due to psicose's high selling prices, its use as a sweetener has been limited. Psicose boasts a myriad of health benefits: it is low-calorie (10% of sucrose); it has a very low glycemic index of 1; it is fully absorbed in the small intestine but not metabolized and instead secreted in urine and feces; it helps regulate blood sugar by inhibiting alpha-amylase, sucrase and maltase; and it has similar functionality in foods and beverages as sucrose. As such, psicose clearly has a variety of applications in the food and beverage industries.

Currently psicose is produced predominantly through the enzymatic isomerization of fructose (WO 2014049373). Overall, the method exhibits higher feedstock cost, the costly separation of psicose from fructose, and relatively low product yields.

Fructose is a simple ketonic monosaccharide found in many plants, where it is often bonded to glucose to form the disaccharide, sucrose. Commercially, fructose is derived from sugar cane, sugar beets, and maize. The primary reason that fructose is used commercially in foods and beverages, besides its low cost, is its high relative sweetness. It is the sweetest of all naturally occurring carbohydrates. Fructose is also found in the manufactured sweetener, high-fructose corn syrup (HFCS), which is produced by treating corn syrup with enzymes, converting glucose into fructose. (en.wikipedia.org/wiki/Fructose #Physical_and_functional-_properties—accessed Mar. 7, 2018).

D-tagatose (tagatose hereafter) is a low-calorie, natural sweetener that has 92% the sweetness of sucrose, but only 38% of the calories. It is a naturally occurring monosaccharide hexose that is present in only small amounts in fruits, cacao, and dairy products. Tagatose was approved as a food additive by the Food and Drug Administration (FDA) in 2003, which designated it as generally recognized as safe (GRAS). However, due to tagatose's high selling prices, its use as a sweetener has been limited. Tagatose boasts a myriad of health benefits: it is non-cariogenic; it is low-calorie; it has a very low glycemic index of 3; it attenuates the glycemic index of glucose by 20%; it can lower average blood glucose levels; it helps prevent cardiovascular disease, strokes, and other vascular diseases by raising high-density lipoprotein (HDL) cholesterol; and it is a verified prebiotic and antioxidant. Lu et al., Tagatose, a New Antidiabetic and Obesity Control Drug, *Diabetes Obes. Metab.* 10(2): 109-34 (2008). As such, tagatose clearly has a variety of applications in the pharmaceutical, biotechnological, academic, food, beverage, dietary supplement, and grocer industries.

Tagatose is produced predominantly through the hydrolysis of lactose by lactase or acid hydrolysis to form D-glucose and D-galactose (WO 2011150556, CN 103025894, U.S. Pat. Nos. 5,002,612, 6,057,135, and 8,802,843). The D-galactose is then isomerized to D-tagatose either chemically by calcium hydroxide under alkaline conditions or enzymatically by L-arabinose isomerase under pH neutral conditions. The final product is isolated by a combination of filtration and ion exchange chromatography. This process is performed in several tanks or bioreactors. Overall, the method is disadvantageous because of the costly separation of other sugars (e.g., D-glucose, D-galactose, and unhydrolyzed lactose) and low product yields. Several methods via microbial cell fermentation are being developed, but none have been proven to be a practical alternative due to their dependence on costly feedstock (e.g., galactitol and D-psicose), low product yields, and costly separation.

Sorbose ((3R,4S,5R)-1,3,4,5,6-pentahydroxyhexan-2-one) is a ketohexose that has a sweetness equivalent to sucrose (table sugar), and it is a plant metabolite that has been found to naturally occur in grapes in small quantities. D-sorbose has been determined to be effective as a control agent of plant diseases caused by: *Pseudomonas syringae* pv. *lachrymans* and *Ralstonia solanacearum*. United States Patent Application Publication No. 2016/0037768.

There is a need to develop cost-effective synthetic pathways for high-yield production of the hexoses such as the aldohexoses and aldoketoses discussed above where at least one step of the processes involves an energetically favorable chemical reaction. Furthermore, there is a need for production processes where the process steps can be conducted in one tank or bioreactor and/or where costly separation steps are avoided or eliminated. There is also a need for processes of hexose production that can be conducted at a relatively low concentration of phosphate, where phosphate can be recycled, and/or the process does not require using adenosine triphosphate (ATP) as an added source of phosphate. There is also a need for hexose production pathways that do not require the use of the costly nicotinamide adenosine dinucleotide (NAD(P)(H)) coenzyme in any of the reaction steps.

SUMMARY OF THE INVENTION

The inventions described herein generally relate to processes for preparing hexoses from saccharides by enzymatic conversion. The inventions also relate to hexoses prepared by any of the processes described herein.

More specifically, the invention relates to processes for preparing a hexose, selected from allose, mannose, galactose, fructose, altrose, talose, sorbose, gulose and idose, from a saccharide, the process comprising: converting fructose 6-phosphate (F6P) to the hexose catalyzed by one or more enzymes selected from an isomerase, an epimerase, and a hexose-specific phosphatase and mixtures thereof.

A process of the invention for the production of allose comprises converting the F6P to psicose 6-phosphate (P6P) catalyzed by psicose 6-phosphate 3-epimerase (P6PE); converting the P6P to allose 6-phosphate (A6P) catalyzed by allose 6-phosphate isomerase (A6PI); and converting the A6P to allose catalyzed by allose 6-phosphate phosphatase (A6PP).

A process of the invention for the production of mannose comprises converting the F6P to mannose 6-phosphate (M6P) catalyzed by mannose 6-phosphate isomerase (M6PI) or phosphoglucose/phosphomannose isomerase (PGPMI); and converting the M6P to mannose catalyzed by mannose 6-phosphate phosphatase (M6PP).

A process of the invention for the production of galactose comprises converting the F6P to tagaose 6-phosphate (T6P) catalyzed by fructose 6-phosphate 4-epimerase (F6PE); converting the T6P to galactose 6-phosphate (Gal6P) catalyzed by galactose 6-phosphate isomerase (Gal6PI); and converting the Gal6P to galactose catalyzed by galactose 6-phosphate phosphatase (Gal6PP).

A process of the invention for the production of fructose comprises converting the F6P to fructose catalyzed by fructose 6-phosphate phosphatase (F6PP).

A process of the invention for the production of altrose comprises converting the F6P to converting the F6P to P6P catalyzed by P6PE; converting the P6P to altrose 6-phosphate (Alt6P) catalyzed by altrose 6-phosphate isomerase (Alt6PI); and converting the Alt6P produced to altrose catalyzed by altrose 6-phosphate phosphatase (Alt6PP).

A process of the invention for the production of talose comprises converting the F6P to T6P catalyzed by F6PE; converting the T6P to talose 6-phosphate (Tal6P) catalyzed by talose 6-phosphate isomerase (Tal6PI); and converting the Tal6P to talose catalyzed by talose 6-phosphate phosphatase (Tal6PP).

A process of the invention for the production of sorbose comprises converting the F6P to T6P catalyzed by F6PE; converting the T6P to sorbose 6-phosphate (S6P) catalyzed by sorbose 6-phosphate epimerase (S6PE); and converting the S6P to sorbose catalyzed by sorbose 6-phosphate phosphatase (S6PP).

A process of the invention for the production of gulose comprises converting the F6P to T6P catalyzed by F6PE; converting the S6P to gulose 6-phosphate (Gul6P) catalyzed by gulose 6-phosphate isomerase (Gul6PI); and converting the Gul6P to gulose catalyzed by gulose 6-phosphate phosphatase (Gul6PP).

A process of the invention for the production of gulose comprises converting the F6P to T6P catalyzed by F6PE; converting the T6P to sorbose 6-phosphate (S6P) catalyzed by sorbose 6-phosphate epimerase (S6PE); converting the S6P to idose 6-phosphate (I6P) catalyzed by idose 6-phosphate isomerase (I6PI); and converting the I6P to idose catalyzed by idose 6-phosphate phosphatase (I6PP).

The processes of hexose production according to the invention can involve a step of converting glucose 6-phosphate (G6P) to the F6P, wherein the step is catalyzed by phosphoglucose isomerase (PGI). The processes can also comprise the step of converting glucose 1-phosphate (G1P) to the G6P, wherein the step is catalyzed by phosphoglucomutase (PGM). Additionally, the processes according to the invention may further comprise the step of converting a saccharide to the G1P, where the step is catalyzed by at least one enzyme, and the saccharide is selected from the group consisting of a starch or derivative thereof, cellulose or a derivative thereof, and sucrose.

The enzyme or enzymes used in the step of converting a saccharide to the G1P in the processes according to the invention can be alpha-glucan phosphorylase (αGP), maltose phosphorylase, sucrose phosphorylase, cellodextrin phosphorylase, cellobiose phosphorylase, and/or cellulose phosphorylase, and mixtures thereof. When the saccharide is starch or a starch derivative, the derivative may be selected from the group consisting of amylose, amylopectin, soluble starch, amylodextrin, maltodextrin, maltose, and glucose, and mixtures thereof.

Some processes according to the invention, may further comprise the step of converting starch to a starch derivative, where the starch derivative is prepared by enzymatic hydrolysis of starch or by acid hydrolysis of starch. Also, 4-glucan transferase (4GT) can be added to the processes. 4GT can be used to increase hexose yields by recycling the degradation products glucose, maltose, and maltotriose into longer maltooligosaccharides; which can be phosphorolytically cleaved by αGP to yield G1P.

Where the processes use a starch derivative, the starch derivative can be prepared by enzymatic hydrolysis of starch catalyzed by isoamylase, pullulanase, alpha-amylase, or their combination.

The process according to the inventions can also comprise the step of converting fructose to the F6P, wherein the step is catalyzed by at least one enzyme and, optionally, the step of converting sucrose to the fructose, wherein the step is catalyzed by at least one enzyme.

Furthermore, the processes of producing a hexose according to the inventions can comprise the step of converting glucose to the G6P, where the step is catalyzed by at least one enzyme, and, optionally, the step of converting sucrose to the glucose that is catalyzed by at least one enzyme.

The steps in each of the processes of hexose synthesis according to the invention can be conducted at a temperature ranging from about 40° C. to about 90° C. and at a pH ranging from about 5.0 to about 8.0. They may be conducted for about 8 hours to about 48 hours.

The steps of the processes according to the inventions can be conducted in a single bioreactor. The steps can also be conducted in a plurality of bioreactors arranged in series.

The enzymatic process steps of the inventions may be conducted ATP-free and/or NAD(P)(H)-free. The steps can be carried out at a phosphate concentration ranging from about 0.1 mM to about 150 mM. The phosphate used in the phosphorylation and dephosphorylation steps of the processes according to the inventions can be recycled. At least one step of the processes may involve an energetically favorable chemical reaction.

The invention also relates to allose, mannose, galactose, fructose, altrose, talose, sorbose, gulose and idose produced by these processes.

DESCRIPTION OF THE INVENTION

Figure 1:
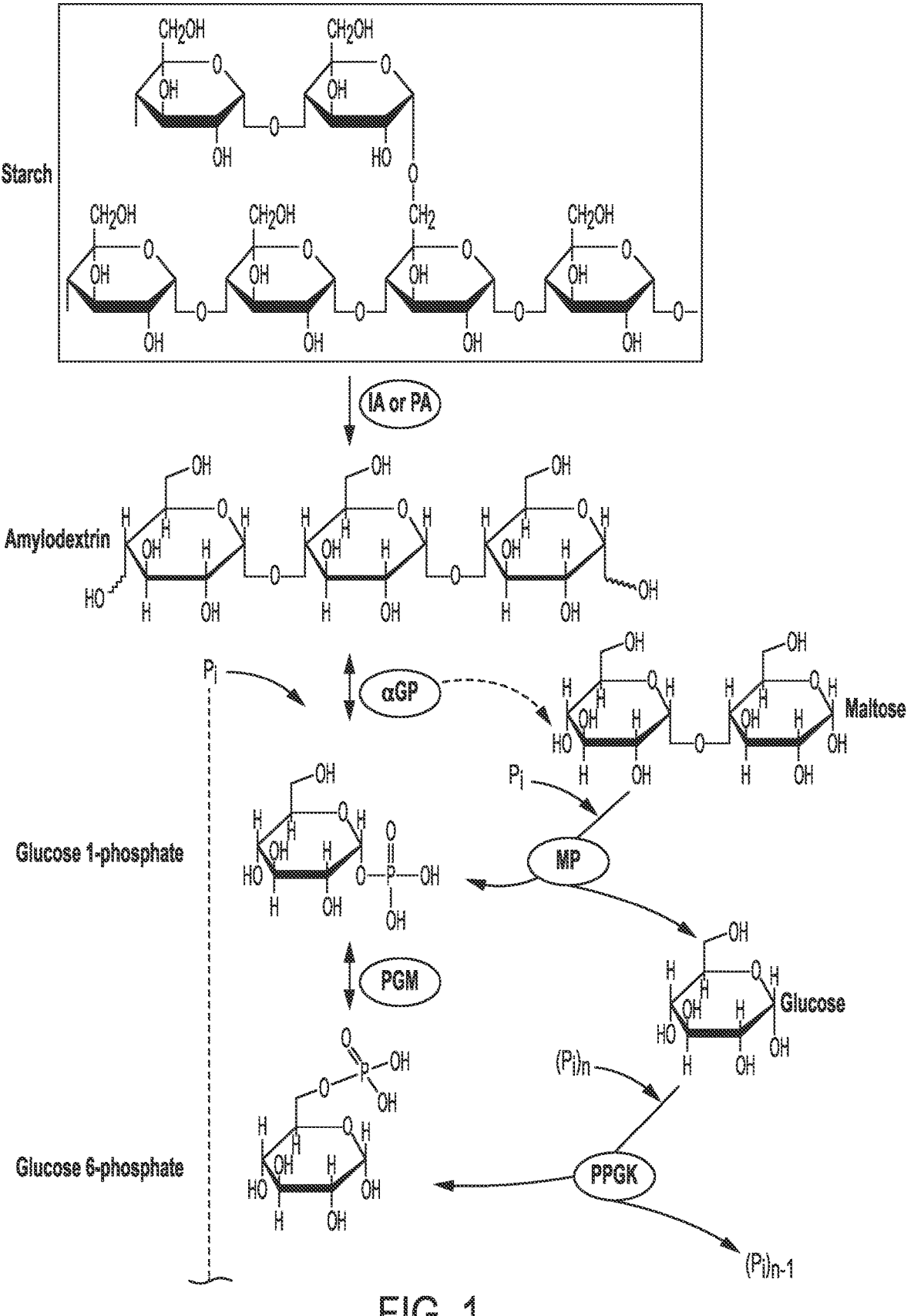
FIG. 1 is a schematic diagram showing an enzymatic pathway converting starch or its derived products to allose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; P6PE, psicose 6-phosphate 3-epimerase; A6PI, allose 6-phosphate isomerase; A6PP, allose 6-phosphate phosphatase.

The inventions described herein provide enzymatic pathways, or processes, for synthesizing hexoses with a high product yield, while greatly decreasing the product separation costs and hexose production costs. Also described herein are hexoses produced by these process.

Processes according to the invention for preparing a hexose from a saccharide, comprise: converting fructose 6-phosphate (F6P) to the hexose, catalyzed by one or more enzymes, wherein the hexose is selected from the group consisting of allose, mannose, galactose, fructose, altrose, talose, sorbose, gulose and idose; and wherein the enzymes are selected from the group consisting of an isomerase, an epimerase, and a hexose-specific phosphatase, and mixtures thereof.

One of the important advantages of the processes of the invention is that the process steps can be conducted in a single bioreactor or reaction vessel. Alternatively, the steps can also be conducted in a plurality of bioreactors, or reaction vessels, that are arranged in series.

Phosphate ions produced during the dephosphorylation step can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the hexose making processes.

For example, reaction phosphate concentrations in each of the processes can range from about 0.1 mM to about 300 mM, from about 0 mM to about 150 mM, from about 1 mM to about 50 mM, preferably from about 5 mM to about 50 mM, or more preferably from about 10 mM to about 50 mM. For instance, the reaction phosphate concentration in each of the processes can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Low phosphate concentration results in decreased production costs due to low total phosphate and thus lowered cost of phosphate removal. It also prevents inhibition of phosphatases by high concentrations of free phosphate and decreases the potential for phosphate pollution.

Furthermore, each of the processes disclosed herein can be conducted without added ATP as a source of phosphate, i.e., ATP-free. Each of the processes can also be conducted without having to add NAD(P)(H), i.e., NAD(P)(H)-free. Other advantages also include the fact that at least one step of the disclosed processes for making a hexose involves an energetically favorable chemical reaction.

Examples of the enzymes used to convert a saccharide to G1P include alpha-glucan phosphorylase (αGP, EC 2.4.1.1), maltose phosphorylase (MP, EC 2.4.1.8), cellodextrin phosphorylase (CDP, EC 2.4.1.49), cellobiose phosphorylase (CBP, EC 2.4.1.20), cellulose phosphorylase, sucrose phosphorylase (SP, EC 2.4.1.7), and a combination thereof. The choice of the enzyme or enzyme combination depends on the saccharide used in the process.

The saccharides used for generating G1P can be polysaccharides, oligosaccharides, and/or disaccharides. For example, the saccharide can be starch, one or more derivatives of starch, cellulose, one or more derivatives of cellulose, sucrose, one or more derivatives of sucrose, or a combination thereof.

Starch is the most widely used energy storage compound in nature and is mostly stored in plant seeds. Natural starch contains linear amylose and branched amylopectin. Examples of starch derivatives include amylose, amylopectin, soluble starch, amylodextrin, maltodextrin, maltose, fructose, and glucose. Examples of cellulose derivatives include pretreated biomass, regenerated amorphous cellulose, cellodextrin, cellobiose, fructose, and glucose. Sucrose derivatives include fructose and glucose.

Methods of preparing F6P from starch and its derivatives, cellulose and its derivatives, and sucrose and its derivatives can be found, for example in International Patent Application Publication No. WO 2017/059278.

The derivatives of starch can be prepared by enzymatic hydrolysis of starch or by acid hydrolysis of starch. Specifically, the enzymatic hydrolysis of starch can be catalyzed or enhanced by isoamylase (IA, EC. 3.2.1.68), which hydrolyzes α-1,6-glucosidic bonds; pullulanase (PA, EC. 3.2.1.41), which hydrolyzes α-1,6-glucosidic bonds; 4-a-glucanotransferase (4GT, EC. 2.4.1.25), which catalyzes the transglycosylation of short maltooligosaccharides, yielding longer maltooligosaccharides; or alpha-amylase (EC 3.2.1.1), which cleaves a-1,4-glucosidic bonds.

Furthermore, derivatives of cellulose can be prepared by enzymatic hydrolysis of cellulose catalyzed by cellulase mixtures, by acids, or by pretreatment of biomass.

Enzymes used to convert a saccharide to G1P may contain αGP. In this step, when the saccharides include starch, the G1P is generated from starch by αGP; when the saccharides contain soluble starch, amylodextrin, or maltodextrin, the G1P is produced from soluble starch, amylodextrin, or maltodextrin by αGP.

When the saccharides include maltose and the enzymes contain maltose phosphorylase, the G1P is generated from maltose by maltose phosphorylase. If the saccharides include sucrose, and enzymes contain sucrose phosphorylase, the G1P is generated from sucrose by sucrose phosphorylase.

When the saccharides include cellobiose, and the enzymes contain cellobiose phosphorylase, the G1P may be produced from cellobiose by cellobiose phosphorylase.

When the saccharides contain cellodextrins and the enzymes include cellodextrin phosphorylase, the G1P can be generated from cellodextrins by cellodextrin phosphorylase.

In converting a saccharide to G1P, when the saccharides include cellulose, and enzymes contain cellulose phosphorylase, the G1P may be generated from cellulose by cellulose phosphorylase.

According to the invention, a hexose can also be produced from fructose. For example, the process involves generating F6P from fructose and polyphosphate catalyzed by polyphosphate fructokinase (PPFK); converting F6P to T6P catalyzed by F6PE; and converting T6P to tagatose catalyzed by T6PP. The fructose can be produced, for example, by an enzymatic conversion of sucrose.

A hexose can be produced from sucrose. The process, for example, provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; and converting T6P to tagatose catalyzed by T6PP.

The phosphatase used in the processes of the invention is specific for the hexose. For example, allose 6-phosphate is converted to allose by allose 6-phosphate phosphatase; mannose 6-phosphate is converted to mannose by mannose 6-phosphate phosphatase; galactose 6-phosphate is converted to galactose by galactose 6-phosphate phosphatase; fructose 6-phosphate is converted to fructose by fructose 6-phosphate phosphatase; altrose 6-phosphate is converted to altrose by altrose 6-phosphate phosphatase; talose 6-phosphate is converted to talose by talose 6-phosphate phosphatase; sorbose 6-phosphate is converted to sorbose by sorbose 6-phosphate phosphatase; gulose 6-phosphate is converted to gulose by gulose 6-phosphate phosphatase; and idose 6-phosphate is converted to idose by idose 6-phosphate phosphatase. As used herein, specific means having a higher specific activity for the indicated hexose over other hexoses. For instance, allose 6-phosphate phosphatase has a higher specific activity on allose 6-phosphate than, for example, sorbose 6-phosphate or talose 6-phosphate.

The phosphate ions generated during the hexose dephosphorylation step can then be recycled in the step of converting sucrose to G1P. Additionally, PPFK and polyphosphate can be used to increase hexose yields by producing F6P from fructose generated by the phosphorolytic cleavage of sucrose by SP.

A process for preparing a hexose can include the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above. G6P may be produced from glucose and sodium polyphosphate by polyphosphate glucokinase.

The invention provides processes for converting saccharides, such as polysaccharides and oligosaccharides in starch, cellulose, sucrose and their derived products, to a hexose. Artificial (non-natural) ATP-free enzymatic pathways may be provided to convert starch, cellulose, sucrose, and their derived products to a hexose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to a hexose and enhanced solubility.

Maltose phosphorylase (MP) can be used to increase hexose yields by phosphorolytically cleaving the degradation product maltose into G1P and glucose. Alternatively, 4-glucan transferase (4GT) can be used to increase hexose yields by recycling the degradation products glucose, maltose, and maltotriose into longer maltooligosaccharides; which can be phosphorolytically cleaved by αGP to yield G1P.

Additionally, cellulose is the most abundant bio resource and is the primary component of plant cell walls. Non-food lignocellulosic biomass contains cellulose, hemicellulose, and lignin as well as other minor components. Pure cellulose, including Avicel (microcrystalline cellulose), regenerated amorphous cellulose, bacterial cellulose, filter paper, and so on, can be prepared via a series of treatments. The partially hydrolyzed cellulosic substrates include water-insoluble cellodextrins whose degree of polymerization is more than 7, water-soluble cellodextrins with degree of polymerization of 3-6, cellobiose, glucose, and fructose.

Cellulose and its derived products can be converted to a hexose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

Prior to cellulose hydrolysis and G1P generation, cellulose and biomass can be pretreated to increase their reactivity and decrease the degree of polymerization of cellulose chains. Cellulose and biomass pretreatment methods include dilute acid pretreatment, cellulose solvent-based lignocellulose fractionation, ammonia fiber expansion, ammonia aqueous soaking, ionic liquid treatment, and partially hydrolyzed by using concentrated acids, including hydrochloric acid, sulfuric acid, phosphoric acid and their combinations.

Polyphosphate and polyphosphate glucokinase (PPGK) can be added to the processes according to the invention, thus increasing yields of a hexose by phosphorylating the degradation product glucose to G6P.

A hexose can be generated from glucose. The processes for hexose production may involve the steps of generating G6P from glucose and polyphosphate catalyzed by polyphosphate glucokinase (PPGK) and converting G6P to F6P catalyzed by PGI.

Any suitable biologically compatible buffering agent known in the art can be used in each of the processes of the invention, such as HEPES, PBS, BIS-TRIS, MOPS, DIPSO, Trizma, etc. The reaction buffer for the processes according to the invention can have a pH ranging from 5.0-8.0. More preferably, the reaction buffer pH can range from about 6.0 to about 7.3. For example, the reaction buffer pH can be 6.0, 6.2, 6.4, 6.6, 6.8, 7.0, 7.2, or 7.3.

The reaction buffer can also contain metal cations. Examples of the metal ions include $Mg^{2+}$ and $Zn^{2+}$. As known in the art, suitable salts may be used to introduce the desired metal cation.

In each of the processes of the invention the reaction temperature at which the process steps are conducted can range from 37-95° C. More preferably, the steps can be conducted at a temperature ranging from about 40° C. to about 90° C. The temperature can be, for example, about 40° C., about 45° C., about 50° C., about 55° C., about 60° C., about 65° C., about 70° C., about 75° C., about 80° C., about 85° C., or about 90° C. Preferably, the reaction temperature is about 50° C.

The reaction time of each of the disclosed processes can be adjusted as necessary, and can range from about 8 hours to about 48 hours. For example, the reaction time can be about 16 hours, about 18 hours, about 20 hours, about 22 hours, about 24 hours, about 26 hours, about 28 hours, about 30 hours, about 32 hours, about 34 hours, about 36 hours, about 38 hours, about 40 hours, about 42 hours, about 44 hours, about 46 hours, or about 48 hours. More preferably, the reaction time is about 24 hours.

Typically, the ratios of enzyme units used in each of the disclosed processes are 1:1 to 1:1:1:1:1 (depending on the number of catalyzed steps in the process). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1, 4-glycosidic bonds. A ratio of enzymes, for example, 3:1:1:3 can be used to further increase the reaction rate. Therefore, the enzyme ratios, including other optional enzymes discussed below, can be varied to increase the efficiency of hexose production. For example, a particular enzyme may be present in an amount about 2×, 3×, 4×, 5×, etc. relative to the amount of other enzymes.

Figure 11:
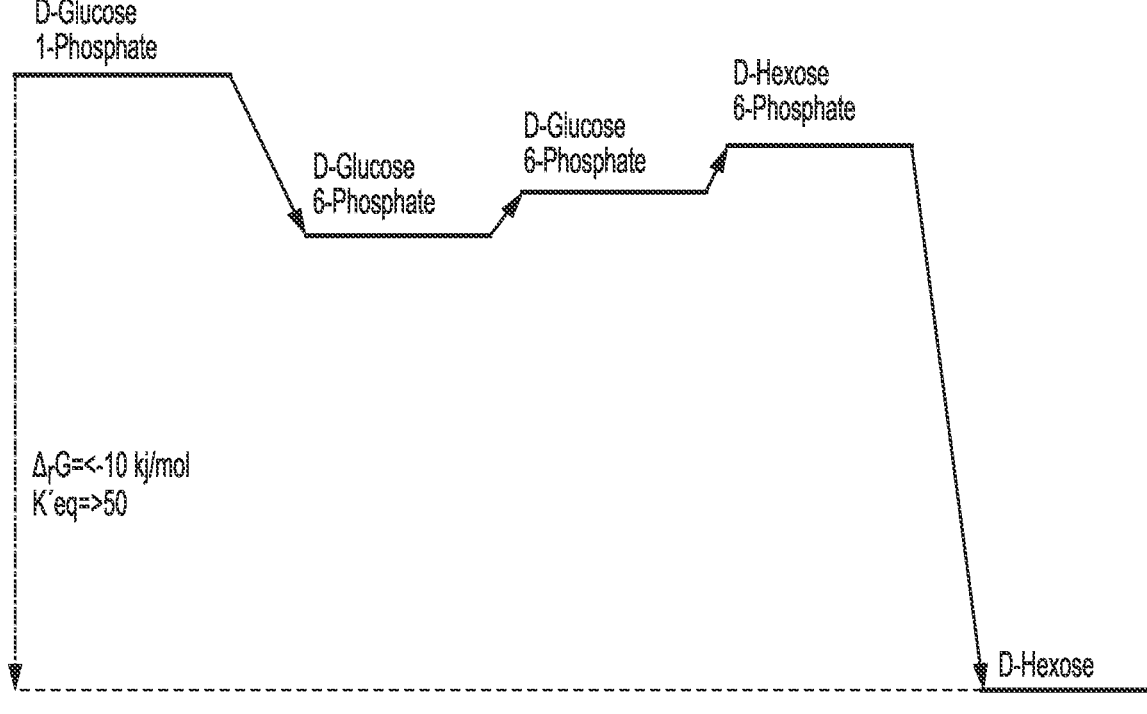
FIG. 11 shows the Reaction Gibbs Energy between intermediates based on formation Gibbs energy for the conversion of glucose 1-phosphate to another hexose.

Each of the processes according to the invention can achieve high yields due to the very favorable equilibrium constant for the overall reaction. For example, FIG. 11 shows the Reaction Gibbs Energy between intermediates based on formation Gibbs energy for the conversion of glucose 1-phosphate to a hexose. Reaction Gibbs Energies were generated using equilibrator.weizmann.ac.il/. Theoretically, up to 99% yields can be achieved if the starting material is completely converted to an intermediate.

Processes of the invention use low-cost starting materials and reduce production costs by decreasing costs associated with the feedstock and product separation. Starch, cellulose, sucrose and their derivatives are less expensive feedstocks than, for example, lactose. When a hexose is produced from lactose, glucose and other hexose(s) are separated via chromatography, which leads to higher production costs.

Also, the step of hexose dephosphorylation by a phosphatase according to the invention is an irreversible phosphatase reaction, regardless of the feedstock. Therefore, hexose is produced with a very high yield while effectively minimizing the subsequent product separation costs.

In some aspects of the invention, phosphatases to convert A6P, M6P, F6P, or Gal6P to their respective non-phosphorylated forms utilize a divalent metal cofactor: preferably magnesium. In further aspects of the invention the phosphatase contains but is not limited to containing a Rossmanoid fold domain for catalysis; additionally but not limited to containing a C1 or C2 capping domain for substrate specificity; additionally but not limited to containing a DxD signature in the 1st β-strand of the Rossmanoid fold for coordinating magnesium where the second Asp is a general acid/base catalyst; additionally but not limited to containing a Thr or Ser at the end of the 2nd β-strand of the Rossmanoid fold that helps stability of reaction intermediates; additionally but not limited to containing a Lys at the N-terminus of the α-helix C-terminal to the 3rd β-strand of the Rossmanoid fold that helps stability of reaction intermediates; and additionally but not limited to containing a GDxxxD, GDxxxxD, DD, or ED signature at the end of the 4th β-strand of the Rossmanoid fold for coordinating magnesium. These features are known in the art and are referenced in, for example, Burroughs et al., Evolutionary Genomics of the HAD Superfamily: Understanding the Structural Adaptations and Catalytic Diversity in a Superfamily of Phosphoesterases and Allied Enzymes. J. Mol. Biol. 2006; 361; 1003-1034.

In contrast to cell-based manufacturing methods, the invention involves a cell-free preparation of a hexose, has relatively high reaction rates due to the elimination of the cell membrane, which often slows down the transport of substrate/product into and out of the cell. It also has a final product free of nutrient-rich fermentation media/cellular metabolites.

Allose

One embodiment of the invention is a process for preparing allose which includes converting fructose 6-phosphate (F6P) to psicose 6-phosphate (P6P) catalyzed by psicose 6-phosphate 3-epimerase (P6PE), converting P6P to allose 6-phosphate (A6P) catalyzed by allose 6-phosphate isomerase (A6PI), and converting the A6P produced to allose catalyzed by allose 6-phosphate phosphatase.

Examples of P6PEs include, but are not limited to the following proteins, identified by UNIPROT ID numbers: D9TQJ4, A0A090IXZ8, and P32719. Of these, D9TQJ4 and A0A090IXZ8 are obtained from thermophilic organisms. P32719 is obtained from a mesophilic organism. P32719 is 53% identical to A0A090IXZ8 and 55% identical to D9TQJ4, and each protein catalyzes the epimerization of F6P to A6P. Furthermore, A0A090IXZ8 is 45% identical to D9TQJ4. Conversely, other epimerase proteins identified by UNIPROT ID numbers: A0A101D823, R1AXD6, A0A150LBU8, A0A023CQG9, and H1XWY2, which have a degree of identity to D9TQJ4 of 45% or less do not catalyze the epimerization of F6P to A6P. Examples of P6PEs also include any homologues having at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

Examples of A6PIs include, but are not limited to Uniprot ID W4V2C8, with the amino acid sequence set forth in SEQ ID NO: 1; and Uniprot ID Q67LX4, with the amino acid sequence set forth in SEQ ID NO: 2. Uniprot IDs W4V2C8 and Q67LX4 both catalyze the A6PI reaction and share 56% amino acid sequence identity. Therefore, examples of A6PIs also include any homologues having at least 55%, preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

A6PIs suitable for use in the process to convert P6P to A6P contain a Rossmanoid fold. A mesophilic A6PI described in the art (Mowbray et al., D-Ribose-5-Phosphate Isomerase B from *Escherichia coli* is Also a Functional D-Allose-6-phosphate Isomerase, While the *Mycobacterium tuberculosis* Enzyme is Not. J. Mol. Biol. 2008; 382; 667-679) shares conserved residues with the thermophilic A6PI disclosed in the invention. In some aspects of the invention the isomerase contains but is not limited to containing a His (mesophilic residue 10) C-terminal to the 1st β-strand of the Rossmanoid fold for phosphate binding; additionally but not limited to containing an Arg (mesophilic residue 133) C-terminal to the α-helix C-terminal to the 5th β-strand of the Rossmanoid fold also for phosphate binding; additionally but not limited to containing a His (mesophilic residue 99) in the active site to ring open the lactone; additionally but not limited to containing a Cys (mesophilic reside 66) in the active site to act as the catalytic base; additionally but not limited to containing a Thr (mesophilic residue 68) in the active site to act as the catalytic acid; additionally but not limited to containing a GTG-hydrophobic-G motif near the active site (mesophilic residues 67-71) to stabilize high energy intermediates, and additionally but not limited to containing a Asn (mesophilic residue 100) near the active site to also stabilize high energy intermediates. An A6PI preferably contains all of these conserved residues.

Examples of A6PPs include, but are not limited to the following proteins: Uniprot ID S9SDA3, with the amino acid sequence set forth in SEQ ID NO: 3; Q9X0Y1, with the amino acid sequence set forth in SEQ ID NO: 4; I3VT81, with the amino acid sequence set forth in SEQ ID NO: 5; A0A132NF06, with the amino acid sequence set forth in SEQ ID NO: 6; and D1C7G9, with the amino acid sequence set forth in SEQ ID NO: 7. Uniprot IDs S9SDA3 and I3VT81 both catalyze the A6PP reaction and share 30% amino acid sequence identity. Therefore, examples of A6PPs also include any homologues having at least 30%, preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Preferably, an A6PP to convert A6P to allose, contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd 1-strand of the Rossmanoid fold, and a ED signature at the end of the 4th β-strand of the Rossmanoid fold.

A process for preparing allose according to the invention also includes the step of enzymatically converting glucose 6-phosphate (G6P) to the F6P, and this step is catalyzed by phosphoglucoisomerase (PGI). In other embodiments, the process for preparing allose additionally includes the step of converting glucose 1-phosphate (G1P) to the G6P, where the step is catalyzed by phosphoglucomutase (PGM). In yet further embodiments, allose production process also includes the step of converting a saccharide to the G1P that is catalyzed at least one enzyme.

Therefore, a process for preparing allose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to P6P via P6PE, (v) converting P6P to A6P via A6PI, and (vi) converting A6P to allose via A6PP. An example of the enzymatic process where the saccharide is starch is shown in FIG. 1.

Typically, the ratios of enzyme units used in the disclosed process are 1:1:1:1:1:1 (αGP:PGM:PGI:P6PE:A6PI:A6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of allose production. For example, a particular enzyme may be present in an amount about 2×, 3×, 4×, 5×, etc. relative to the amount of other enzymes.

Phosphate ions produced by dephosphorylation of A6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the allose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Low phosphate concentration results in decreased production costs due to low total phosphate and thus lowered cost of phosphate removal. It also prevents inhibition of the A6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making allose involves an energetically favorable reaction.

Allose can also be produced from fructose. For example, the process involves generating F6P from fructose and polyphosphate catalyzed by polyphosphate fructokinase (PPFK); converting F6P to P6P catalyzed by P6PE; converting P6P to A6P catalyzed by A6PI, and converting A6P to allose catalyzed by A6PP. The fructose can be produced, for example, by an enzymatic conversion of sucrose.

Allose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to P6P catalyzed by P6PE; converting P6P to A6P catalyzed by A6PI, and converting A6P to allose catalyzed by A6PP.

The phosphate ions generated when A6P is converted to allose can then be recycled in the step of converting sucrose to G1P. Additionally, PPFK and polyphosphate can be used to increase allose yields by producing F6P from fructose generated by the phosphorolytic cleavage of sucrose by SP.

In certain embodiments, a process for preparing allose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

Several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to allose and increased solubility.

Maltose phosphorylase (MP) can be used to increase allose yields by phosphorolytically cleaving the degradation product maltose into G1P and glucose. Alternatively, 4-glucan transferase (4GT) can be used to increase allose yields by recycling the degradation products glucose, maltose, and maltotriose into longer maltooligosaccharides; which can be phosphorolytically cleaved by αGP to yield G1P.

In certain embodiments, cellulose and its derived products can be converted to allose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to P6P catalyzed by P6PE; converting P6P to A6P catalyzed by A6PI, and converting A6P to allose catalyzed by A6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

In some embodiments, polyphosphate and polyphosphate glucokinase (PPGK) can be added to the process, thus increasing yields of allose by phosphorylating the degradation product glucose to G6P.

Allose can be produced from glucose. The process involves the steps of generating G6P from glucose and polyphosphate catalyzed by polyphosphate glucokinase (PPGK); converting G6P to F6P catalyzed by PGI; converting F6P to P6P catalyzed by P6PE; converting P6P to A6P catalyzed by A6PI; and converting A6P to allose catalyzed by A6PP.

Processes of the invention for making allose use low-cost starting materials and reduce production costs by decreasing costs associated with the feedstock and product separation. Starch, cellulose, sucrose and some of their derivatives are less expensive feedstocks than, for example, fructose. When allose is produced from psiose, yields are lower than in the present invention, and allose must be separated from psicose via chromatography, which leads to higher production costs.

Also, the step of converting A6P to allose according to the invention is an irreversible phosphatase reaction, regardless of the feedstock. Therefore, allose is produced with a very high yield while effectively minimizing the subsequent product separation costs.

In contrast to cell-based manufacturing methods, the invention involves a cell-free preparation of allose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is allose produced by the processes described herein for producing allose.

Since allose as similar functionality to sucrose, allose prepared by processes of the invention may be added to any beverage or foodstuff to produce desired sweetness.

Allose prepared by the processes disclosed herein may also be used used to synergize the effect of potent sweeteners. When combined with one or more potent sweeteners, allose may be able to effect improvements in sensory characteristics such as mouthfeel, flavor and aftertaste of a sweetened product. The use of low calorie sweeteners, such as potent sweeteners, in a variety of food products is common place in food and beverage formulations. For many consumers, however, products marketed as diet or light versions of products that are artificially sweetened are not preferred. Attempts have been made over the years to improve the taste delivery of these diet or light products through the addition of small quantities of carbohydrates. Allose prepared the processes of the invention would not only able to effect improvements in the quality of food and beverage formulations, particularly in diet/light beverages, but that its use may be synergistic with potent sweeteners such that it is able to replace significant quantities of potent sweeteners, even when it is added at concentrations well below its measured sweet taste threshold.

Allose produced by processes disclosed herein may be combined with other sweeteners, such as extracts from the *Stevia rebaudiana* Bertoni plant for the preparation of low calorie versions of foods such as ice cream.

Allose produced by processes disclosed herein may be used in presweetened ready to eat (RTE) breakfast cereals and other foods wherein D allose partially or totally replaces sucrose or other commonly used sugars, as a frosting.

Allose produced by processes disclosed herein may be used as part of a sweetener for foods and beverages in combination with sugar alcohols, such as erythritol, and nutritive sweeteners with significant caloric content, such as fructose, sucrose, dextrose, maltose, trehalose, rhamnose, corn syrups and fructo-oligosaccharides.

Allose produced by the processes disclosed herein may also be used as part of a composition that enhances the plant disease control.

Mannose

One embodiment of the invention is a process for preparing mannose which includes converting F6P to mannose 6-phosphate (M6P) catalyzed by mannose 6-phosphate isomerase (M6PI); and converting the M6P to mannose catalyzed by mannose 6-phosphate phosphatase (M6PP).

Examples of M6PIs include, but are not limited to the following proteins: Uniprot ID A0A1M6TLY7, with the amino acid sequence set forth in SEQ ID NO: 8; H1XQS6, with the amino acid sequence set forth in SEQ ID NO: 9; G2Q982, with the amino acid sequence set forth in SEQ ID NO: 10; and F8F1Z8, with the amino acid sequence set forth in SEQ ID NO: 11. Uniprot IDs G2Q982 and F8F1Z8 both perform the M6PI reaction and share 28% amino acid sequence identity. Therefore, examples of M6PIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

M6PIs suitable for use in the process to convert F6P to M6P contain two domains with a core of antiparallel β-strands resembling the cupin fold and a third domain consisting of only α-helixes. A M6PI was structurally characterized in the art (Sagurthi et al. Structures of mannose-6-phosphate isomerase from *Salmonella typhimurium* bound to metal atoms and substrate: implications for catalytic mechanism. Acta Cryst. 2009; D65; 724-732) and shares conserved residues with the thermophilic M6PIs described in the invention. In some aspects of the invention the isomerase contains but is not limited to containing a divalent metal cation, preferably $Mg^{2+}$ or $Zn^{2+}$; additionally but not limited to containing a Glu and two His residues proposed for use in metal binding (PDB 3H1M residues 134, 99, and 255 respectively); additionally but not limited to containing an Asp and Lys residue proposed for acid/base catalysis (PDB 3H1M residues 270 and 132 respectively); and additionally but not limited to containing a Lys, Pro, and Ala residue proposed for phosphate binding (PDB 3H1M residues 132, 133, and 267 respectively). An M6PI preferably contains all of these conserved residues.

Examples of M6PPs include, but are not limited to the following proteins: Uniprot ID A0A1A6DSI3, with the amino acid sequence set forth in SEQ ID NO: 12; A0A1M4UN08, with the amino acid sequence set forth in SEQ ID NO: 13; and A0A1N6FCW3, with the amino acid sequence set forth in SEQ ID NO: 14 Uniprot IDs A0A1A6DSI3 and A0A1N6FCW3 both catalyze the M6PP reaction and share 35% amino acid sequence identity. Therefore, examples of M6PPs also include any homologues having at least 35%, more preferably at least 40%, preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Preferably, an M6PP to convert M6P to mannose contains a Rossmanoid fold domain for catalysis, a C1 capping domain, DxD signature in the 1st β-strand of the Rossmanoid fold, a Thr or Ser at the end of the 2nd β-strand of the Rossmanoid fold, a Lys at the N-terminus of the α-helix C-terminal to the 3rd β-strand of the Rossmanoid fold, and a GDxxxD signature at the end of the 4th 1-strand of the Rossmanoid fold.

A process for preparing mannose according to the invention also includes the step of enzymatically converting glucose 6-phosphate (G6P) to the F6P, and this step is catalyzed by phosphoglucoisomerase (PGI). In other embodiments, the process for preparing mannose additionally includes the step of converting glucose 1-phosphate (G1P) to the G6P, where the step is catalyzed by phosphoglucomutase (PGM). In further embodiments, the process for preparing mannose includes the conversion of G6P to F6P to M6P, where this step is catalyzed by bifunctional phosphoglucose/phosphomannose isomerase (PGPMI). In yet further embodiments, mannose production process also includes the step of converting a saccharide to the G1P that is catalyzed at least one enzyme.

Processes of the invention for the production of mannose use PGPMIs that convert G6P or F6P to M6P. Examples of PGPMIs include, but are not limited to the following proteins: Uniprot ID D7CPH7, with the amino acid sequence set forth in SEQ ID NO: 15; A0A085L170, with the amino acid sequence set forth in SEQ ID NO: 16; and M1E6Z3, with the amino acid sequence set forth in SEQ ID NO: 17. Uniprot IDs A0A085L170 and M1E6Z3 both catalyze the PGPMI reaction and share 28% amino acid sequence identity. Therefore, examples of PGPMIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

PGPMI suitable for use in the process to convert G6P or F6P to M6P contain two Rossmanoid folds. A PGPMI was structurally characterized in the art (Swan et al. A Novel Phosphoglucose Isomerase (PGI)/Phosphomannose Isomerase from the Crenarchaeon *Pyrobaculum aerophilum* Is a Member of the PGI Superfamily. J. Biol. Chem. 2004: 279; 39838-39845) and shares conserved residues with the thermophilic PGPMIs described in the invention. In some aspects of the invention the isomerase contains but is not limited to containing a GGS motif (PDB 1TZB residues 46-48) where the Gly residues assist in substrate binding and the Ser residue binds phosphate; additionally but not limited to containing a SYSG-X-T-X-ET-Hydrophobic motif (PDB 1TZB residues 87-96) that binds phosphate; additionally but not limited to containing an Arg residue (PDB 1TZB residue 135) that stabilizes high energy intermediates during catalysis; additionally but not limited to containing an EN signature (PDB 1TZB residues 203-204) where the Glu is essential for active-site base proton transfer; additionally but not limited to containing an HN signature (PDB 1TZB residues 219-220) where the His is important for ring opening/ closure of the substrate during catalysis; and additionally but not limited to containing a conserved Lys residue (PDB 1TZB residue 298) that is important for ring opening/closure of the substrate during catalysis. The conserved residues' functions are verified in a separate publication (Hansen et al. Bifunctional Phosphoglucose/Phosphomannose Isomerases from the Archaea *Aeropyrum pernix* and *Thermoplasma acidophilum* Constitute a Novel Enzyme Family within the Phosphoglucose Isomerase Superfamily. J Biol. Chem. 2004; 279; 2262-2272). An PGPMI preferably contains all of these conserved residues.

Figure 2:
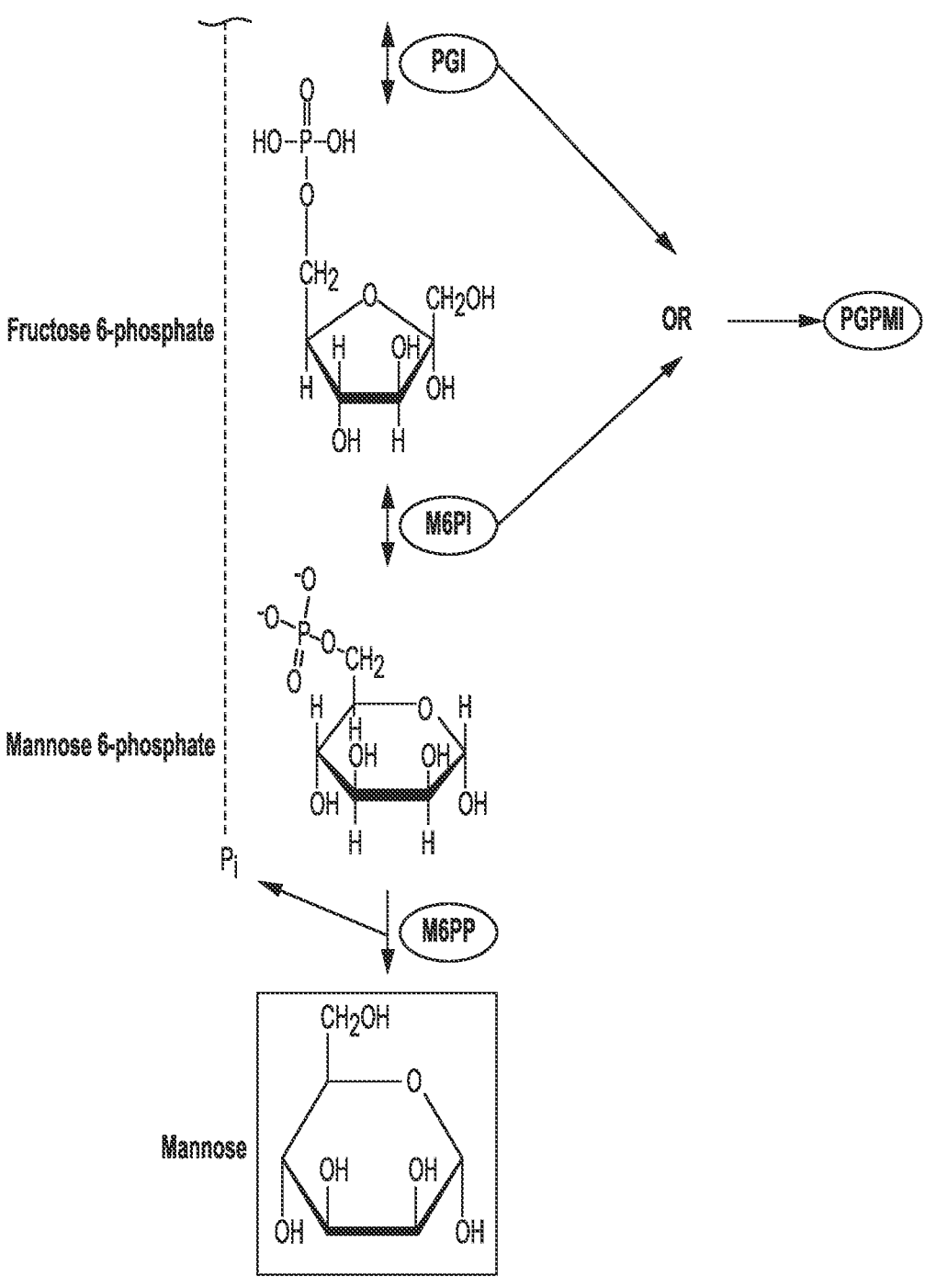
FIG. 2 is a schematic diagram showing an enzymatic pathway converting starch or its derived products to mannose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; PGPMI, bifunctional phosphoglucose/phosphomannose isomerase; M6PI, mannose 6-phosphate isomerase; M6PP, mannose 6-phosphate phosphatase.

Therefore, a process for preparing mannose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to M6P via mannose 6-phosphate isomerase (M6PI, EC 5.3.1.8), (v) converting G6P to M6P via bifunctional phosphoglucose/phosphomannose isomerase (PGPMI, EC 5.3.1.8 and 5.3.1.9), and (vi) converting M6P to mannose via M6PP. An example of the process where the saccharide is starch is shown in FIG. 2.

Typically, the ratios of enzyme units used in the disclosed process are 1:1:1:1:1 (αGP:PGM:PGI:M6PI:M6PP) or 1:1: 1:1 (αGP:PGM:PGPMI:M6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:3 can be used to further increase the reaction rate. Therefore, the enzyme ratios, including other optional enzymes discussed below, can be varied to increase the efficiency of mannose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of M6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the mannose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the M6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making mannose involves an energetically favorable reaction.

Mannose can also be produced from fructose. For example, the process involves generating F6P from fructose and polyphosphate catalyzed by polyphosphate fructokinase (PPFK); converting F6P to M6P catalyzed by M6PI; and converting M6P to mannose catalyzed by M6PP. The fructose can be produced, for example, by an enzymatic conversion of sucrose.

Mannose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to M6P catalyzed by M6PI; and converting M6P to mannose catalyzed by M6PP. In the above steps, the conversion of G6P to F6P to M6P can alternatively be catalyzed by PGPMI.

The phosphate ions generated when M6P is converted to mannose can then be recycled in the step of converting sucrose to G1P. Additionally, PPFK and polyphosphate can be used to increase mannose yields by producing F6P from fructose generated by the phosphorolytic cleavage of sucrose by SP.

In some embodiments, a process for preparing mannose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to mannose. In certain embodiments, artificial (non-natural) ATP-free enzymatic pathways are provided to convert starch, cellulose, sucrose, and their derived products to mannose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to mannose and increased solubility.

Maltose phosphorylase (MP) can be used to increase mannose yields by phosphorolytically cleaving the degradation product maltose into G1P and glucose. Alternatively, 4-glucan transferase (4GT) can be used to increase mannose yields by recycling the degradation products glucose, maltose, and maltotriose into longer maltooligosaccharides; which can be phosphorolytically cleaved by αGP to yield G1P.

In certain embodiments, cellulose and its derived products can be converted to mannose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to M6P catalyzed by M6PI; and converting M6P to mannose catalyzed by M6PP. Alternatively, in the previous pathway the conversion of G6P to F6P to M6P can be catalyzed by PGPMI. In this process, the phosphate ions can be recycled by the step of converting cellodextrin and cellobiose to G1P.

In some embodiments, polyphosphate and polyphosphate glucokinase (PPGK) can be added to the process, thus increasing yields of mannose by phosphorylating the degradation product glucose to G6P.

In other embodiments, mannose can be generated from glucose. The process involves the steps of generating G6P from glucose and polyphosphate catalyzed by polyphosphate glucokinase (PPGK); converting G6P to F6P catalyzed by PGI; converting F6P to M6P catalyzed by M6PI; and converting M6P to mannose catalyzed by M6PP. Alternatively, the conversion of G6P to F6P to M6P can be catalyzed by PGPMI.

Processes of the invention use low-cost starting materials and reduce production costs by decreasing costs associated with the feedstock and product separation. Starch, cellulose, sucrose and some of their derivatives are less expensive feedstocks than, for example, fructose. When mannose is produced from fructose, yields are lower than in the present invention, and mannose must be separated from fructose via chromatography, which leads to higher production costs.

Also, the step of converting M6P to mannose according to the invention is an irreversible phosphatase reaction, regardless of the feedstock. Therefore, mannose is produced with a very high yield while effectively minimizing the subsequent product separation costs.

In contrast to cell-based manufacturing methods, the invention involves a cell-free preparation of mannose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is mannose produced by the processes described herein for producing mannose.

Mannose produced by processes described herein may be used, as discussed above, in a variety of applications in the pharmaceutical, cosmetic, beverage, food product, dairy, confectionery, and livestock industries.

Additionally, mannose produced by the processes disclosed herein may be converted to mannitol through hydrogenation. The catalytic hydrogenation of mannose occurs with a stoichiometric yield and gives mannitol. U.S. Pat. No. 5,466,795. Mannitol is widely used in the manufacture of sugar-free chewing gum, sweets and pharmaceutical excipients. However, the production of high-purity mannose is extremely difficult to achieve and is costly. Id. Accordingly, mannose produced by the aforementioned processes can be converted to mannitol via catalytic hydrogenation.

Galactose

One embodiment of the invention is a process for preparing galactose which includes converting fructose 6-phosphate (F6P) to tagatose 6-phosphate (T6P) catalyzed by fructose 6-phosphate 4-epimerase (F6PE), converting T6P to galactose 6-phosphate (Gal6P) catalyzed by galactose 6-phosphate isomerase (Gal6PI), and converting the Gal6P produced to galactose catalyzed by galactose 6-phosphate phosphatase (Gal6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to any of the aforementioned Uniprot IDs.

Gal6PI exists as a multimer of two subunits, LacA and LacB. Examples of Gal6PIs include, but are not limited to the following protein (LacA/LacB) subunit pair: Uniprot ID P23494/P23495, with the amino acid sequences set forth in SEQ ID NO: 18/SEQ ID NO: 19. Examples of Gal6PIs also include any homologues having at least 25%, preferably at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID for LacA subunit and homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID for LacB subunit.

Gal6PIs suitable for use in the process to convert T6P to Gal6P contain a heterodimer ('A' and 'B') consisting of subunits with Rossmann-like αβα sandwich folds. Conserved residues are discussed in the art (Jung et al. Crystal Structure and Substrate Specificity of D-Galactose-6-Phosphate Isomerase Complexed with Substrates. PLOS ONE. 2013; 8; e72902). In some aspects of the invention the isomerase heterodimer contains but is not limited to containing Arg130 and Arg134 in 'A' and His9 and Arg39 in 'B' to bind the substrate's phosphate group; additionally but not limited to containing His96 in 'A' for ring opening of substrate; additionally but not limited to containing Asn97 in 'A' to stabilize high energy intermediates; and additionally but limited to containing Cys65 and Thr67 of 'B' to participate in proton transfer.

Examples of Gal6PPs include, but are not limited to Uniprot ID Q8A2F3 with the amino acid sequence set forth in SEQ ID NO: 20. Examples of Gal6PPs also include any homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID.

Preferably, a Gal6PP to convert Gal6P to galactose contains a Rossmanoid fold domain for catalysis, a C2 capping domain, D×D signature in the 1st β-strand of the Rossmanoid fold, a Thr or Ser at the end of the 2nd β-strand of the Rossmanoid fold, and a GDxxxD signature at the end of the 4th 1-strand of the Rossmanoid fold.

A process for preparing galactose according to the invention also includes the step of enzymatically converting glucose 6-phosphate (G6P) to the F6P, and this step is catalyzed by phosphoglucoisomerase (PGI). In other embodiments, the process for preparing galactose additionally includes the step of converting glucose 1-phosphate (G1P) to the G6P, where the step is catalyzed by phosphoglucomutase (PGM). In yet further embodiments, galactose production process also includes the step of converting a saccharide to the G1P that is catalyzed at least one enzyme.

Figure 3:
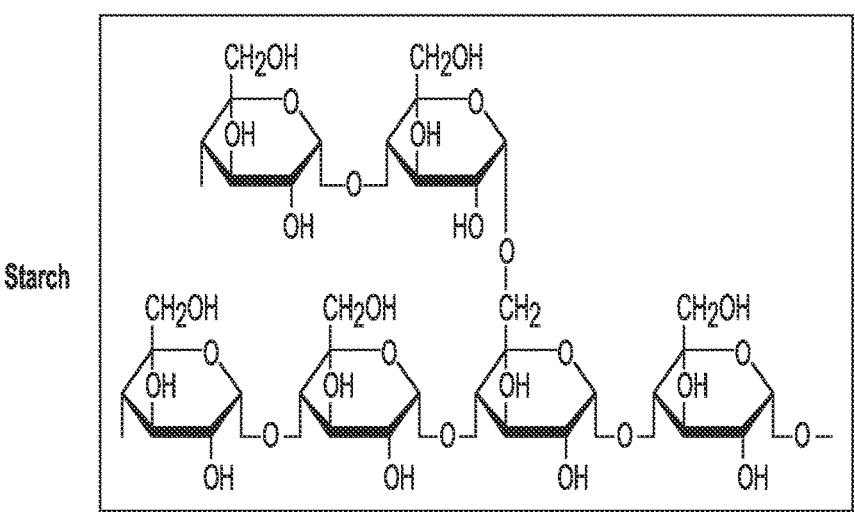
FIG. 3 is a schematic diagram showing an enzymatic pathway converting starch or its derived products to galactose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate isomerase; Gal6PI, galactose 6-phosphate isomerase; Gal6PP, galactose 6-phosphate phosphatase.
Figure 3:
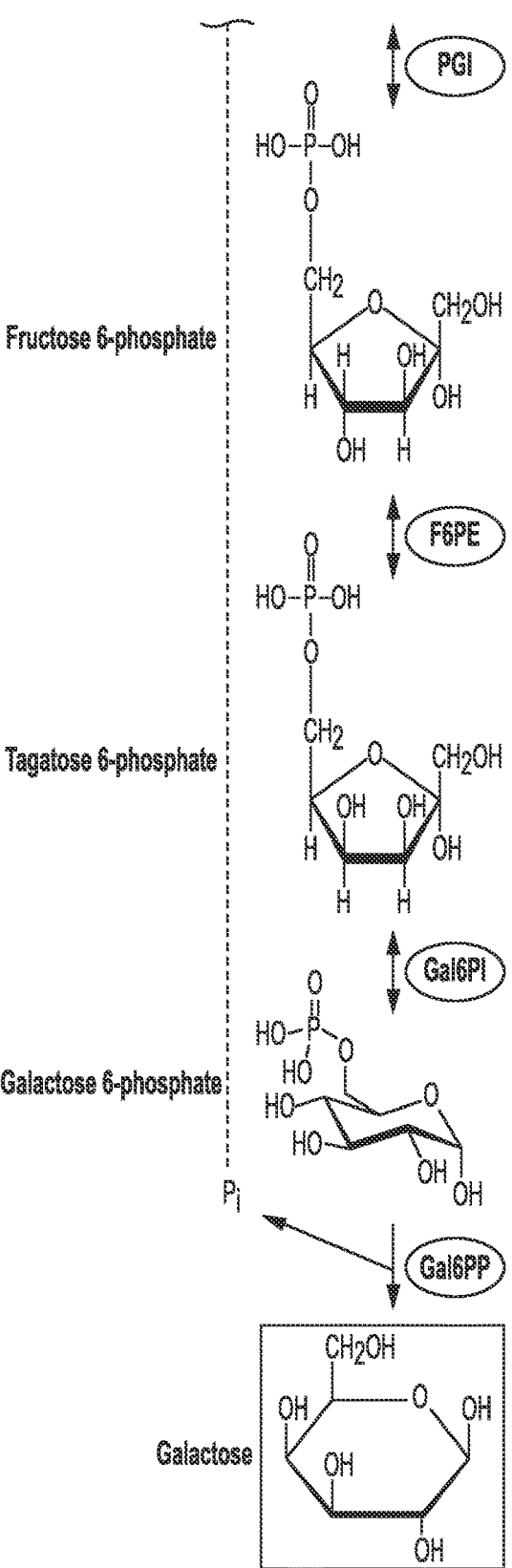
Figure 4:
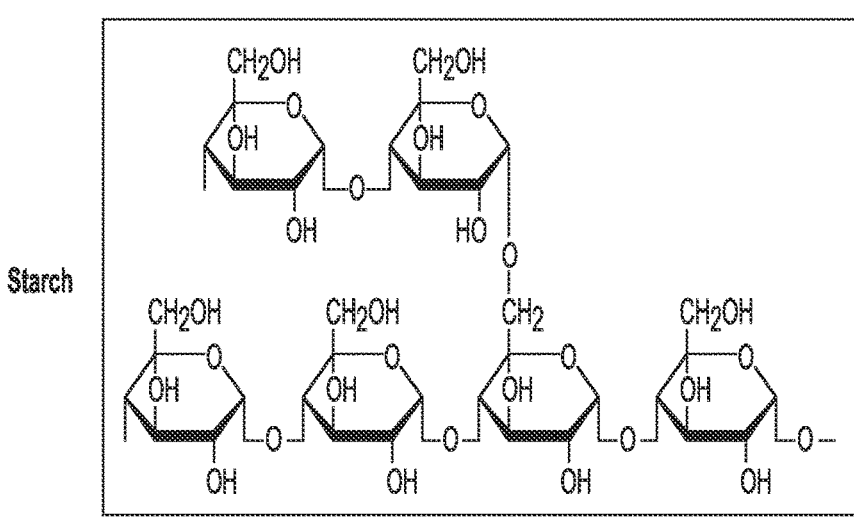
FIG. 4 is a schematic diagram showing an enzymatic pathway converting starch or its derived products to fructose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PP, fructose 6-phosphate phosphatase.
Figure 4:
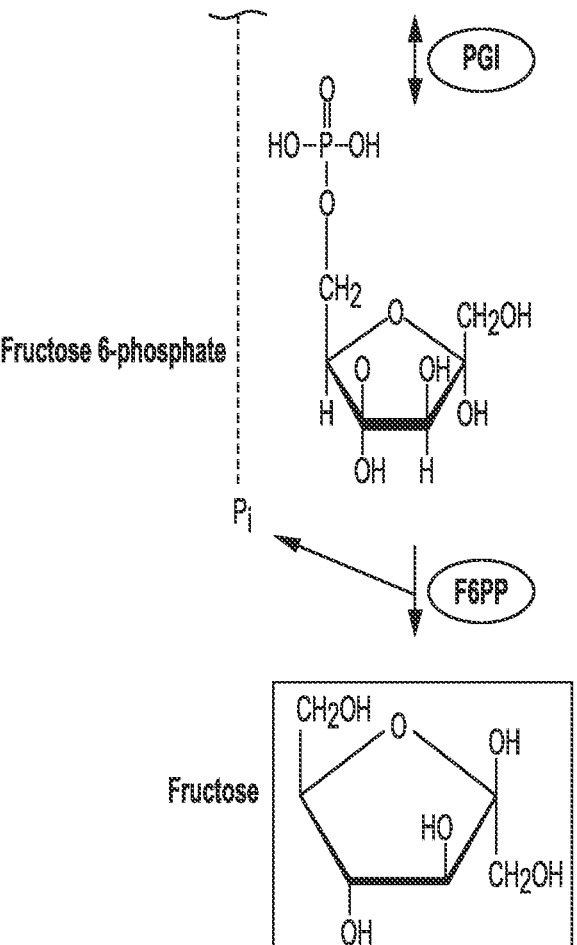

Therefore, a process for preparing galactose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to Gal6P via Gal6PI (EC 5.3.1.26), and (vi) converting Gal6P to galactose via Gal6PP. An example of the process where the saccharide is starch is shown in FIG. 3.

Typically, the ratios of enzyme units used in the disclosed process are 1:1:1:1:1:1 (αGP:PGM:PGI:F6PE:Gal6PI: Gal6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of galactose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of Gal6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the galactose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the Gal6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making galactose involves an energetically favorable reaction.

Galactose can also be produced from fructose. For example, the process involves generating F6P from fructose and polyphosphate catalyzed by polyphosphate fructokinase (PPFK); converting F6P to T6P catalyzed by F6PE; converting T6P to Gal6P catalyzed by Gal6PI, and converting Gal6P to galactose catalyzed by Gal6PP. The fructose can be produced, for example, by an enzymatic conversion of sucrose.

Galactose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to Gal6P catalyzed by Gal6PI, and converting Gal6P to galactose catalyzed by Gal6PP.

The phosphate ions generated when Gal6P is converted to galactose can then be recycled in the step of converting sucrose to G1P. Additionally, PPFK and polyphosphate can be used to increase galactose yields by producing F6P from fructose generated by the phosphorolytic cleavage of sucrose by SP.

In some embodiments, a process for preparing galactose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to galactose. In certain embodiments, artificial (non-natural) ATP-free enzymatic pathways are provided to convert starch, cellulose, sucrose, and their derived products to galactose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to galactose and increased solubility.

Maltose phosphorylase (MP) can be used to increase galactose yields by phosphorolytically cleaving the degradation product maltose into G1P and glucose. Alternatively, 4-glucan transferase (4GT) can be used to increase galactose yields by recycling the degradation products glucose, maltose, and maltotriose into longer maltooligosaccharides; which can be phosphorolytically cleaved by αGP to yield G1P.

In certain embodiments, cellulose and its derived products can be converted to galactose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to Gal6P catalyzed by Gal6PI, and converting Gal6P to galactose catalyzed by Gal6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of galactose by phosphorylating the degradation product glucose to G6P.

In other embodiments, galactose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to Gal6P catalyzed by Gal6PI; and converting Gal6P to galactose catalyzed by Gal6PP.

Processes of the invention use low-cost starting materials and reduce production costs by decreasing costs associated with the feedstock and product separation. Starch, cellulose, sucrose and some of their derivatives are less expensive feedstocks than, for example, lactose. When galactose is produced from biomass or lactose, yields are lower than in the present invention, and galactose must be separated from other sugars via chromatography, which leads to higher production costs. Furthermore, our process is animal-free.

The step of converting Gal6P to galactose according to the invention is an irreversible phosphatase reaction, regardless of the feedstock. Therefore, galactose is produced with a very high yield while effectively minimizing the subsequent product separation costs.

In contrast to cell-based manufacturing methods, the invention involves a cell-free preparation of galactose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is galactose produced by the processes described herein for producing galactose.

Fructose

One embodiment of the invention is a process for preparing fructose which includes converting fructose 6-phosphate (F6P) to fructose catalyzed by fructose 6-phosphate phosphatase (F6PP).

A non-limiting example of an F6PP is Uniprot ID B8CWV3, with the amino acid sequence set forth in SEQ ID NO: 21. Examples of F6PPs also include any homologues having at least 25%, at least 30%, more preferably at least 35%, more preferably at least 40%, more preferably at least 45%, more preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, at least 91%, at least 92%, at least 93%, or at least 94%, and even most preferably at least 96, 97, 98, 99 or 100% amino acid sequence identity to the aforementioned Uniprot ID.

Preferably, a F6PP to convert F6P to fructose contains a Rossmanoid fold domain for catalysis, a C1 capping domain, D×D signature in the 1st β-strand of the Rossmanoid fold, a Thr or Ser at the end of the 2nd β-strand of the Rossmanoid fold, a Lys at the N-terminus of the α-helix C-terminal to the 3rd 1-strand of the Rossmanoid fold, and a ED signature at the end of the 4th β-strand of the Rossmanoid fold.

A process for preparing fructose according to the invention also includes the step of enzymatically converting glucose 6-phosphate (G6P) to the F6P, and this step is catalyzed by phosphoglucoisomerase (PGI). In other embodiments, the process for preparing fructose additionally includes the step of converting glucose 1-phosphate (G1P) to the G6P, where the step is catalyzed by phosphoglucomutase (PGM). In yet further embodiments, fructose production process also includes the step of converting a saccharide to the G1P that is catalyzed at least one enzyme.

Therefore, a process for preparing fructose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to fructose using F6PP.

Typically, the ratios of enzyme units used in the disclosed process are 1:1:1:1 (αGP:PGM:PGI:F6PP). To optimize product yields, these ratios can be adjusted in any number of combinations. For example, a ratio of 3:1:1:1 can be used to maximize the concentration of phosphorylated intermediates, which will result in increased activity of the downstream reactions. Conversely, a ratio of 1:1:1:3 can be used to maintain a robust supply of phosphate for αGP, which will result in more efficient phosphorolytic cleavage of alpha-1, 4-glycosidic bonds. A ratio of enzymes, for example, 3:1:1:3 can be used to further increase the reaction rate. Therefore, the enzyme ratios, including other optional enzymes discussed below, can be varied to increase the efficiency of fructose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of F6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the fructose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the F6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making fructose involves an energetically favorable reaction.

Figure 5:
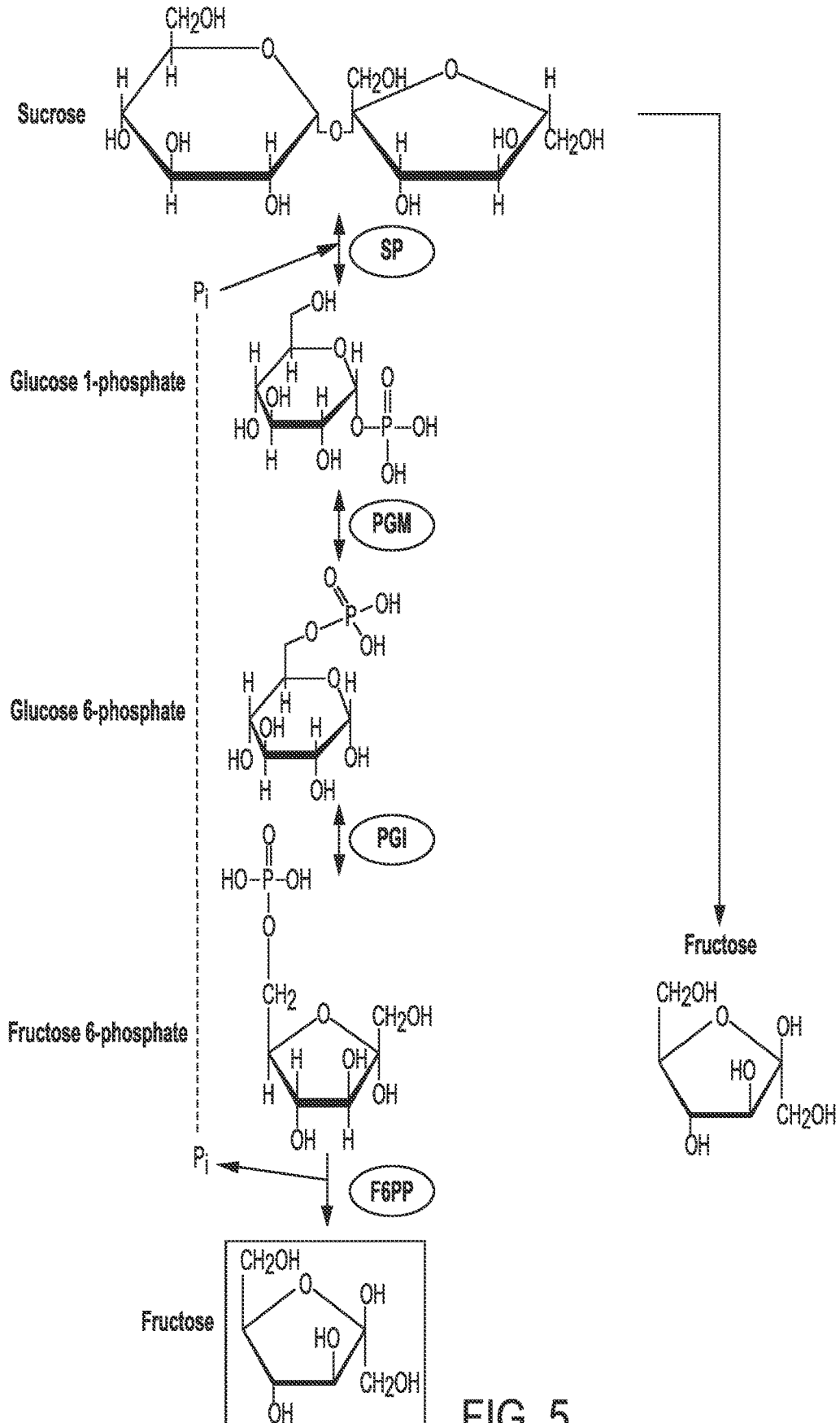
FIG. 5 is a schematic diagram showing an enzymatic pathway converting sucrose to fructose. The following abbreviations are used: SP, sucrose phosphorylase; PGM, phosphoglucomutase; PGI, phosphoglucoisomerase; F6PP, fructose 6-phosphate phosphatase.
Figure 6:
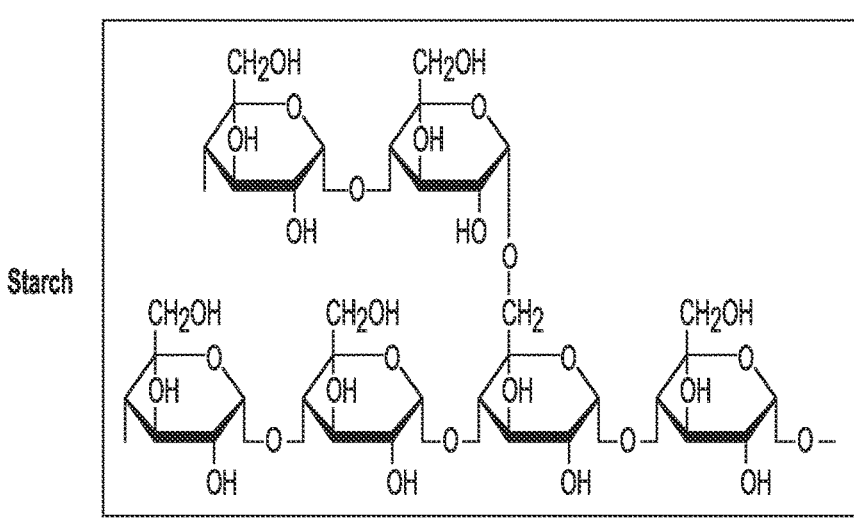
FIG. 6 is a schematic diagram showing an enzymatic pathway converting starch or its derived products to altrose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; P6PE, psicose 6-phosphate epimerase; Alt6PI, altrose 6-phosphate isomerase; Alt6PP, altrose 6-phosphate phosphatase.
Figure 7:
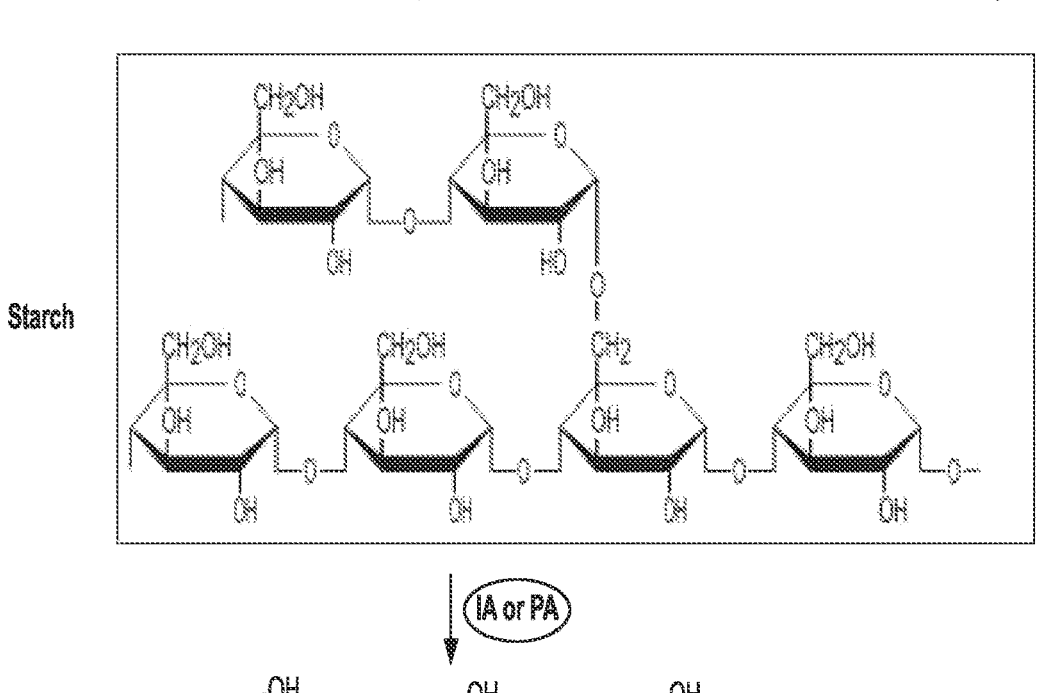
FIG. 7 is a schematic diagram showing an enzymatic pathway converting starch or its derived products to talose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; Tal6PI, talose 6-phosphate isomerase; Tal6PP, talose 6-phosphate phosphatase.
Figure 7:
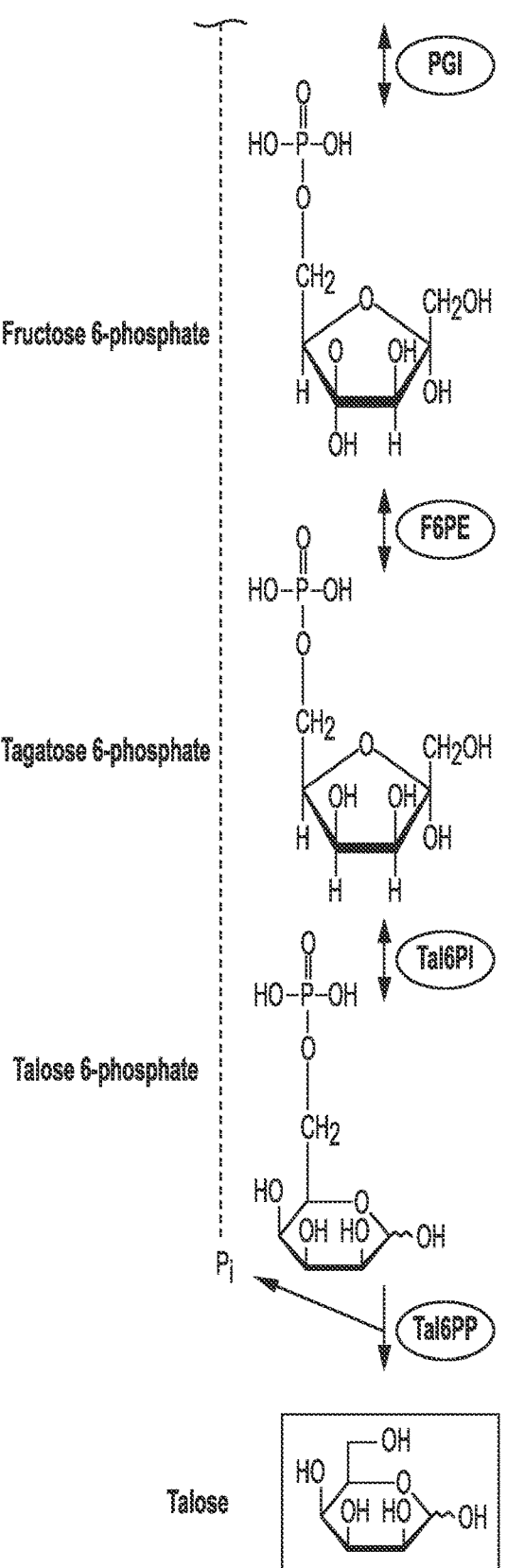
Figure 8:
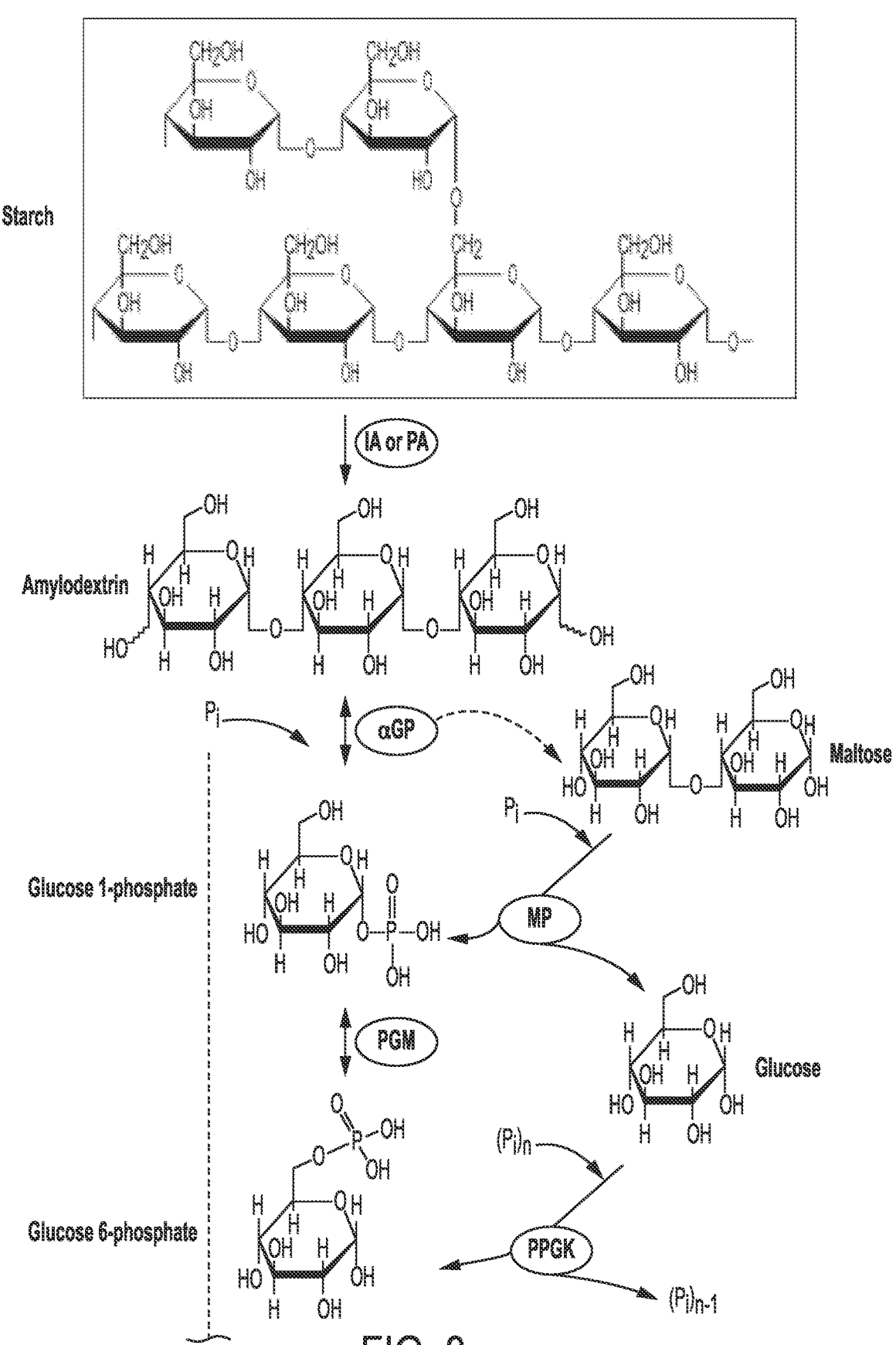
FIG. 8 is a schematic diagram showing an enzymatic pathway converting starch or its derived products to sorbose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; S6PP, sorbose 6-phosphate phosphatase.
Figure 8:
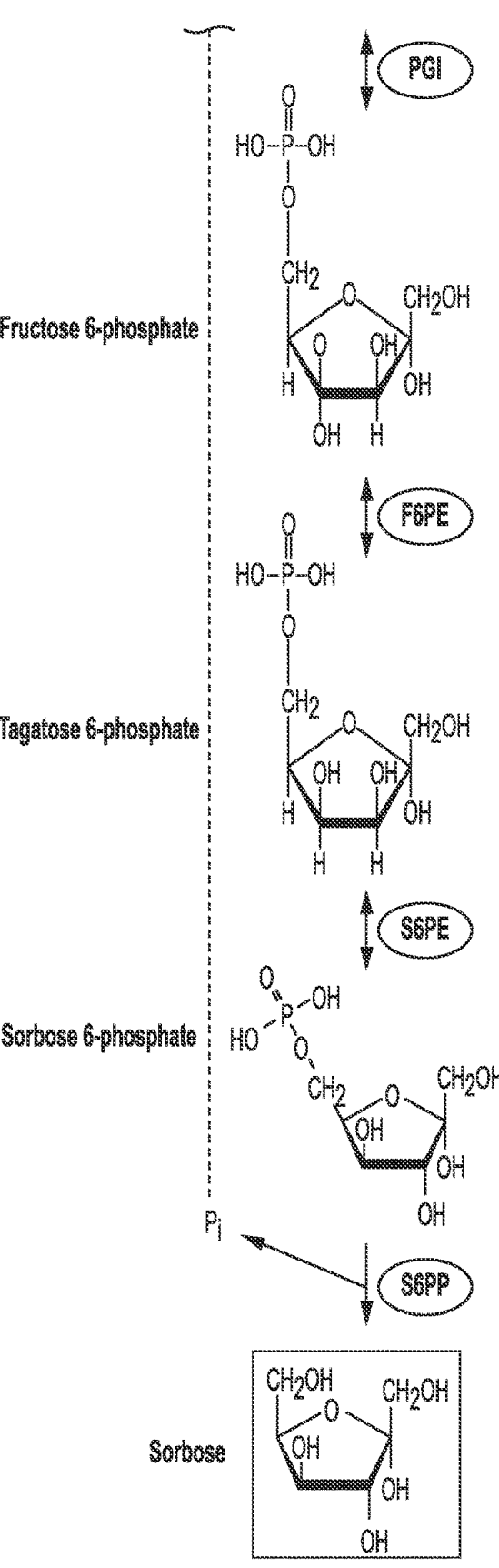
Figure 9:
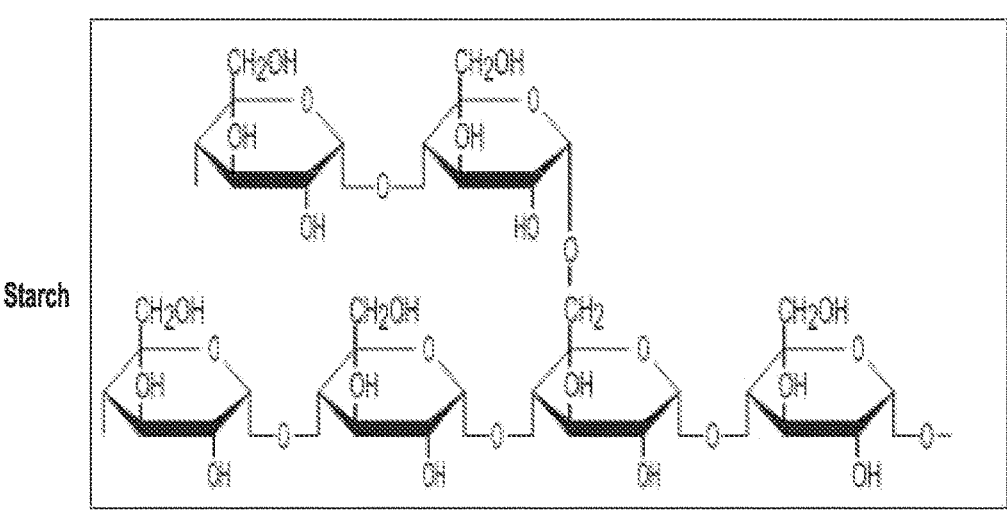
FIG. 9 is a schematic diagram showing an enzymatic pathway converting starch or its derived products to gulose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; Gul6PI, gulose 6-phosphate isomerase; Gul6PP, gulose 6-phosphate phosphatase.
Figure 9:
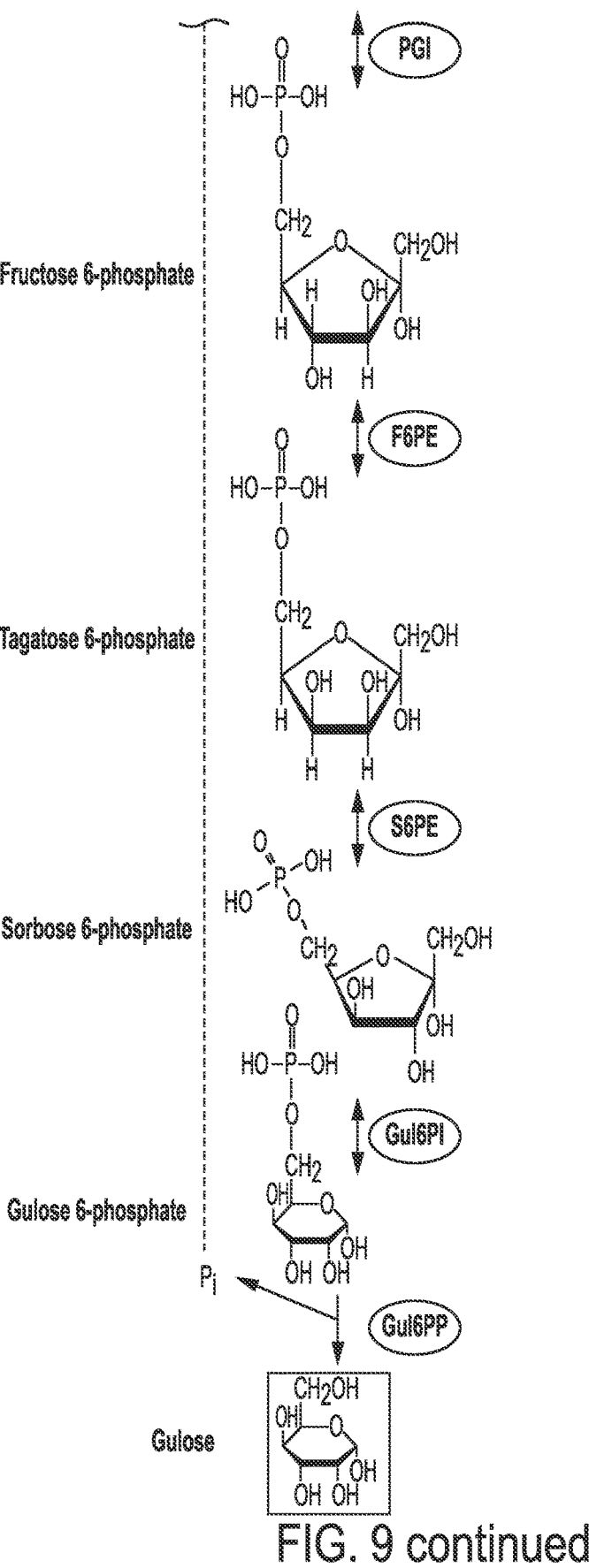
Figure 10:
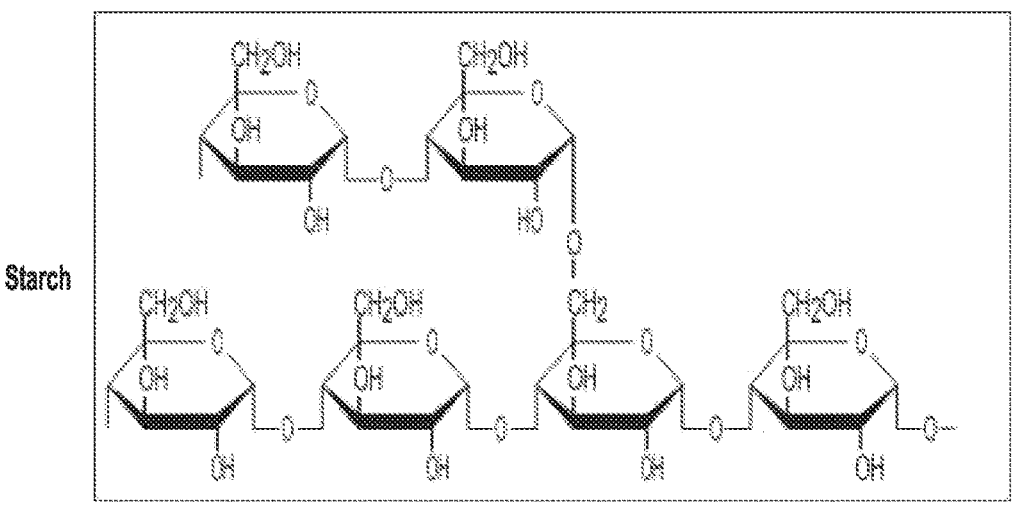
FIG. 10 is a schematic diagram showing an enzymatic pathway converting starch or its derived products to idose. The following abbreviations are used: IA, isoamylase; PA, pullulanase; αGP, alpha-glucan phosphorylase or starch phosphorylase; MP, maltose phosphorylase; PGM, phosphoglucomutase; PPGK, polyphosphate glucokinase; PGI, phosphoglucoisomerase; F6PE, fructose 6-phosphate epimerase; S6PE, sorbose 6-phosphate epimerase; I6PI, idose 6-phosphate isomerase; I6PP, idose 6-phosphate phosphatase.
Figure 10:
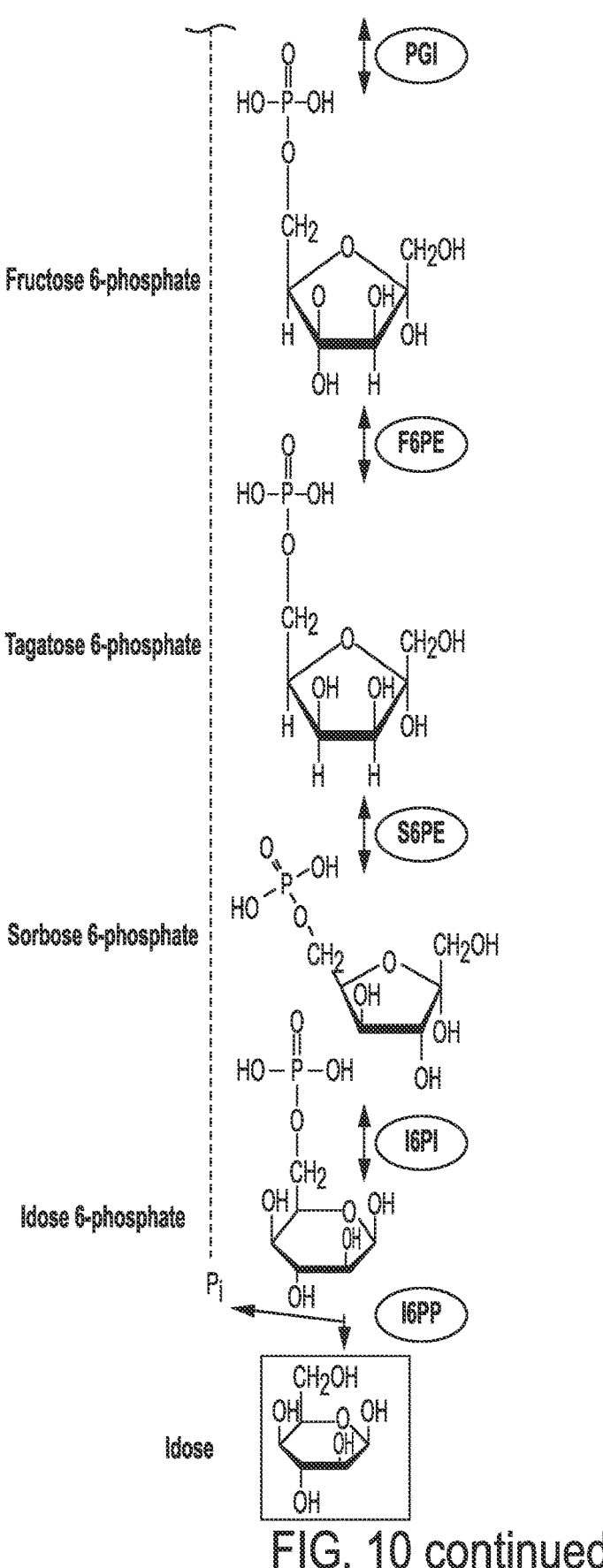

Fructose can also be produced from sucrose via an F6P intermediate. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; F6P to fructose catalyzed by F6PP. An example enzymatic pathway is provided in FIG. 5

The phosphate ions generated when F6P is converted to fructose can then be recycled in the step of converting sucrose to G1P. Additionally, PPFK and polyphosphate can be used to increase fructose yields by producing F6P from fructose generated by the phosphorolytic cleavage of sucrose by SP.

In some embodiments, a process for preparing fructose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to fructose. In certain embodiments, artificial (non-natural) ATP-free enzymatic pathways are provided to convert starch, cellulose, sucrose, and their derived products to fructose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to fructose and increased solubility.

Maltose phosphorylase (MP) can be used to increase fructose yields by phosphorolytically cleaving the degradation product maltose into G1P and glucose. Alternatively, 4-glucan transferase (4GT) can be used to increase fructose yields by recycling the degradation products glucose, maltose, and maltotriose into longer maltooligosaccharides; which can be phosphorolytically cleaved by αGP to yield G1P.

In certain embodiments, cellulose and its derived products can be converted to fructose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to fructose catalyzed by F6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of fructose by phosphorylating the degradation product glucose to G6P.

In other embodiments, fructose can be generated from glucose. The process involves the steps of generating G6P from glucose and polyphosphate catalyzed by polyphosphate glucokinase (PPGK); converting G6P to F6P catalyzed by PGI; converting F6P to fructose catalyzed by F6PP.

Processes of the invention use low-cost starting materials and reduce production costs by decreasing costs associated with the feedstock and product separation. Starch, cellulose, sucrose and some of their derivatives are less expensive feedstocks than, for example, lactose. When fructose is produced from biomass or lactose, yields are lower than in the present invention, and fructose must be separated from other sugars via chromatography, which leads to higher production costs. Furthermore, our process is animal-free.

The step of converting F6P to fructose according to the invention is an irreversible phosphatase reaction, regardless of the feedstock. Therefore, fructose is produced with a very high yield while effectively minimizing the subsequent product separation costs.

In contrast to cell-based manufacturing methods, the invention involves a cell-free preparation of fructose, has relatively high reaction rates due to the elimination of the cell membrane, which often slows down the transport of substrate/product into and out of the cell. It also has a final product free of nutrient-rich fermentation media/cellular metabolites.

Ar particular embodiment of the invention is fructose produced by the processes described herein for producing fructose.

Altrose

One embodiment of the invention is a process for preparing altrose which includes converting fructose 6-phosphate (F6P) to psicose 6-phosphate (P6P) catalyzed by psicose 6-phosphate 3-epimerase (P6PE), converting P6P to altrose 6-phosphate (Alt6P) catalyzed by altrose 6-phosphate isomerase (Alt6PI), and converting the Alt6P produced to altrose catalyzed by altrose 6-phosphate phosphatase.

A process for preparing altrose according to the invention also includes the step of enzymatically converting glucose 6-phosphate (G6P) to the F6P, and this step is catalyzed by phosphoglucoisomerase (PGI). In other embodiments, the process for preparing altrose additionally includes the step of converting glucose 1-phosphate (G1P) to the G6P, where the step is catalyzed by phosphoglucomutase (PGM). In yet further embodiments, altrose production process also includes the step of converting a saccharide to the G1P that is catalyzed at least one enzyme.

Therefore, a process for preparing altrose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to P6P via P6PE, (v) converting P6P to Alt6P via Alt6PI, and (vi) converting Alt6P to altrose via Alt6PP. An example of the enzymatic process where the saccharide is starch is shown in FIG. 1.

Typically, the ratios of enzyme units used in the disclosed process are 1:1:1:1:1:1 (αGP:PGM:PGI:P6PE:Alt6PI:Alt6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of altrose production. For example, a particular enzyme may be present in an amount about 2x, 3x, 4x, 5x, etc. relative to the amount of other enzymes.

Phosphate ions produced by dephosphorylation of Alt6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the altrose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concentration results in decreased production costs due to low total phosphate and thus lowered cost of phosphate removal. It also prevents inhibition of the Alt6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making altrose involves an energetically favorable reaction.

Altrose can also be produced from fructose. For example, the process involves generating F6P from fructose and polyphosphate catalyzed by polyphosphate fructokinase (PPFK); converting F6P to P6P catalyzed by P6PE; converting P6P to Alt6P catalyzed by Alt6PI, and converting Alt6P to altrose catalyzed by Alt6PP. The fructose can be produced, for example, by an enzymatic conversion of sucrose.

Altrose can also be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to P6P catalyzed by P6PE; converting P6P to Alt6P catalyzed by Alt6PI, and converting Alt6P to altrose catalyzed by Alt6PP.

The phosphate ions generated when Alt6P is converted to altrose can then be recycled in the step of converting sucrose to G1P. Additionally, PPFK and polyphosphate can be used to increase altrose yields by producing F6P from fructose generated by the phosphorolytic cleavage of sucrose by SP.

In certain embodiments, a process for preparing altrose includes the following steps: generating glucose from poly-saccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

Several enzymes can be used to hydrolyze starch to increase the G1P yield. Such enzymes include isoamylase, pullulanase, and alpha-amylase. Corn starch contains many branches that impede $\alpha$GP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to altrose and increased solubility.

Maltose phosphorylase (MP) can be used to increase altrose yields by phosphorolytically cleaving the degradation product maltose into G1P and glucose. Alternatively, 4-glucan transferase (4GT) can be used to increase altrose yields by recycling the degradation products glucose, maltose, and maltotriose into longer maltooligosaccharides; which can be phosphorolytically cleaved by $\alpha$GP to yield G1P.

In certain embodiments, cellulose and its derived products can be converted to altrose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to P6P catalyzed by P6PE; converting P6P to Alt6P catalyzed by Alt6PI, and converting Alt6P to altrose catalyzed by Alt6PP. In this process, the phosphate ions can be recycled by the step of converting cellodextrin and cellobiose to G1P.

Several enzymes may be used to hydrolyze solid cellulose to water-soluble cellodextrins and cellobiose. Such enzymes include endoglucanase and cellobiohydrolase, but not including beta-glucosidase (cellobiase).

In some embodiments, polyphosphate and polyphosphate glucokinase (PPGK) can be added to the process, thus increasing yields of altrose by phosphorylating the degradation product glucose to G6P.

Altrose can be produced from glucose. The process involves the steps of generating G6P from glucose and polyphosphate catalyzed by polyphosphate glucokinase (PPGK); converting G6P to F6P catalyzed by PGI; converting F6P to P6P catalyzed by P6PE; converting P6P to Alt6P catalyzed by A6PI; and converting Alt6P to altrose catalyzed by Alt6PP.

Processes of the invention for making altrose use low-cost starting materials and reduce production costs by decreasing costs associated with the feedstock and product separation. Starch, cellulose, sucrose and some of their derivatives are less expensive feedstocks than, for example, fructose. When altrose is produced from psiose, yields are lower than in the present invention, and altrose must be separated from psi-cose via chromatography, which leads to higher production costs.

Also, the step of converting Alt6P to altrose according to the invention is an irreversible phosphatase reaction, regardless of the feedstock. Therefore, altrose is produced with a very high yield while effectively minimizing the subsequent product separation costs.

In contrast to cell-based manufacturing methods, the invention involves a cell-free preparation of altrose, has relatively high reaction rates due to the elimination of the cell membrane, which often slows down the transport of substrate/product into and out of the cell. It also has a final product free of nutrient-rich fermentation media/cellular metabolites.

Ar particular embodiment of the invention is altrose produced by the processes described herein for producing altrose.

Talose

One embodiment of the invention is a process for preparing talose which includes converting fructose 6-phosphate (F6P) to tagatose 6-phosphate (T6P) catalyzed by fructose 6-phosphate 4-epimerase (F6PE), converting T6P to talose 6-phosphate (Tal6P) catalyzed by talose 6-phosphate isomerase (Tal6PI), and converting the Tal6P produced to talose catalyzed by talose 6-phosphate phosphatase (Tal6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing talose according to the invention also includes the step of enzymatically converting glucose 6-phosphate (G6P) to the F6P, and this step is catalyzed by phosphoglucoisomerase (PGI). In other embodiments, the process for preparing talose additionally includes the step of converting glucose 1-phosphate (G1P) to the G6P, where the step is catalyzed by phosphoglucomutase (PGM). In yet further embodiments, talose production process also includes the step of converting a saccharide to the G1P that is catalyzed at least one enzyme.

Therefore, a process for preparing talose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to Tal6P via Tal6PI (EC 5.3.1.26), and (vi) converting Tal6P to talose via Tal6PP. An example of the process where the saccharide is starch is shown in FIG. 3.

Typically, the ratios of enzyme units used in the disclosed process are 1:1:1:1:1:1 (αGP:PGM:PGI:F6PE:Tal6PI: Tal6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of talose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of Tal6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the talose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the Tal6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making talose involves an energetically favorable reaction.

Talose can also be produced from fructose. For example, the process involves generating F6P from fructose and polyphosphate catalyzed by polyphosphate fructokinase (PPFK); converting F6P to T6P catalyzed by F6PE; converting T6P to Tal6P catalyzed by Tal6PI, and converting Tal6P to talose catalyzed by Tal6PP. The fructose can be produced, for example, by an enzymatic conversion of sucrose.

Talose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to Tal6P catalyzed by Tal6PI, and converting Tal6P to talose catalyzed by Tal6PP.

The phosphate ions generated when Tal6P is converted to talose can then be recycled in the step of converting sucrose to G1P. Additionally, PPFK and polyphosphate can be used to increase talose yields by producing F6P from fructose generated by the phosphorolytic cleavage of sucrose by SP.

In some embodiments, a process for preparing talose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to talose. In certain embodiments, artificial (non-natural) ATP-free enzymatic pathways are provided to convert starch, cellulose, sucrose, and their derived products to talose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to talose and increased solubility.

Maltose phosphorylase (MP) can be used to increase talose yields by phosphorolytically cleaving the degradation product maltose into G1P and glucose. Alternatively, 4-glucan transferase (4GT) can be used to increase talose yields by recycling the degradation products glucose, maltose, and maltotriose into longer maltooligosaccharides; which can be phosphorolytically cleaved by αGP to yield G1P.

In certain embodiments, cellulose and its derived products can be converted to talose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to Tal6P catalyzed by Tal6PI, and converting Tal6P to talose catalyzed by Tal6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of talose by phosphorylating the degradation product glucose to G6P.

In other embodiments, talose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to Tal6P catalyzed by Tal6PI; and converting Tal6P to talose catalyzed by Tal6PP.

Processes of the invention use low-cost starting materials and reduce production costs by decreasing costs associated with the feedstock and product separation. Starch, cellulose, sucrose and some of their derivatives are less expensive feedstocks than, for example, lactose. When talose is produced from biomass or lactose, yields are lower than in the present invention, and talose must be separated from other sugars via chromatography, which leads to higher production costs. Furthermore, our process is animal-free.

The step of converting Tal6P to talose according to the invention is an irreversible phosphatase reaction, regardless of the feedstock. Therefore, talose is produced with a very high yield while effectively minimizing the subsequent product separation costs.

In contrast to cell-based manufacturing methods, the invention involves a cell-free preparation of talose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is talose produced by the processes described herein for producing talose.

Sorbose

One embodiment of the invention is a process for preparing sorbose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), and converting the S6P produced to sorbose catalyzed by sorbose 6-phosphate phosphatase (S6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing sorbose according to the invention also includes the step of enzymatically converting glucose 6-phosphate (G6P) to the F6P, and this step is catalyzed by phosphoglucoisomerase (PGI). In other embodiments, the process for preparing sorbose additionally includes the step of converting glucose 1-phosphate (G1P) to the G6P, where the step is catalyzed by phosphoglucomutase (PGM). In yet further embodiments, sorbose production process also includes the step of converting a saccharide to the G1P that is catalyzed at least one enzyme.

Therefore, a process for preparing sorbose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), and (vi) converting S6P to sorbose via S6PP. An example of the process where the saccharide is starch is shown in FIG. 3.

Typically, the ratios of enzyme units used in the disclosed process are 1:1:1:1:1:1 (αGP:PGM:PGI:F6PE:S6PE:S6PP). To optimize product yields, these ratios can be adjusted in any number of combinations. For example, a ratio of 3:1:1:1:1:1 can be used to maximize the concentration of phosphorylated intermediates, which will result in increased activity of the downstream reactions. Conversely, a ratio of 1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:3 can be used to further increase the reaction rate. Therefore, the enzyme ratios, including other optional enzymes discussed below, can be varied to increase the efficiency of sorbose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the sorbose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making sorbose involves an energetically favorable reaction.

Sorbose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, and converting S6P to sorbose catalyzed by S6PP. The fructose can be produced, for example, by an enzymatic conversion of sucrose.

Sorbose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP.

The phosphate ions generated when S6P is converted to sorbose can then be recycled in the step of converting sucrose to G1P. Additionally, PPFK and polyphosphate can be used to increase sorbose yields by producing F6P from fructose generated by the phosphorolytic cleavage of sucrose by SP.

In some embodiments, a process for preparing sorbose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to sorbose. In certain embodiments, artificial (non-natural) ATP-free enzymatic pathways are provided to convert starch, cellulose, sucrose, and their derived products to sorbose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to sorbose and increased solubility.

Maltose phosphorylase (MP) can be used to increase sorbose yields by phosphorolytically cleaving the degradation product maltose into G1P and glucose. Alternatively, 4-glucan transferase (4GT) can be used to increase sorbose yields by recycling the degradation products glucose, maltose, and maltotriose into longer maltooligosaccharides; which can be phosphorolytically cleaved by αGP to yield G1P.

In certain embodiments, cellulose and its derived products can be converted to sorbose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of sorbose by phosphorylating the degradation product glucose to G6P.

In other embodiments, sorbose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; and converting S6P to sorbose catalyzed by S6PP.

Processes of the invention use low-cost starting materials and reduce production costs by decreasing costs associated with the feedstock and product separation. Starch, cellulose, sucrose and some of their derivatives are less expensive feedstocks than, for example, lactose. When sorbose is produced from biomass or lactose, yields are lower than in the present invention, and sorbose must be separated from other sugars via chromatography, which leads to higher production costs. Furthermore, our process is animal-free.

The step of converting S6P to sorbose according to the invention is an irreversible phosphatase reaction, regardless of the feedstock. Therefore, sorbose is produced with a very high yield while effectively minimizing the subsequent product separation costs.

In contrast to cell-based manufacturing methods, the invention involves a cell-free preparation of sorbose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is sorbose produced by the processes described herein for producing sorbose.

Gulose

One embodiment of the invention is a process for preparing gulose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), converting the S6P produced to gulose 6-phosphate (Gul6P) catalyzed by gulose 6-phosphate isomerase and converting the Gul6P to gulose by gulose 6-phosphate phosphatase (Gul6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing gulose according to the invention also includes the step of enzymatically converting glucose 6-phosphate (G6P) to the F6P, and this step is catalyzed by phosphoglucoisomerase (PGI). In other embodiments, the process for preparing gulose additionally includes the step of converting glucose 1-phosphate (G1P) to the G6P, where the step is catalyzed by phosphoglucomutase (PGM). In yet further embodiments, gulose production process also includes the step of converting a saccharide to the G1P that is catalyzed at least one enzyme.

Therefore, a process for preparing gulose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), (vi) converting S6P to Gul6P via Gul6PI, and (vii) converting GulP to gulose via Gul6PP.

Typically, the ratios of enzyme units used in the disclosed process are 1:1:1:1:1:1:1 (αGP:PGM:PGI:F6PE:S6PE: Gul6PI:GulPP). To optimize product yields, these ratios can be adjusted in any number of combinations. For example, a ratio of 3:1:1:1:1:1:1 can be used to maximize the concentration of phosphorylated intermediates, which will result in increased activity of the downstream reactions. Conversely, a ratio of 1:1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:1:3 can be used to further increase the reaction rate. Therefore, the enzyme ratios, including other optional enzymes discussed below, can be varied to increase the efficiency of gulose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the gulose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making gulose involves an energetically favorable reaction.

Gulose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, S6P to Gul6P by Gul6PI, and Gul6P to gulose by Gul6PP. The fructose can be produced, for example, by an enzymatic conversion of sucrose.

Gulose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, S6P to Gul6P by Gul6PI, and Gul6P to gulose by Gul6PP.

The phosphate ions generated when S6P is converted to sorbose can then be recycled in the step of converting sucrose to G1P. Additionally, PPFK and polyphosphate can be used to increase gulose yields by producing F6P from fructose generated by the phosphorolytic cleavage of sucrose by SP.

In some embodiments, a process for preparing gulose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to gulose. In certain embodiments, artificial (non-natural) ATP-free enzymatic pathways are provided to convert starch, cellulose, sucrose, and their derived products to gulose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to gulose and increased solubility.

Maltose phosphorylase (MP) can be used to increase gulose yields by phosphorolytically cleaving the degradation product maltose into G1P and glucose. Alternatively, 4-glucan transferase (4GT) can be used to increase gulose yields by recycling the degradation products glucose, maltose, and maltotriose into longer maltooligosaccharides; which can be phosphorolytically cleaved by αGP to yield G1P.

In certain embodiments, cellulose and its derived products can be converted to gulose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of gulose by phosphorylating the degradation product glucose to G6P.

In other embodiments, gulose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; S6P to Gul6P by Gul6PI, and Gul6P to gulose by Gul6PP.

Processes of the invention use low-cost starting materials and reduce production costs by decreasing costs associated with the feedstock and product separation. Starch, cellulose, sucrose and some of their derivatives are less expensive feedstocks than, for example, lactose. When gulose is produced from biomass or lactose, yields are lower than in the present invention, and gulose must be separated from other sugars via chromatography, which leads to higher production costs. Furthermore, our process is animal-free.

The step of converting S6P to gulose according to the invention is an irreversible phosphatase reaction, regardless of the feedstock. Therefore, gulose is produced with a very high yield while effectively minimizing the subsequent product separation costs.

In contrast to cell-based manufacturing methods, the invention involves a cell-free preparation of gulose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is gulose produced by the processes described herein for producing gulose.

Idose

One embodiment of the invention is a process for preparing idose which includes converting fructose 6-phosphate (F6P) to tagatose 6-phosphate (T6P) catalyzed by fructose 6-phosphate 4-epimerase (F6PE), converting T6P to sorbose 6-phosphate (S6P) catalyzed by sorbose 6-phosphate epimerase (S6PE), converting the S6P produced to idose 6-phosphate (I6P) catalyzed by idose 6-phosphate isomerase and converting the I6P to idose by idose 6-phosphate phosphatase (I6PP).

Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

A process for preparing idose according to the invention also includes the step of enzymatically converting glucose 6-phosphate (G6P) to the F6P, and this step is catalyzed by phosphoglucoisomerase (PGI). In other embodiments, the process for preparing idose additionally includes the step of converting glucose 1-phosphate (G1P) to the G6P, where the step is catalyzed by phosphoglucomutase (PGM). In yet further embodiments, idose production process also includes the step of converting a saccharide to the G1P that is catalyzed at least one enzyme.

Therefore, a process for preparing idose according to the invention can, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via F6PE, (v) converting T6P to S6P via S6PE (EC 5.3.1.26), (vi) converting S6P to I6P via I6PI, and (vii) converting I6P to idose via I6PP.

Typically, the ratios of enzyme units used in the disclosed process are 1:1:1:1:1:1:1 (αGP:PGM:PGI:F6PE:S6PE:I6PI:I6PP). To optimize product yields, these ratios can be adjusted in any number of combinations. For example, a ratio of 3:1:1:1:1:1:1 can be used to maximize the concentration of phosphorylated intermediates, which will result in increased activity of the downstream reactions. Conversely, a ratio of 1:1:1:1:1:1:3 can be used to maintain a robust supply of phosphate for αGP, which will result in more efficient phosphorolytic cleavage of alpha-1,4-glycosidic bonds. A ratio of enzymes, for example, 3:1:1:1:1:1:3 can be used to further increase the reaction rate. Therefore, the enzyme ratios, including other optional enzymes discussed below, can be varied to increase the efficiency of idose production. For example, a particular enzyme may be present in an amount about 2×, 3×, 4×, 5×, etc. relative to the amount of other enzymes.

One of the important advantages of the processes is that the process steps can be conducted in a single bioreactor or reaction vessel. Alternatively, the steps can also be conducted in a plurality of bioreactors, or reaction vessels, that are arranged in series.

Phosphate ions produced by dephosphorylation of S6P can then be recycled in the process step of converting a saccharide to G1P, particularly when all process steps are conducted in a single bioreactor or reaction vessel. The ability to recycle phosphate in the disclosed processes allows for non-stoichiometric amounts of phosphate to be used, which keeps reaction phosphate concentrations low. This affects the overall pathway and the overall rate of the processes, but does not limit the activity of the individual enzymes and allows for overall efficiency of the idose making processes.

For example, reaction phosphate concentrations can range from about 0.1 mM to about 300 mM, from about 0.1 mM to about 150 mM, from about 1 mM to about 50 mM, preferably from about 5 mM to about 50 mM, or more preferably from about 10 mM to about 50 mM. For instance, the reaction phosphate concentration can be about 0.1 mM, about 0.5 mM, about 1 mM, about 1.5 mM, about 2 mM, about 2.5 mM, about 5 mM, about 6 mM, about 7 mM, about 8 mM, about 9 mM, about 10 mM, about 15 mM, about 20 mM, about 25 mM, about 30 mM, about 35 mM, about 40 mM, about 45 mM, about 50 mM, or about 55 mM.

Therefore, low phosphate concertation results in decreased production costs due to low total phosphate and thus lowered cost of phosphate removal. It also prevents inhibition of the S6PP by high concentrations of free phosphate and decreases the potential for phosphate pollution.

Furthermore, the processes disclosed herein can be conducted without added ATP as a source of phosphate, i.e., ATP-free. The processes can also be conducted without having to add NAD(P)(H), i.e., NAD(P)(H)-free. Other advantages also include the fact that at least one step of the disclosed processes for making idose involves an energetically favorable reaction.

Idose can also be produced from fructose. For example, the process involves generating F6P from fructose and polyphosphate catalyzed by polyphosphate fructokinase (PPFK); converting F6P to T6P catalyzed by F6PE; converting T6P to S6P catalyzed by S6PE, S6P to I6P by I6PI, and I6P to idose by I6PP. The fructose can be produced, for example, by an enzymatic conversion of sucrose.

Idose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; converting T6P to S6P catalyzed by S6PE, S6P to I6P by I6PI, and I6P to idose by I6PP.

The phosphate ions generated when S6P is converted to sorbose can then be recycled in the step of converting sucrose to G1P. Additionally, PPFK and polyphosphate can be used to increase idose yields by producing F6P from fructose generated by the phosphorolytic cleavage of sucrose by SP.

In some embodiments, a process for preparing idose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to F6P catalyzed by at least one enzyme. Examples of the polysaccharides and oligosaccharides are enumerated above.

In other embodiments, G6P is produced from glucose and sodium polyphosphate by polyphosphate glucokinase.

The present disclosure provides processes for converting saccharides, such as polysaccharides and oligosaccharides in starch, cellulose, sucrose and their derived products, to idose. In certain embodiments, artificial (non-natural) ATP-free enzymatic pathways are provided to convert starch, cellulose, sucrose, and their derived products to idose using cell-free enzyme cocktails.

As shown above, several enzymes can be used to hydrolyze starch to increase the G1P yield. Such enzymes include isoamylase, pullulanase, and alpha-amylase. Corn starch contains many branches that impede αGP action. Isoamylase can be used to de-branch starch, yielding linear amylodextrin. Isoamylase-pretreated starch can result in a higher F6P concentration in the final product. Isoamylase and pullulanase cleave alpha-1,6-glycosidic bonds, which allows for more complete degradation of starch by alpha-glucan phosphorylase. Alpha-amylase cleaves alpha-1,4-glycosidic bonds, therefore alpha-amylase is used to degrade starch into fragments for quicker conversion to idose and increased solubility.

Maltose phosphorylase (MP) can be used to increase idose yields by phosphorolytically cleaving the degradation product maltose into G1P and glucose. Alternatively, 4-glucan transferase (4GT) can be used to increase idose yields by recycling the degradation products glucose, maltose, and maltotriose into longer maltooligosaccharides; which can be phosphorolytically cleaved by αGP to yield G1P.

In certain embodiments, cellulose and its derived products can be converted to idose through a series of steps. The process provides an in vitro synthetic pathway that involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; converting T6P to S6P catalyzed by S6PE, and converting S6P to sorbose catalyzed by S6PP. In this process, the phosphate ions can be recycled by the step of converting cellodextrin and cellobiose to G1P.

In some embodiments, polyphosphate and polyphosphate glucokinase (PPGK) can be added to the process, thus increasing yields of idose by phosphorylating the degradation product glucose to G6P.

In other embodiments, idose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; converting T6P to S6P catalyzed by S6PE; S6P to I6P by I6PI, and I6P to idose by I6PP.

Processes of the invention use low-cost starting materials and reduce production costs by decreasing costs associated with the feedstock and product separation. Starch, cellulose, sucrose and some of their derivatives are less expensive feedstocks than, for example, lactose. When idose is produced from biomass or lactose, yields are lower than in the present invention, and idose must be separated from other sugars via chromatography, which leads to higher production costs. Furthermore, our process is animal-free.

The step of converting S6P to idose according to the invention is an irreversible phosphatase reaction, regardless of the feedstock. Therefore, idose is produced with a very high yield while effectively minimizing the subsequent product separation costs.

In contrast to cell-based manufacturing methods, the invention involves a cell-free preparation of idose, has relatively high reaction rates due to the elimination of the cell membrane, which often slows down the transport of substrate/product into and out of the cell. It also has a final product free of nutrient-rich fermentation media/cellular metabolites.

A particular embodiment of the invention is idose produced by the processes described herein for producing idose.

Tagatose

Processes for making tagatose include converting F6P to T6P, catalyzed by an epimerase; and converting the T6P to tagatose, catalyzed by a phosphatase.

Epimerases suitable for use in the processes to convert F6P to T6P include F6PEs. Examples of F6PEs include, but are not limited to the following proteins: Uniprot ID E8N0N6, E4SEH3, I0I507, H1XRG1, and B5YBD7. Uniprot IDs E8N0N6 and I0I507 both catalyze the F6PE reaction and share 27% amino acid sequence identity. Therefore, examples of F6PEs also include any homologues having at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 99% amino acid sequence identity to any of the aforementioned Uniprot IDs.

Phosphatases that convert T6P to tagatose (D-tagatose), T6PPs may be used in a process. Examples of T6PPs include, but are not limited to the following proteins: Uniprot ID 029805, D2RHV2 and F2KMK2. Uniprot IDs 029805 and F2KMK2 both catalyze the F6PE reaction and share 67% amino acid sequence identity. Therefore, examples of T6PPs also include any homologues having at least 65%, preferably at least 70%, more preferably at least 75%, more preferably at least 80%, more preferably at least 85%, even more preferably at least 90%, most preferably at least 95%, and even most preferably at least 96%, 97%, 98%, 99%, or 100% amino acid sequence identity to any of the aforementioned Uniprot IDs.

A process for preparing tagatose also includes the step of enzymatically converting glucose 6-phosphate (G6P) to the F6P, and this step is catalyzed by phosphoglucose isomerase (PGI). The process for preparing tagatose additionally includes the step of converting glucose 1-phosphate (G1P) to the G6P, where the step is catalyzed by phosphogluco-mutase (PGM). Furthermore, tagatose production process also includes the step of converting a saccharide to the G1P that is catalyzed at least one enzyme.

Therefore, a process for preparing tagatose, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglucoisomerase (PGI, EC 5.3.1.9); (iv) converting F6P to T6P via fructose 6-phosphate epimerase (F6PE), and (v) converting T6P to tagatose via tagatose 6-phosphate phosphatase (T6PP).

Typically, the ratios of enzyme units used in the process are 1:1:1:1:1 (αGP:PGM:PGI:F6PE:T6PP). To optimize product yields, these ratios can be adjusted in any number of combinations. For example, a ratio of 3:1:1:1:1 can be used to maximize the concentration of phosphorylated intermediates, which will result in increased activity of the downstream reactions. Conversely, a ratio of 1:1:1:1:3 can be used to maintain a robust supply of phosphate for αGP, which will result in more efficient phosphorolytic cleavage of alpha-1, 4-glycosidic bonds. A ratio of enzymes, for example, 3:1:1:1:3 can be used to further increase the reaction rate. Therefore, the enzyme ratios, including other optional enzymes discussed below, can be varied to increase the efficiency of tagatose production. For example, a particular enzyme may be present in an amount about 2×, 3×, 4×, 5×, etc. relative to the amount of other enzymes.

Tagatose can also be produced from fructose. For example, the process involves generating F6P from fructose and polyphosphate catalyzed by polyphosphate fructokinase (PPFK); converting F6P to T6P catalyzed by F6PE; and converting T6P to tagatose catalyzed by T6PP. The fructose can be produced, for example, by an enzymatic conversion of sucrose.

Tagatose can be produced from sucrose. The process provides an in vitro synthetic pathway that includes the following enzymatic steps: generating G1P from sucrose and free phosphate catalyzed by sucrose phosphorylase (SP); converting G1P to G6P catalyzed by PGM; converting G6P to F6P catalyzed by PGI; converting F6P to T6P catalyzed by F6PE; and converting T6P to tagatose catalyzed by T6PP.

The phosphate ions generated when T6P is converted to tagatose can then be recycled in the step of converting sucrose to G1P. Additionally, PPFK and polyphosphate can be used to increase tagatose yields by producing F6P from fructose generated by the phosphorolytic cleavage of sucrose by SP.

A process for preparing tagatose includes the following steps: generating glucose from polysaccharides and oligosaccharides by enzymatic hydrolysis or acid hydrolysis, converting glucose to G6P catalyzed by at least one enzyme, generating fructose from polysaccharides and oligosaccharides by enzymatic hydrolysis or acid hydrolysis, and converting fructose to G6P catalyzed by at least one enzyme. Examples of the polysaccharides and oligosaccharides are enumerated above.

Cellulose and its derived products can be converted to tagatose through a series of steps. The process involves the following steps: generating G1P from cellodextrin and cellobiose and free phosphate catalyzed by cellodextrin phosphorylase (CDP) and cellobiose phosphorylase (CBP), respectively; converting G1P to G6P catalyzed by PGM; converting G6P to F6P catalyzed by PGI; converting F6P to T6P catalyzed by F6PE; and converting T6P to tagatose catalyzed by T6PP. In this process, the phosphate ions can be recycled by the step of converting cellodextrin and cellobiose to G1P.

Tagatose can be generated from glucose. The process involves the steps of generating G6P from glucose and polyphosphate catalyzed by polyphosphate glucokinase (PPGK); converting G6P to F6P catalyzed by PGI; converting F6P to T6P catalyzed by F6PE; and converting T6P to tagatose catalyzed by T6PP.

Psicose

Processes for making psicose include converting fructose 6-phosphate (F6P) to psicose 6-phosphate (P6P) catalyzed by an epimerase (e.g., psicose 6-phosphate 3-epimerase, P6PE) and converting the P6P produced to psicose catalyzed by a phosphatase (e.g., psicose 6-phosphate phosphatase, P6PP).

Examples of P6PEs include, but are not limited to the following proteins, identified by UNIPROT ID numbers: D9TQJ4, A0A090IXZ8, and P32719. Uniprot IDs A0A090IXZ8 and D9TQJ4 both catalyze the P6PE reaction and share 45% amino acid sequence identity. Therefore, examples of P6PEs also include any homologues having at least 45%, preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100% to any of the aforementioned Uniprot IDs.

Examples of P6PPs include, but are not limited to the following proteins: Uniprot ID. A3DC21, Q5LGR4, and Q89ZR1. Uniprot IDs A3DC21 and Q89ZR1 both catalyze the P6PP reaction and share 45% amino acid sequence identity. Therefore, examples of P6PPs also include any homologues having at least 45%, preferably at least 50%, more preferably at least 55%, more preferably at least 60%, more preferably at least 65%, more preferably at least 70%, more preferably at least 75%, more preferably at least 80%, more preferably at least 85%, even more preferably at least 90%, most preferably at least 95%, and even most preferably at least 96, 97, 98, 99 or 100% to any of the aforementioned Uniprot IDs.

A process for preparing psicose also includes the step of enzymatically converting glucose 6-phosphate (G6P) to the F6P, and this step is catalyzed by phosphoglucose isomerase (PGI). The process for preparing psicose additionally includes the step of converting glucose 1-phosphate (G1P)

to the G6P, where the step is catalyzed by phosphogluco-mutase (PGM). Furthermore, psicose production process also includes the step of converting a saccharide to the G1P that is catalyzed at least one enzyme.

Therefore, a process for preparing psicose, for example, include the following steps: (i) converting a saccharide to glucose 1-phosphate (G1P) using one or more enzymes; (ii) converting G1P to G6P using phosphoglucomutase (PGM, EC 5.4.2.2); (iii) converting G6P to F6P using phosphoglu-coisomerase (PGI, EC 5.3.1.9); (iv) converting F6P to P6P via psicose 6-phosphate epimerase (P6PE), and (v) converting P6P to psicose via psicose 6-phosphate phosphatase (P6PP).

Typically, the ratios of enzyme units used in the process are 1:1:1:1:1 (αGP:PGM:PGI:P6PE:P6PP). To optimize product yields, these ratios can be adjusted in any number of combinations. For example, a ratio of 3:1:1:1:1 can be used to maximize the concentration of phosphorylated interme-diates, which will result in increased activity of the down-stream reactions.

Conversely, a ratio of 1:1:1:1:3 can be used to maintain a robust supply of phosphate for αGP, which will result in more efficient phosphorolytic cleavage of alpha-1,4-glyco-sidic bonds. A ratio of enzymes, for example, 3:1:1:1:3 can be used to further increase the reaction rate. Therefore, the enzyme ratios, including other optional enzymes discussed below, can be varied to increase the efficiency of tagatose production. For example, a particular enzyme may be pres-ent in an amount about 2×, 3×, 4×, 5×, etc. relative to the amount of other enzymes.

Psicose can also be produced from fructose. For example, the process involves generating F6P from fructose and polyphosphate catalyzed by polyphosphate fructokinase (PPFK); converting F6P to P6P catalyzed by P6PE; and converting P6P to psicose catalyzed by P6PP. The fructose can be produced, for example, by an enzymatic conversion of sucrose.

Psicose can be produced from sucrose. The process includes the following enzymatic steps: generating G1P from sucrose and free phosphate catalyzed by sucrose phos-phorylase (SP); converting G1P to G6P catalyzed by PGM; converting G6P to F6P catalyzed by PGI; converting F6P to P6P catalyzed by P6PE; and converting P6P to psicose catalyzed by P6PP.

The phosphate ions generated when P6P is converted to psicose can then be recycled in the step of converting sucrose to G1P. Additionally, PPFK and polyphosphate can be used to increase psicose yields by producing F6P from fructose generated by the phosphorolytic cleavage of sucrose by SP.

A process for preparing psicose includes the following steps: generating glucose from polysaccharides and oligo-saccharides by enzymatic hydrolysis or acid hydrolysis, converting glucose to G6P catalyzed by at least one enzyme, generating fructose from polysaccharides and oligosaccha-rides by enzymatic hydrolysis or acid hydrolysis, and con-verting fructose to G6P catalyzed by at least one enzyme. Examples of the polysaccharides and oligosaccharides are enumerated above.

Cellulose and its derived products can be converted to psicose through a series of steps. The process involves the following steps: generating G1P from cellodextrin and cel-lobiose and free phosphate catalyzed by cellodextrin phos-phorylase (CDP) and cellobiose phosphorylase (CBP), respectively; converting G1P to G6P catalyzed by PGM; converting G6P to F6P catalyzed by PGI; converting F6P to P6P catalyzed by P6PE; and converting P6P to psicose catalyzed by P6PP. In this process, the phosphate ions can be recycled by the step of converting cellodextrin and cellobi-ose to G1P.

Psicose can be generated from glucose. The process involves the steps of generating G6P from glucose and polyphosphate catalyzed by polyphosphate glucokinase (PPGK); converting G6P to F6P catalyzed by PGI; convert-ing F6P to P6P catalyzed by P6PE; and converting P6P to psicose catalyzed by P6PP.

EXAMPLES

Materials and Methods

Chemicals

All chemicals, including corn starch, soluble starch, maltodextrins, glucose, filter paper were reagent grade or higher and purchased from Sigma-Aldrich (St. Louis, MO, USA) or Fisher Scientific (Pittsburgh, PA, USA), unless otherwise noted. Restriction enzymes, T4 ligase, and Phu-sion DNA polymerase were purchased from New England Biolabs (Ipswich, MA, USA). Oligonucleotides were syn-thesized either by Integrated DNA Technologies (Coralville, IA, USA) or Eurofins MWG Operon (Huntsville, AL, USA). Regenerated amorphous cellulose used in enzyme purifica-tion was prepared from Avicel PH105 (FMC BioPolymer, Philadelphia, PA, USA) through its dissolution and regen-eration, as described in: Ye et al., *Fusion of a family 9 cellulose-binding module improves catalytic potential of Clostridium thermocellum cellodextrin phosphorylase on insoluble cellulose.* Appl. Microbiol. Biotechnol. 2011; 92:551-560. *Escherichia coli* Sig10 (Sigma-Aldrich, St. Louis, MO, USA) was used as a host cell for DNA manipu-lation and *E. coli* BL21 (DE3) (Sigma-Aldrich, St. Louis, MO, USA) was used as a host cell for recombinant protein expression. ZYM-5052 media including either 100 mg $L^{-1}$ ampicillin or 50 mg $L^{-1}$ kanamycin was used for *E. coli* cell growth and recombinant protein expression. Cellulase from *Trichoderma reesei* (Catalog number: C2730) and pullula-nase (Catalog number: P1067) were purchased from Sigma-Aldrich (St. Louis, MO, USA) and produced by Novozymes (Franklinton, NC, USA). Maltose phosphorylase (Catalog number: M8284) was purchased from Sigma-Aldrich.

Production and Purification of Recombinant Enzymes

The *E. coli* BL21 (DE3) strain harboring a protein expres-sion plasmid was incubated in a 1-L Erlenmeyer flask with 100 mL of ZYM-5052 media containing either 100 mg $L^{-1}$ ampicillin or 50 mg L-kanamycin. Cells were grown at 37° C. with rotary shaking at 220 rpm for 16-24 hours. The cells were harvested by centrifugation at 12° C. and washed once with either 20 mM phosphate buffered saline (pH 7.5) containing 50 mM NaCl and 5 mM MgCl₂ (heat precipita-tion and cellulose-binding module) or 20 mM phosphate buffered saline (pH 7.5) containing 300 mM NaCl and 5 mM imidazole (Ni purification). The cell pellets were re-sus-pended in the same buffer and lysed by ultra-sonication (Fisher Scientific Sonic Dismembrator Model 500; 5 s pulse on and 10 s off, total 21 min at 50% amplitude). After centrifugation, the target proteins in the supernatants were purified.

Three approaches were used to purify the various recom-binant proteins. His-tagged proteins were purified by the Ni Sepharose 6 Fast Flow resin (GE Life Sciences, Marlbor-ough, MA, USA). Fusion proteins containing a cellulose-binding module (CBM) and self-cleavage intein were puri-fied through high-affinity adsorption on a large surface-area regenerated amorphous cellulose. Heat precipitation at 70-95° C. for 5-30 min was used to purify hyperthermo-stable enzymes. The purity of the recombinant proteins was examined by sodium dodecyl sulfate polyacrylamide gel electrophoresis (SDS-PAGE).

Enzymes Used and their Activity Assays

Alpha-glucan phosphorylase (αGP) from *Thermotoga maritima* (Uniprot ID G4FEH8) was used. Activity was assayed in 50 mM sodium phosphate buffer (pH 7.2) containing 1 mM MgCl₂, and 30 mM maltodextrin at 50° C. The reaction was stopped via filtration of enzyme with a Vivaspin 2 concentrator (10,000 MWCO) (Vivaproducts, Inc., Littleton, MA, USA). Glucose 1-phosphate (G1P) was measured using a glucose hexokinase/G6PDH assay kit (Sigma Aldrich, Catalog No. GAHK20-1KT) supplemented with 25 U/mL phosphoglucomutase. A unit (U) is described as μmol/min.

Phosphoglucomutase (PGM) from *Thermococcus kodakaraensis* (Uniprot ID Q68BJ6) was used. Activity was measured in 50 mM HEPES buffer (pH 7.2) containing 5 mM MgCl₂ and 5 mM G1P at 50° C. The reaction was stopped via filtration of enzyme with a Vivaspin 2 concentrator (10,000 MWCO). The product glucose 6-phosphate (G6P) was determined using a hexokinase/G6PDH assay kit (Sigma Aldrich, Catalog No. GAHK20-1KT).

Two different sources of phosphoglucoisomerase (PGI) were used from *Clostridium thermocellum* (Uniprot ID A3DBX9) and *Thermus thermophilus* (Uniprot ID Q5SLL6). Activity was measured in 50 mM HEPES buffer (pH 7.2) containing 5 mM MgCl₂ and 10 mM G6P at 50° C. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P. This 200 μL reaction contained 50 mM HEPES (pH 7.2), 5 mM MgCl₂, 10 mM G6P, 1.5 mM ATP, 1.5 mM phosphoenol pyruvate, 200 μM NADH, 0.1 U PGI, 5 U PK, and 5 U LD.

The recombinant cellodextrin phosphorylase and cellobiose phosphorylase from *C. thermocellum* are described in Ye et al. Spontaneous high-yield production of hydrogen from cellulosic materials and water catalyzed by enzyme cocktails. ChemSusChem 2009; 2:149-152. Their activities were assayed as described.

The recombinant polyphosphate glucokinase from *Thermobifida fusca* YX is described in Liao et al., One-step purification and immobilization of thermophilic polyphosphate glucokinase from *Thermobifida fusca* YX: glucose-6-phosphate generation without ATP. Appl. Microbiol. Biotechnol. 2012; 93:1109-1117. Its activities were assayed as described.

The recombinant isoamylase from *Sulfolobus tokodaii* is described in Cheng et al., Doubling power output of starch biobattery treated by the most thermostable isoamylase from an archaeon *Sulfolobus tokodaii*. Scientific Reports 2015; 5:13184. Its activities were assayed as described.

The recombinant 4-alpha-glucanoltransferase from *Thermococcus litoralis* is described in Jeon et al. 4-a-Glucanotransferase from the Hyperthermophilic Archaeon *Thermococcus Litoralis*. Eur. J. Biochem. 1997; 248:171-178. Its activity was measured as described.

Sucrose phosphorylase from *Thermoanaerobacterium thermosaccharolyticum* (Uniprot ID D9TT09) was used (Verhaeghe et al. The quest for a thermostable sucrose phosphorylase reveals sucrose 6'-phosphate phosphorylase as a novel specificity. Appl Microbiol Biotechnol. 2014 August; 98(16):7027-37). Its activity was measured in 50 mM HEPES buffer (pH 7.5) containing 10 mM sucrose and 12 mM organic phosphate. Glucose 1-phosphate (G1P) was measured using a glucose hexokinase/G6PDH assay kit supplemented with 25 U/mL phosphoglucomutase as with alpha-glucan phosphorylase.

Psicose 6-phosphate 3-epimerase (P6PE) from *Thermoanaerobacterium thermosaccharolyticum* (Uniprot ID D9TQJ4) was used. Activity was measured in 50 mM HEPES buffer (pH 7.2) containing 5 mM MgCl₂, 500 μM CoCl₂, 1 U/mL P6PP, and 10 mM F6P at 50° C. The reaction was stopped via filtration of enzyme with a Vivaspin 2 concentrator (10,000 MWCO). The product, psicose 6-phosphate (P6P), was determined using Psicose 6-phosphate phosphatase and detecting free phosphate release. To detect free phosphate release, 500 μL of a solution containing 0.1 M zinc acetate and 2 mM ammonium molybdate (pH 5) was added to 50 μL of reaction. This was mixed and followed by 125 μL of 5% ascorbic acid (pH 5). This solution was mixed then incubated at 30° C. for 20 min. The absorbance at 850 nm was read to determine free phosphate release. Psicose was then verified via HPLC using an Agilent Hi-Plex H-column (sample and control run with 5 mM H₂SO₄ at 0.6 mL/min and 65° C.)

Allose 6-phosphate isomerase (A6PI) from *Clostridium thermocellum* (Uniprot ID W4V2C8) with the amino acid sequence set forth in SEQ ID NO: 1 was used. Activity was measured in 50 mM HEPES buffer (pH 7.2) containing 5 mM MgCl₂, 500 μM CoCl₂, 1 U/mL P6PE, 1 U/mL A6PP, and 10 mM F6P at 50° C. The reaction was stopped via filtration of enzyme with a Vivaspin 2 concentrator (10,000 MWCO). The product, allose 6-phosphate (P6P), was determined using allose 6-phosphate phosphatase and detecting free phosphate release as described for P6PE. Allose verified via HPLC the same as psicose. Another A6PI, such as A6PI from *Symbiobacterium thermophilum* (Uniprot ID Q67LX4) with the amino acid sequence set forth in SEQ ID NO: 2, may be used.

Allose 6-phosphate phosphatase (A6PP) from *Rubellimicrobium thermophilum* (Uniprot ID S9SDA3) with the amino acid sequence set forth in SEQ ID NO: 3 was used. Activity was measured in 50 mM HEPES buffer (pH 7.2) containing 5 mM MgCl₂, 500 μM CoCl₂, 1 U/mL P6PE, 1 U/mL A6PI, and 10 mM F6P at 50° C. The reaction was stopped via filtration of enzyme with a Vivaspin 2 concentrator (10,000 MWCO). The product, allose, was determined by detecting free phosphate release as described for P6PE. Allose verified via HPLC the same as psicose. Other A6PPs, such as A6PP from *Thermotoga maritima* (Uniprot ID Q9X0Y1) with the amino acid sequence set forth in SEQ ID NO: 4, A6PP from *Thermoanaerobacterium saccharolyticum* (Uniprot ID I3VT81) with the amino acid sequence set forth in SEQ ID NO: 5, A6PP from *Streptomyces thermoautotrophicus* (Uniprot ID A0A132NF06) with the amino acid sequence set forth in SEQ ID NO: 6, and A6PP from *Sphaerobacter thermophilus* (Uniprot ID D1C7G9) with the amino acid sequence set forth in SEQ ID NO: 7, may be used.

Mannose 6-phosphate isomerase (M6PI) from *Pseudonocardia thermophila* (Uniprot ID A0A1M6TLY7) with the amino acid sequence set forth in SEQ ID NO: 8 was used. Activity was measured in 50 mM HEPES buffer (pH 7.2) containing 5 mM MgCl₂, 1 U/mL PGI, 1 U/mL M6PP, and 10 mM F6P at 50° C. The reaction was stopped via filtration of enzyme with a Vivaspin 2 concentrator (10,000 MWCO). The product, mannose 6-phosphate (M6P), was determined using mannose 6-phosphate phosphatase (M6PP) and detecting free phosphate release as described for P6PE. Mannose verified via HPLC the same as psicose. Other M6PIs such as M6PI from *Caldithrix abyssi* (Uniprot ID H1XQS6) with the amino acid sequence set forth in SEQ ID NO: 9, M6PI from *Myceliophthora thermophila* (Uniprot ID G2Q982) with the amino acid sequence set forth in SEQ ID NO: 10 and M6PI from *Treponema caldarium* (Uniprot ID F8F1Z8) with the amino acid sequence set forth in SEQ ID NO: 11 may be used.

Mannose 6-phosphate phosphatase (M6PP) from *Tepidimonas fonticaldi* (Uniprot ID A0A1A6DSI3) with the amino acid sequence set forth in SEQ ID NO: 12 was used. Activity was measured in 50 mM HEPES buffer (pH 7.2) containing 5 mM MgCl$_2$, and 10 mM mannose 6-phosphate at 50° C. The reaction was stopped via filtration of enzyme with a Vivaspin 2 concentrator (10,000 MWCO). The product, mannose, was determined by detecting free phosphate release as described for P6PE. Mannose verified via HPLC the same as psicose. Other M6PP such as M6PP from *Thermomonas hydrothermalis* (Uniprot ID A0A1M4UN08) with the amino acid sequence set forth in SEQ ID NO: 13 and M6PP from *Sulfurivirga caldicuralii* (Uniprot ID A0A1N6FCW3) with the amino acid sequence set forth in SEQ ID NO: 14 may be used.

Bifunctional phosphoglucose/phosphomannose isomerase (PGPMI) from *Syntrophothermus lipocalidus* (Uniprot ID D7CPH7) with the amino acid sequence set forth in SEQ ID NO: 15 was used. Activity was measured in 50 mM HEPES buffer (pH 7.2) containing 5 mM MgCl$_2$, 1 U/mL M6PP, and 10 mM G6P at 50° C. The reaction was stopped via filtration of enzyme with a Vivaspin 2 concentrator (10,000 MWCO). The product, M6P, was determined using M6PP and detecting free phosphate release as described for P6PE. Mannose verified via HPLC the same as psicose. Other PGPMI such as PGPMI from *Schleiferia thermophila* (Uniprot ID A0A085L170) with the amino acid sequence set forth in SEQ ID NO: 16 and PGPMI from *Thermodesulfobium narugense* (Uniprot ID M1E6Z3) with the amino acid sequence set forth in SEQ ID NO: 17 may be used.

Galactose 6-phosphate isomerase (Gal6PI) from *Lactococcus lactis* (obligate dimer; Uniprot IDs P23494 and P23495 with the amino acid sequences set forth in SEQ ID NO: 18 and 19, respectively) is used (van Rooijen et al. *Molecular Cloning, Characterization, and Nucleotide Sequence of the Tagatose 6-Phosphate Pathway Gene Cluster of the Lactose Operon of Lactococcus Zactis*. J. Biol. Chem. 1991; 266:7176-7181). Activity is measured in 50 mM HEPES buffer (pH 7.2) containing 5 mM MgCl$_2$, 1 U/mL fructose 6-phosphate 4-epimerase (F6PE), 1 U/mL galactose 6-phosphate phosphatase (Gal6PP), and 10 mM fructose 6-phosphate at 37° C. The reaction is stopped via filtration of enzyme with a Vivaspin 2 concentrator (10,000 MWCO). The product, galactose 6-phosphate (gal6P), is determined using Gal6PP and detecting free phosphate release as described for P6PE. Galactose verified via HPLC the same as psicose.

Galactose 6-phosphate phosphatase (Gal61PP) from *Bacteroides thetaiotaomicron* (Uniprot ID Q8A2F3) with the amino acid sequence set forth in SEQ ID NO: 20 was used. Activity was measured in 50 mM HEPES buffer (pH 7.2) containing 5 mM MgCl$_2$, and 10 mM galactose 6-phosphate at 50° C. The reaction was stopped via filtration of enzyme with a Vivaspin 2 concentrator (10,000 MWCO). The product, galactose, was determined by detecting free phosphate release as described for P6PE. Galactose verified via HPLC the same as psicose.

Fructose 6-phosphate phosphatase (F6PP) from *Halothermothrix orenii* (Uniprot ID B8CWV3) with the amino acid sequence set forth in SEQ ID NO: 21 was used. Activity was measured in 50 mM HEPES buffer (pH 7.2) containing 5 mM MgCl$_2$, and 10 mM fructose 6-phosphate at 50° C. The reaction was stopped via filtration of enzyme with a Vivaspin 2 concentrator (10,000 MWCO). The product, fructose, was determined by detecting free phosphate release as described for P6PE. Fructose verified via HPLC the same as psicose.

Tagatose 6-phosphate phosphatase (T6PP) from *Archaeoglobus fugidis* (Uniprot ID A0A075WB87) was used. Activity was measured in 50 mM HEPES buffer (pH 7.2) containing 5 mM MgCl$_2$ and 10 mM T6P at 50° C. The reaction was stopped via filtration of enzyme with a Vivaspin 2 concentrator (10,000 MWCO). Tagatose production was determined by detecting free phosphate release as described for F6PE.

Psicose 6-phosphate phosphatase (P6PP) from *Clostridium thermocellum* (UNIPROT ID A3DC21), was used. Activity was measured in 50 mM HEPES buffer (pH 7.2) containing 5 mM MgCl2, 80 μM CoCl2, 1 U/mL P6PE, and 10 mM F6P at 50° C. The reaction was stopped via filtration of enzyme with a Vivaspin 2 concentrator (10,000 MWCO). The product, psicose, was determined through detecting free phosphate release as described for P6PE.

Enzyme units used in each Example below can be increased or decreased to adjust the reaction time as desired. For example, if one wanted to perform Example 9 in 8 h instead of 24 h, the units of the enzymes would be increased about 3-fold. Conversely, if one wanted perform example 9 in 48 h instead of 24 h the enzyme units could be decreased about 2-fold. These examples illustrate how the amount of enzyme units can be used to increase or decrease reaction time while maintaining constant productivity.

All Products

Example 1

To validate the technical feasibility of the enzymatic biosynthesis of fructose 6-phosphate from starch, three enzymes were recombinantly expressed: alpha-glucan phosphorylase from *T. maritima* (Uniprot ID G4FEH8), phosphoglucomutase from *Thermococcus kodakaraensis* (Uniprot ID Q68BJ6), and phosphoglucoisomerase from *Clostridium thermocellum* (Uniprot ID A3DBX9). The recombinant proteins were over-expressed in *E. coli* BL21 (DE3) and purified as described above.

A 0.20 mL reaction mixture containing 10 g/L soluble starch, 50 mM phosphate buffered saline pH 7.2, 5 mM MgCl$_2$, 0.5 mM ZnCl$_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 2

Same tests as in Example 1 (other than reaction temperatures) were carried out from 40 to 80° C. It was found that 10 g/L soluble starch produced 0.9 g/L F6P at 40° C. and 3.6 g/L F6P at 80° C. after 40 hour reactions. These results suggest that increasing reaction temperature for this set of enzymes increased F6P yields, but too high of temperature may impair some enzyme activity.

Example 3

It was found that, at 80° C., an enzyme ratio of αGP: PGM:PGI of approximately 1:1:1 resulted in fast F6P generation. It was noted that the enzyme ratio did not influence final F6P concentration greatly if the reaction time was long enough. However, the enzyme ratio affects reaction rates and the total cost of enzymes used in the system.

Example 4

A 0.20 mL reaction mixture containing 10 g/L maltodextrin, 50 mM phosphate buffered saline pH 7.2, 5 mM $MgCl_2$, 0.5 mM $ZnCl_2$, 0.01 U of αGP, 0.01 U PGM, and 0.01 U PGI was incubated at 50° C. for 24 hours. The reaction was stopped via filtration of enzyme with a Vivaspin 2 concentrator (10,000 MWCO). The product, fructose 6-phosphate (F6P), was determined using a fructose 6-phosphate kinase (F6PK)/pyruvate dehydrogenase (PK)/lactate dehydrogenase (LD) coupled enzyme assay where a decrease in absorbance at 340 nm indicates production of F6P as described above. The final concentration of F6P after 24 hours was 3.6 g/L.

Example 5

To test for F6P production from Avicel, Sigma cellulase was used to hydrolyze cellulose at 50° C. To remove beta-glucosidase from commercial cellulase, 10 filter paper units/mL of cellulase was mixed to 10 g/L Avicel at an ice-water bath for 10 min. After centrifugation at 4° C., the supernatant containing beta-glucosidase was decanted. Avicel that was bound with cellulase containing endoglucanase and cellobiohydrolase was resuspended in a citrate buffer (pH 4.8) for hydrolysis at 50° C. for three days. The cellulose hydrolysate was mixed with 5 U/mL cellodextrin phosphorylase, 5 U/L cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours and high concentrations of F6P were found (small amounts of glucose and no cellobiose). F6P was detected using the coupled enzyme assay described above. Glucose was detected using a hexokinase/G6PDH assay kit as described above.

Example 6

To increase F6P yields from Avicel, Avicel was pretreated with concentrated phosphoric acid to produce amorphous cellulose (RAC), as described in Zhang et al. A transition from cellulose swelling to cellulose dissolution by o-phosphoric acid: evidence from enzymatic hydrolysis and supramolecular structure. Biomacromolecules 2006; 7:644-648. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was resuspended in a citrate buffer (pH 4.8) for hydrolysis at 50° C. for 12 hours. The RAC hydrolysate was mixed with 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 10 mM phosphate, 5 mM $MgCl_2$ and 0.5 mM $ZnCl_2$. The reaction was conducted at 60° C. for 72 hours. High concentrations of F6P and glucose were recovered because no enzymes were added to convert glucose to F6P. F6P was detected using the coupled enzyme assay described above. Glucose was detected using a hexokinase/G6PDH assay kit as described above.

Example 7

To further increase F6P yields from RAC, polyphosphate glucokinase and polyphosphate were added. To remove beta-glucosidase from commercial cellulase, 10 filter paper units/mL of cellulase was mixed with 10 g/L RAC in an ice-water bath for 5 min. After centrifugation at 4° C., the supernatant containing beta-glucosidase was decanted. The RAC that was bound with cellulase containing endoglucanase and cellobiohydrolase was re-suspended in a citrate buffer (pH 4.8) for hydrolysis at 50° C. was incubated in a citrate buffer (pH 4.8) for hydrolysis at 50° C. for 12 hours. The RAC hydrolysate was mixed with 5 U/mL polyphosphate glucokinase, 5 U/mL cellodextrin phosphorylase, 5 U/mL cellobiose phosphorylase, 5 U/mL of αGP, 5 U/mL PGM, and 5 U/mL PGI in a 100 mM HEPES buffer (pH 7.2) containing 50 mM polyphosphate, 10 mM phosphate, 5 mM $MgCl_2$ and 0.5 mM $ZnCl_2$. The reaction was conducted at 50° C. for 72 hours. F6P was found in high concentrations with only small amounts of glucose now present. F6P was detected using the coupled enzyme assay described above. Glucose was detected using a hexokinase/G6PDH assay kit as described above.

Example 8

To determine the concentration range of phosphate buffered saline (PBS), a 0.20 mL reaction mixture containing 50 g/L maltodextrin; 6.25 mM, 12.5 mM, 25 mM, 37.5 mM, or 50 mM phosphate buffered saline pH 7.2; 5 mM MgCl2; 0.1 U of αGP; 0.1 U PGM; and 0.1 U PGI was incubated at 50° C. for 6 hours. The short duration ensures completion was not reached, and therefore differences in efficiency can be clearly seen. Production of F6P was quantified using a fructose 6-phosphate kinase (F6PK)/pyruvate dehydrogenase (PK)/lactate dehydrogenase (LD) coupled enzyme assay where a decrease in absorbance at 340 nm indicates production of F6P. Respectively, a yield of 4.5 g/L, 5.1 g/L, 5.6 g/L, 4.8 g/L, or 4.9 g/L F6P was obtained for the reactions containing either 6.25 mM, 12.5 mM, 25 mM, 37.5 mM, or 50 mM phosphate buffered saline pH 7.2 (Table 1). These results indicate that a concentration of 25 mM PBS pH 7.2 was ideal for these particular reaction conditions. It is important to note that even the use of 6.25 mM PBS at pH 7.2 results in significant turnover due to phosphate recycling. This shows that the disclosed phosphate recycling methods are able to keep phosphate levels low even at industrial levels of volumetric productivity (e.g., 200-300 g/L maltodextrin).

TABLE 1

| Concentration of PBS pH 7.2 (mM) | g/L of F6P |
|---|---|
| 6.25 | 4.5 |
| 12.5 | 5.1 |
| 25 | 5.6 |

TABLE 1-continued

| Concentration of PBS pH 7.2 (mM) | g/L of F6P |
|---|---|
| 37.5 | 4.8 |
| 50 | 4.9 |

Example 9

To determine the pH range of the cascade reaction, a 0.20 mL reaction mixture containing 50 g/L maltodextrin; 50 mM phosphate buffered saline pH 6.0, 6.2, 6.4, 6.6, 6.8, 7.0 7.2, or 7.3; 5 mM MgCl2; 0.02 U of αGP; 0.02 U PGM; and 0.02 U PGI was incubated at 50° C. for 16 hours. The units are lowered to ensure completion was not reached, and therefore differences in efficiency can be clearly seen. Production of F6P was quantified as in example 12. Respectively, a yield of 4.0 g/L, 4.1 g/L 4.2 g/L, 4.1 g/L, 4.4 g/L, 4.1 g/L, 3.8 g/L or 4.0 g/L F6P was obtained for reactions containing 50 mM phosphate buffered saline at pH 6.0, 6.2, 6.4, 6.6, 6.8, 7.0, 7.2, or 7.3 (Table 2). These results indicate that a pH of 6.8 was ideal for these particular reaction conditions, although the system works through a wide pH range.

TABLE 2

| pH of PBS | g/L of F6P |
|---|---|
| 6.0 | 4.0 |
| 6.2 | 4.1 |
| 6.4 | 4.2 |
| 6.6 | 4.1 |
| 6.8 | 4.4 |
| 7.0 | 4.1 |
| 7.2 | 3.8 |
| 7.3 | 4.0 |

Allose

Example 10

To validate allose production from F6P, 10 g/L F6P was mixed with 1 U/mL P6PE, 1 U/mL A6PI and 1 U/mL A6PP in 50 mM HEPES buffer (pH 7.2) containing 5 mM MgCl2 and 500 μM CoCl2. The reaction was incubated for 3 hours at 50° C. Conversion of F6P to allose was seen via HPLC (Agilent 1100 series) using an Agilent Hi-Plex H-column and refractive index detector. The sample and control were run in 5 mM H2SO4 at 0.6 mL/min and 65° C.

Example 11

To validate production of allose from maltodextrin, a 0.20 mL reaction mixture containing 20 g/L maltodextrin, 50 mM phosphate buffered saline pH 7.2, 5 mM MgCl2, 500 μM CoCl2, 0.05 U of αGP, 0.05 U PGM, 0.05 U PGI, 0.05 U P6PE, 0.05 U A6PI and 0.05 U A6PP was incubated at 50° C. for 24 hours. The reaction was stopped via filtration of enzyme with a Vivaspin 2 concentrator (10,000 MWCO). Allose was verified via HPLC as described in Example 10.

Example 12

A reaction mixture containing 200 g/L maltodextrin, 10 mM acetate buffer (pH 5.5), 5 mM MgCl2, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl2, 500 μM CoCl2, 0.05 U of αGP, 0.05 U PGM, 0.05 U PGI, 0.05 U P6PE, 0.05 U A6PI, and 0.05 U A6PP was incubated at 50° C. for 24 hours. Production of allose was verified as in Example 10.

Example 13

To further increase allose yields from maltodextrin, 0.05 U 4-glucan transferase (4GT) was added to the reaction described in Example 11.

A 0.2 mL reaction mixture containing 20 g/L isoamylase treated maltodextrin (see Example 12), 50 mM phosphate buffered saline pH 7.2, 5 mM MgCl2, 500 μM CoCl2, 0.05 U of αGP, 0.05 U PGM, 0.05 U PGI, 0.05 U P6PE, 0.05 U A6PI, 0.05 U A6PP, and 0.05 U 4GT was incubated at 50° C. for 24 hours.

Production of allose was verified as in Example 10.

Example 14

To further increase allose yields from maltodextrin, 0.05 U maltose phosphorylase is added to the reaction described in Example 11.

Example 15

To further increase allose yields from maltodextrin, 0.05 U polyphosphate glucokinase and 75 mM polyphosphate is added to the reaction described in Example 11.

Example 16

To produce allose from fructose, a reaction mixture containing 10 g/L fructose, 50 mM Tris buffer pH 7.0, 75 mM polyphosphate, 5 mM MgCl2, 500 μM CoCl2, 0.05 U fructose polyphosphate kinase, 0.05 U P6PE, 0.05 A6PI, and 0.05 U A6PP is incubated at 50° C. for 24 hours. Production of allose is quantified as in Example 10.

Example 17

To produce allose from glucose, a reaction mixture containing 10 g/L glucose, 50 mM Tris buffer pH 7.0, 75 mM polyphosphate, 5 mM MgCl2, 500 μM CoCl2, 0.05 U glucose polyphosphate kinase, 0.05 U PGI, 0.05 U P6PE, 0.05 A6PI, and 0.05 U A6PP is incubated at 50° C. for 24 hours. Production of allose is quantified as in Example 10.

Example 18

To produce allose from sucrose, a reaction mixture containing 10 g/L sucrose, 50 mM phosphate buffered saline pH 7.0, 5 mM MgCl2, 500 μM CoCl2, 0.05 U sucrose phosphorylase, 0.05 PGM, 0.05 U PGI, 0.05 U P6PE, 0.05 A6PI, and 0.05 U A6PP is incubated at 50° C. for 24 hours. Production of allose is quantified as in Example 10.

Example 19

To further increase yields of allose from sucrose, 75 mM polyphosphate and 0.05 polyphosphate fructokinase is added to the reaction mixture in Example 18. Production of allose is quantified as in Example 10.

Mannose

Example 20

To validate mannose production from F6P, 10 g/L F6P was mixed with 1 U/mL M6PI/PGPMI, and 1 U/mL M6PP in 50 mM HEPES buffer (pH 7.2) containing 5 mM MgCl$_2$. The reaction was incubated for 3 hours at 50° C. Conversion of F6P to mannose was seen via HPLC (Agilent 1100 series) using an Agilent Hi-Plex H-column and refractive index detector. The sample and control were run in 5 mM H$_2$SO$_4$ at 0.6 mL/min and 65° C.

Example 21

To validate production of mannose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), and 0.05 U M6PP was incubated at 50° C. for 24 hours. The reaction was stopped via filtration of enzyme with a Vivaspin 2 concentrator (10,000 MWCO). Mannose was verified via HPLC as described in Example 20.

Example 22

A reaction mixture containing 200 g/L maltodextrin, 10 mM acetate buffer (pH 5.5), 5 mM MgCl$_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), and 0.05 U M6PP was incubated at 50° C. for 24 hours. Production of mannose was verified as in Example 20.

Example 23

To further increase mannose yields from maltodextrin, 0.05 U 4-glucan transferase (4GT) was added to the reaction described in Example 21.

A 0.2 mL reaction mixture containing 20 g/L isoamylase treated maltodextrin (see Example 22), 50 mM phosphate buffered saline pH 7.2, 5 mM MgCl$_2$, 0.05 U of αGP, 0.05 U PGM, 0.05 U PGI, 0.05 U M6PI/PGPMI (no PGI needed in PGPMI case), 0.05 U M6PP, and 0.05 U 4GT was incubated at 50° C. for 24 hours. Production of mannose was verified as in Example 20.

Example 24

To further increase mannose yields from maltodextrin, 0.05 U maltose phosphorylase is added to the reaction described in Example 21.

Example 25

To further increase mannose yields from maltodextrin, 0.05 U polyphosphate glucokinase and 75 mM polyphosphate is added to the reaction described in Example 21.

Example 26

To produce mannose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U M6PI/PGPMI (no PGI needed in PGPMI case), and 0.05 U M6PP is incubated at 50° C. for 24 hours.

58

Production of mannose is quantified as in Example 20.

Example 27

To produce mannose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U M6PI/PGPMI (no PGI needed in PGPMI case), and 0.05 U M6PP is incubated at 50° C. for 24 hours. Production of mannose is quantified as in Example 20.

Example 28

To produce mannose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U M6PI/PGPMI (no PGI needed in PGPMI case), and 0.05 U M6PP is incubated at 50° C. for 24 hours. Production of mannose is quantified as in Example 20.

Example 29

To further increase yields of mannose from sucrose, 75 mM polyphosphate and 0.05 polyphosphate fructokinase is added to the reaction mixture in Example 28. Production of mannose is quantified as in Example 20.
Galactose

Example 30

To validate galactose production from F6P, 10 g/L F6P is mixed with 1 U/mL Gal6PI, and 1 U/mL Gal6PP in 50 mM HEPES buffer (pH 7.2) containing 5 mM MgCl$_2$. The reaction is incubated for 3 hours at 37° C. Conversion of F6P to galactose is seen via HPLC (Agilent 1100 series) using an Agilent Hi-Plex H-column and refractive index detector. The sample and control are run in 5 mM H$_2$SO$_4$ at 0.6 mL/min and 65° C.

Example 31

To validate production of galactose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U Gal6PI, and 0.05 U Gal6PP is incubated at 37° C. for 24 hours. The reaction is stopped via filtration of enzyme with a Vivaspin 2 concentrator (10,000 MWCO). Galactose is verified via HPLC as described in Example 30.

Example 32

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, 0.05 U Gal6PI, and 0.05 U Gal6PP is incubated at 37° C. for 24 hours. Production of galactose is verified as in Example 30.

Example 33

To further increase galactose yields from maltodextrin, 0.05 U 4-glucan transferase (4GT) is added to the reaction described in Example 31.

A 0.2 mL reaction mixture containing 20 g/L isoamylase treated maltodextrin (see Example 12), 50 mM phosphate buffered saline pH 7.2, 5 mM MgCl$_2$, 0.05 U of αGP, 0.05 U PGM, 0.05 U PGI, 0.05 U Gal6PI, 0.05 U Gal6PP, and 0.05 U 4GT is incubated at 37° C. for 24 hours. Production of galactose is verified as in Example 30.

Example 34

To further increase galactose yields from maltodextrin, 0.05 U maltose phosphorylase is added to the reaction described in Example 31.

Example 35

To further increase galactose yields from maltodextrin, 0.05 U polyphosphate glucokinase and 75 mM polyphosphate is added to the reaction described in Example 31.

Example 36

To produce galactose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U Gal6PI, and 0.05 U Gal6PP is incubated at 37° C. for 24 hours. Production of galactose is quantified as in Example 30.

Example 37

To produce galactose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U Gal6PI, and 0.05 U Gal6PP is incubated at 37° C. for 24 hours. Production of galactose is quantified as in Example 30.

Example 38

To produce galactose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U Gal6PI, and 0.05 U Gal6PP is incubated at 37° C. for 24 hours. Production of galactose is quantified as in Example 30.

Example 39

To further increase yields of galactose from sucrose, 75 mM polyphosphate and 0.05 polyphosphate fructokinase is added to the reaction mixture in Example 38. Production of galactose is quantified as in Example 30.

Example 40

To validate galactose production from Gal6P, 10 g/L Gal6P was mixed with 1 U/mL Gal6PP in 50 mM HEPES buffer (pH 7.2) containing 5 mM MgCl$_2$. The reaction was incubated for 1 hour at 50° C. Conversion of Gal6P to galactose is seen free phosphate detection. To detect free phosphate release, 500 µL of a solution containing 0.1 M zinc acetate and 2 mM ammonium molybdate (pH 5) was added to 50 µL of reaction. This was mixed and followed by 125 µL of 5% ascorbic acid (pH 5). This solution was mixed then incubated at 30° C. for 20 min. The absorbance at 850 nm was read to determine free phosphate release.
Fructose

Example 41

To validate fructose production from F6P, 10 g/L F6P was mixed with 1 U/mL F6PP in 50 mM HEPES buffer (pH 7.2) containing 5 mM MgCl$_2$. The reaction was incubated for 3 hours at 50° C. Conversion of F6P to fructose was seen via HPLC (Agilent 1100 series) using an Agilent Hi-Plex H-column and refractive index detector. The sample and control were run in 5 mM H$_2$SO$_4$ at 0.6 mL/min and 65° C.

Example 42

To validate production of fructose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, and 0.05 U F6PP was incubated at 50° C. for 24 hours. The reaction was stopped via filtration of enzyme with a Vivaspin 2 concentrator (10,000 MWCO). Fructose was verified via HPLC as described in Example 41.

Example 43

A reaction mixture containing 200 g/L maltodextrin, 10 mM acetate buffer (pH 5.5), 5 mM MgCl$_2$, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl$_2$, 0.05 U of αGP, 0.05 U PGM, 0.05 U PGI, and 0.05 U F6PP was incubated at 50° C. for 24 hours. Production of fructose was verified as in Example 41.

Example 44

To further increase fructose yields from maltodextrin, 0.05 U 4-glucan transferase (4GT) was added to the reaction described in Example 42.

A 0.2 mL reaction mixture containing 20 g/L isoamylase treated maltodextrin (see Example 12), 50 mM phosphate buffered saline pH 7.2, 5 mM MgCl$_2$, 0.05 U of αGP, 0.05 U PGM, 0.05 U PGI, 0.05 U F6PP, and 0.05 U 4GT was incubated at 50° C. for 24 hours. Production of fructose was verified as in Example 41.

Example 45

To further increase fructose yields from maltodextrin, 0.05 U maltose phosphorylase is added to the reaction described in Example 42.

Example 46

To further increase fructose yields from maltodextrin, 0.05 U polyphosphate glucokinase and 75 mM polyphosphate is added to the reaction described in Example 42.

Example 47

To produce fructose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, and 0.05 U F6PP is incubated at 50° C. for 24 hours. Production of fructose is quantified as in Example 41.

Example 48

To produce fructose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, and 0.05 U F6PP was incubated at 50° C. for 24 hours. Production of fructose was quantified as in Example 41.
Altrose

Example 49

To validate altrose production from F6P, 10 g/L F6P is mixed with 1 U/mL P6PE, 1 U/mL altrose 6-phosphate isomerase (Alt6PI), and 1 U/mL altrose 6-phosphate phosphatase (Alt6PP) in 50 mM HEPES buffer (pH 7.2) containing 5 mM $MgCl_2$. The reaction is incubated for 3 hours at 50° C. Conversion of F6P to altrose is seen via HPLC (Agilent 1100 series) using an Agilent Hi-Plex H-column and refractive index detector. The sample and control are run in 5 mM $H_2SO_4$ at 0.6 mL/min and 65° C.

Example 50

To validate production of altrose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U P6PE, 0.05 U Alt6PI, and 0.05 U Alt6PP is incubated at 50° C. for 24 hours. The reaction is stopped via filtration of enzyme with a Vivaspin 2 concentrator (10,000 MWCO). Altrose is verified via HPLC as described in Example 49.

Example 51

A reaction mixture containing 200 g/L maltodextrin, 10 mM acetate buffer (pH 5.5), 5 mM $MgCl_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, 0.05 U P6PE, 0.05 U Alt6PI, and 0.05 U Alt6PP is incubated at 50° C. for 24 hours. Production of altrose is verified as in Example 49.

Example 52

To further increase altrose yields from maltodextrin, 0.05 U 4-glucan transferase (4GT) is added to the reaction described in Example 50.
A 0.2 mL reaction mixture containing 20 g/L isoamylase treated maltodextrin (see Example 50), 50 mM phosphate buffered saline pH 7.2, 5 mM $MgCl_2$, 0.05 U of αGP, 0.05 U PGM, 0.05 U PGI, 0.05 U P6PE, 0.05 U Alt6PI, 0.05 U Alt6PP, and 0.05 U 4GT is incubated at 50° C. for 24 hours. Production of altrose is verified as in Example 49.

Example 53

To further increase altrose yields from maltodextrin, 0.05 U maltose phosphorylase is added to the reaction described in Example 50.

Example 54

To further increase altrose yields from maltodextrin, 0.05 U polyphosphate glucokinase and 75 mM polyphosphate is added to the reaction described in Example 50.

Example 55

To produce altrose from fructose, a reaction mixture containing 10 g/L fructose, 50 mM Tris buffer pH 7.0, 75 mM polyphosphate, 5 mM $MgCl_2$, 0.05 U fructose polyphosphate kinase, 0.05 U P6PE, 0.05 U Alt6PI, and 0.05 U Alt6PP is incubated at 50° C. for 24 hours. Production of altrose is quantified as in Example 49.

Example 56

To produce altrose from glucose, a reaction mixture containing 10 g/L glucose, 50 mM Tris buffer pH 7.0, 75 mM polyphosphate, 5 mM $MgCl_2$, 0.05 U glucose polyphosphate kinase, 0.05 U PGI, 0.05 U P6PE, 0.05 U Alt6PI, and 0.05 U Alt6PP is incubated at 50° C. for 24 hours. Production of altrose is quantified as in Example 49.

Example 57

To produce altrose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, 0.05 U P6PE, 0.05 U Alt6PI, and 0.05 U Alt6PP is incubated at 50° C. for 24 hours. Production of altrose is quantified as in Example 49.

Example 58

To further increase yields of altrose from sucrose, 75 mM polyphosphate and 0.05 polyphosphate fructokinase is added to the reaction mixture in Example 56. Production of altrose is quantified as in Example 49.
Talose

Example 59

To validate talose production from F6P, 10 g/L F6P is mixed with 1 U/mL F6PE, 1 U/mL talose 6-phosphate isomerase (Tal6PI), and 1 U/mL talose 6-phosphate phosphatase (Tal6PP) in 50 mM HEPES buffer (pH 7.2) containing 5 mM $MgCl_2$. The reaction is incubated for 3 hours at 50° C. Conversion of F6P to talose is seen via HPLC (Agilent 1100 series) using an Agilent Hi-Plex H-column and refractive index detector. The sample and control are run in 5 mM $H_2SO_4$ at 0.6 mL/min and 65° C.

Example 60

To validate production of talose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U Tal6PI, and 0.05 U Tal6PP is incubated at 50° C. for 24 hours. The reaction is stopped via filtration of enzyme with a Vivaspin 2 concentrator (10,000 MWCO). Talose is verified via HPLC as described in Example 59.

Example 61

A reaction mixture containing 200 g/L maltodextrin, 10 mM acetate buffer (pH 5.5), 5 mM $MgCl_2$, and 0.1 g/L isoamylase is incubated at 80° C. for 24 hours. This is used to create another reaction mixture containing 20 g/L iso-amylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U Tal6PI, and 0.05 U Tal6PP is incubated at 50° C. for 24 hours. Production of talose is verified as in Example 59.

Example 62

To further increase talose yields from maltodextrin, 0.05 U 4-glucan transferase (4GT) is added to the reaction described in Example 60.

A 0.2 mL reaction mixture containing 20 g/L isoamylase treated maltodextrin (see Example 60), 50 mM phosphate buffered saline pH 7.2, 5 mM MgCl$_2$, 0.05 U of αGP, 0.05 U PGM, 0.05 U PGI, 0.05 U F6PE, 0.05 U Tal6PI, 0.05 U Tal6PP, and 0.05 U 4GT is incubated at 50° C. for 24 hours. Production of talose is verified as in Example 59.

Example 63

To further increase talose yields from maltodextrin, 0.05 U maltose phosphorylase is added to the reaction described in Example 59.

Example 64

To further increase talose yields from maltodextrin, 0.05 U polyphosphate glucokinase and 75 mM polyphosphate is added to the reaction described in Example 60.

Example 65

To produce talose from fructose, a reaction mixture containing 10 g/L fructose, 50 mM Tris buffer pH 7.0, 75 mM polyphosphate, 5 mM MgCl$_2$, 0.05 U fructose polyphosphate kinase, 0.05 U F6PE, 0.05 U Tal6PI, and 0.05 U Tal6PP is incubated at 50° C. for 24 hours. Production of talose is quantified as in Example 59.

Example 66

To produce talose from glucose, a reaction mixture containing 10 g/L glucose, 50 mM Tris buffer pH 7.0, 75 mM polyphosphate, 5 mM MgCl$_2$, 0.05 U glucose polyphosphate kinase, 0.05 U PGI, 0.05 U F6PE, 0.05 U Tal6PI, and 0.05 U Tal6PP is incubated at 50° C. for 24 hours. Production of talose is quantified as in Example 59.

Example 67

To produce talose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U Tal6PI, and 0.05 U Tal6PP is incubated at 50° C. for 24 hours. Production of talose is quantified as in Example 59.

Example 68

To further increase yields of talose from sucrose, 75 mM polyphosphate and 0.05 polyphosphate fructokinase is added to the reaction mixture in Example 66. Production of talose is quantified as in Example 59.

Sorbose

Example 69

To validate sorbose production from F6P, 10 g/L F6P is mixed with 1 U/mL F6PE, 1 U/mL sorbose 6-phosphate 3-epimerase (S6PE), and 1 U/mL sorbose 6-phosphate phosphatase (S6PP) in 50 mM HEPES buffer (pH 7.2) containing 5 mM MgCl$_2$. The reaction is incubated for 3 hours at 50° C. Conversion of F6P to sorbose is seen via HPLC (Agilent 1100 series) using an Agilent Hi-Plex H-column and refractive index detector. The sample and control are run in 5 mM H$_2$SO$_4$ at 0.6 mL/min and 65° C.

Example 70

To validate production of sorbose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, and 0.05 U S6PP is incubated at 50° C. for 24 hours. The reaction is stopped via filtration of enzyme with a Vivaspin 2 concentrator (10,000 MWCO). Sorbose is verified via HPLC as described in Example 68.

Example 71

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L iso-amylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, and 0.05 U S6PP is incubated at 50° C. for 24 hours. Production of sorbose is verified as in Example 69.

Example 72

To further increase sorbose yields from maltodextrin, 0.05 U 4-glucan transferase (4GT) is added to the reaction described in Example 70.

A 0.2 mL reaction mixture containing 20 g/L isoamylase treated maltodextrin (see Example 70), 50 mM phosphate buffered saline pH 7.2, 5 mM MgCl$_2$, 0.05 U of αGP, 0.05 U PGM, 0.05 U PGI, 0.05 U F6PE, 0.05 U S6PE, 0.05 U S6PP, and 0.05 U 4GT is incubated at 50° C. for 24 hours. Production of sorbose is verified as in Example 69.

Example 73

To further increase sorbose yields from maltodextrin, 0.05 U maltose phosphorylase is added to the reaction described in Example 70.

Example 74

To further increase sorbose yields from maltodextrin, 0.05 U polyphosphate glucokinase and 75 mM polyphosphate is added to the reaction described in Example 69.

Example 75

To produce sorbose from fructose, a reaction mixture containing 10 g/L fructose, 50 mM Tris buffer pH 7.0, 75 mM polyphosphate, 5 mM MgCl$_2$, 0.05 U fructose poly-phosphate kinase, 0.05 U F6PE, 0.05 U S6PE, and 0.05 U S6PP is incubated at 50° C. for 24 hours. Production of sorbose is quantified as in Example 69.

Example 76

To produce sorbose from glucose, a reaction mixture containing 10 g/L glucose, 50 mM Tris buffer pH 7.0, 75 mM polyphosphate, 5 mM MgCl$_2$, 0.05 U glucose poly-phosphate kinase, 0.05 U PGI, 0.05 U F6PE, 0.05 U S6PE, and 0.05 U S6PP is incubated at 50° C. for 24 hours. Production of sorbose is quantified as in Example 69.

Example 77

To produce sorbose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U S6PE, and 0.05 U S6PP is incubated at 50° C. for 24 hours. Production of sorbose is quantified as in Example 69.

Example 78

To further increase yields of sorbose from sucrose, 75 mM polyphosphate and 0.05 polyphosphate fructokinase is added to the reaction mixture in Example 76. Production of sorbose is quantified as in Example 69.
Gulose

Example 79

To validate gulose production from F6P, 10 g/L F6P is mixed with 1 U/mL F6PE, 1 U/mL S6PE, 1 U/mL gulose 6-phosphate isomerase (Gul6PI), and 1 U/mL gulose 6-phosphate phosphatase (Gul6PP) in 50 mM HEPES buffer (pH 7.2) containing 5 mM MgCl$_2$. The reaction is incubated for 3 hours at 50° C. Conversion of F6P to gulose is seen via HPLC (Agilent 1100 series) using an Agilent Hi-Plex H-column and refractive index detector. The sample and control are run in 5 mM H$_2$SO$_4$ at 0.6 mL/min and 65° C.

Example 80

To validate production of gulose from maltodextrin, a 0.20 mL reaction mixture containing 20 g/L maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, 0.05 U Gul6PI, and 0.05 U Gul6PP is incubated at 50° C. for 24 hours. The reaction is stopped via filtration of enzyme with a Vivaspin 2 concentrator (10,000 MWCO). Gulose is verified via HPLC as described in Example 79.

Example 81

A reaction mixture containing 200 g/L maltodextrin, 10 mM acetate buffer (pH 5.5), 5 mM MgCl$_2$, and 0.1 g/L isoamylase is incubated at 80° C. for 24 hours. This is used to create another reaction mixture containing 20 g/L iso-amylase treated maltodextrin, 50 mM phosphate buffered saline pH 7.2, 5 mM MgCl$_2$, 0.05 U of αGP, 0.05 U PGM, 0.05 U PGI, 0.05 U F6PE, 0.05 U S6PE, 0.05 U Gul6PI, and 0.05 U Gul6PP is incubated at 50° C. for 24 hours. Produc-tion of gulose is verified as in Example 79.

Example 82

To further increase gulose yields from maltodextrin, 0.05 U 4-glucan transferase (4GT) is added to the reaction described in Example 80.

A 0.2 mL reaction mixture containing 20 g/L isoamylase treated maltodextrin (see Example 80), 50 mM phosphate buffered saline pH 7.2, 5 mM MgCl$_2$, 0.05 U of αGP, 0.05 U PGM, 0.05 U PGI0.05 U F6PE, 0.05 U S6PE, 0.05 U Gul6PI, 0.05 U Gul6PP, and 0.05 U 4GT is incubated at 50° C. for 24 hours. Production of gulose is verified as in Example 79.

Example 83

To further increase gulose yields from maltodextrin, 0.05 U maltose phosphorylase is added to the reaction described in Example 80.

Example 84

To further increase gulose yields from maltodextrin, 0.05 U polyphosphate glucokinase and 75 mM polyphosphate is added to the reaction described in Example 80.

Example 85

To produce gulose from fructose, a reaction mixture containing 10 g/L fructose, 50 mM Tris buffer pH 7.0, 75 mM polyphosphate, 5 mM MgCl$_2$, 0.05 U fructose poly-phosphate kinase, 0.05 U F6PE, 0.05 U S6PE, 0.05 U Gul6PI, and 0.05 U Gul6PP is incubated at 50° C. for 24 hours. Production of gulose is quantified as in Example 79.

Example 86

To produce gulose from glucose, a reaction mixture containing 10 g/L glucose, 50 mM Tris buffer pH 7.0, 75 mM polyphosphate, 5 mM MgCl$_2$, 0.05 U glucose poly-phosphate kinase, 0.05 U PGI, 0.05 U F6PE, 0.05 U S6PE, 0.05 U Gul6PI, and 0.05 U Gul6PP is incubated at 50° C. for 24 hours. Production of gulose is quantified as in Example 79.

Example 87

To produce gulose from sucrose, a reaction mixture containing 10 g/L sucrose, 50 mM phosphate buffered saline pH 7.0, 5 mM MgCl$_2$, 0.05 U sucrose phosphorylase, 0.05 PGM, 0.05 U PGI, 0.05 U F6PE, 0.05 U S6PE, 0.05 U Gul6PI, and 0.05 U Gul6PP is incubated at 50° C. for 24 hours. Production of gulose is quantified as in Example 79.

Example 88

To further increase yields of gulose from sucrose, 75 mM polyphosphate and 0.05 polyphosphate fructokinase is added to the reaction mixture in Example 86. Production of gulose is quantified as in Example 79.
Idose

Example 89

To validate idose production from F6P, 10 g/L F6P is mixed with 1 U/mL F6PE, 1 U/mL S6PE, 1 U/mL idose 6-phosphate isomerase (I6PI), and 1 U/mL idose 6-phos-phate phosphatase (I6PP) in 50 mM HEPES buffer (pH 7.2)

containing 5 mM $MgCl_2$. The reaction is incubated for 3 hours at 50° C. Conversion of F6P to idose is seen via HPLC (Agilent 1100 series) using an Agilent Hi-Plex H-column and refractive index detector. The sample and control are run in 5 mM $H_2SO_4$ at 0.6 mL/min and 65° C.

Example 90

To validate production of idose from maltodextrin, a 0.20 mL reaction mixture containing 20 g/L maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U S6PE, 0.05 U I6PI, and 0.05 U I6PP is incubated at 50° C. for 24 hours. The reaction is stopped via filtration of enzyme with a Vivaspin 2 concentrator (10,000 MWCO). Idose is verified via HPLC as described in Example 89.

Example 91

A reaction mixture containing 200 g/L maltodextrin, 10 mM acetate buffer (pH 5.5), 5 mM $MgCl_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, 0.05 U F6PE, 0.05 U S6PE, 0.05 U I6PI, and 0.05 U I6PP is incubated at 50° C. for 24 hours. Production of idose is verified as in Example 89.

Example 92

To further increase idose yields from maltodextrin, 0.05 U 4-glucan transferase (4GT) is added to the reaction described in Example 90.

A 0.2 mL reaction mixture containing 20 g/L isoamylase treated maltodextrin (see Example 90), 50 mM phosphate buffered saline pH 7.2, 5 mM $MgCl_2$, 0.05 U of αGP, 0.05 U PGM, 0.05 U PGI 0.05 U F6PE, 0.05 U S6PE, 0.05 U I6PI, 0.05 U I6PP, and 0.05 U 4GT is incubated at 50° C. for 24 hours. Production of idose is verified as in Example 89.

Example 93

To further increase idose yields from maltodextrin, 0.05 U maltose phosphorylase is added to the reaction described in Example 90.

Example 94

To further increase idose yields from maltodextrin, 0.05 U polyphosphate glucokinase and 75 mM polyphosphate is added to the reaction described in Example 90.

Example 95

To produce idose from fructose, a reaction mixture containing 10 g/L fructose, 50 mM Tris buffer pH 7.0, 75 mM polyphosphate, 5 mM $MgCl_2$, 0.05 U fructose polyphosphate kinase, 0.05 U F6PE, 0.05 U S6PE, 0.05 U I6PI, and 0.05 U I6PP is incubated at 50° C. for 24 hours. Production of idose is quantified as in Example 89.

Example 96

To produce idose from glucose, a reaction mixture containing 10 g/L glucose, 50 mM Tris buffer pH 7.0, 75 mM polyphosphate, 5 mM $MgCl_2$, 0.05 U glucose polyphosphate kinase, 0.05 U PGI, 0.05 U F6PE, 0.05 U S6PE, 0.05 U I6PI, and 0.05 U I6PP is incubated at 50° C. for 24 hours. Production of idose is quantified as in Example 89.

Example 97

To produce idose from sucrose, a reaction mixture containing 10 g/L sucrose, 50 mM phosphate buffered saline pH 7.0, 5 mM $MgCl_2$, 0.05 U sucrose phosphorylase, 0.05 PGM, 0.05 U PGI, 0.05 U F6PE, 0.05 U S6PE, 0.05 U I6PI, and 0.05 U I6PP is incubated at 50° C. for 24 hours. Production of idose is quantified as in Example 89.

Example 98

To further increase yields of idose from sucrose, 75 mM polyphosphate and 0.05 polyphosphate fructokinase is added to the reaction mixture in Example 96. Production of idose is quantified as in Example 89.
Tagatose

Example 99

To validate tagatose production from F6P, 2 g/L F6P was mixed with 1 U/ml fructose 6-phosphate epimerase (F6PE) and 1 U/ml tagatose 6-phosphate phosphatase (T6PP) in 50 mM HEPES buffer (pH 7.2) containing 5 mM MgCl2. The reaction was incubated for 16 hours at 50° C. 100% conversion of F6P to tagatose is seen via HPLC (Agilent 1100 series) using an Agilent Hi-Plex H-column and refractive index detector. The sample was run in 5 mM H2SO4 at 0.6 mL/min.

Example 100

To validate production of tagatose from maltodextrin, a 0.20 mL reaction mixture containing 20 g/L maltodextrin, 50 mM phosphate buffered saline pH 7.2, 5 mM MgCl2, 0.05 U of αGP, 0.05 U PGM, 0.05 U PGI, 0.05 U F6PE, and 0.05 U T6PP was incubated at 50° C. for 24 hours. The reaction was stopped via filtration of enzyme with a Vivaspin 2 concentrator (10,000 MWCO). Tagatose was detected and quantified using an Agilent 1100 series HPLC with refractive index detector and an Agilent Hi-Plex H-column. The mobile phase was 5 mM H2SO4, which ran at 0.6 mL/min. A yield of 9.2 g/L tagatose was obtained. This equates to 92% of the theoretical yield due to limits of maltodextrin degradation without enzymes such as isoamylase or 4-glucan transferase. Standards of various concentrations of tagatose were used to quantify our yield.

Example 101

A reaction mixture containing 200 g/L maltodextrin, 10 mM acetate buffer (pH 5.5), 5 mM MgCl2, and 0.1 g/L isoamylase was incubated at 80° C. for 24 hours. This was used to create another reaction mixture containing 20 g/L isoamylase treated maltodextrin, 50 mM phosphate buffered saline pH 7.2, 5 mM MgCl2, 0.05 U of αGP, 0.05 U PGM, 0.05 U PGI, 0.05 U F6PE, and 0.05 U T6PP was incubated at 50° C. for 24 hours. Production of tagatose was quantified as in Example 99. The yield of tagatose was increased to 16 g/L with the pretreatment of maltodextrin by isoamylase. This equates to 80% of the theoretical yield.

Example 102

To further increase tagatose yields from maltodextrin, 0.05 U 4-glucan transferase (4GT) was added to the reaction described in Example 100.

A 0.2 mL reaction mixture containing 20 g/L isoamylase treated maltodextrin (see example 9), 50 mM phosphate buffered saline pH 7.2, 5 mM MgCl2, 0.05 U of αGP, 0.05 U PGM, 0.05 U PGI, 0.05 U F6PE, 0.05 U T6PP, and 0.05 U 4GT was incubated at 50° C. for 24 hours. Production of tagatose was quantified as in example 9. The yield of tagatose was increased to 17.7 g/L with the addition of 4GT to IA-treated maltodextrin. This equates to 88.5% of the theoretical yield.

Example 103

To investigate scale-up, a 20 mL reaction mixture containing 50 g/L isoamylase treated maltodextrin (see Example 99), 50 mM phosphate buffered saline pH 7.2, 5 mM MgCl2, 10 U of αGP, 10 U PGM, 10 U PGI, 10 U F6PE, and 10 U T6PP was incubated at 50° C. for 24 hours. Production of tagatose was quantified as in example 8. The yield of tagatose was 37.6 g/L at the 20 mL scale and 50 g/L maltodextrin. This equates to 75% of the theoretical yield. These results indicate that scale-up to larger reaction volumes will not result in significant loses of yield.

Example 104

To further increase tagatose yields from maltodextrin, 0.05 U maltose phosphorylase is added to the reaction described in Example 100.

Example 105

To further increase tagatose yields from maltodextrin, 0.05 U polyphosphate glucokinase and 75 mM polyphosphate is added to the reaction described in Example 99.

Example 106

To produce tagatose from fructose, a reaction mixture containing 10 g/L fructose, 50 mM Tris buffer pH 7.0, 75 mM polyphosphate, 5 mM MgCl2, 0.05 U fructose polyphosphate kinase, 0.05 U F6PE, and 0.05 U T6PP is incubated at 50° C. for 24 hours. Production of tagatose is quantified as in Example 100.

Example 107

To produce tagatose from glucose, a reaction mixture containing 10 g/L glucose, 50 mM Tris buffer pH 7.0, 75 mM polyphosphate, 5 mM MgCl2, 0.05 U glucose polyphosphate kinase, 0.05 U PGI, 0.05 U F6PE, and 0.05 U T6PP is incubated at 50° C. for 24 hours. Production of tagatose is quantified as in Example 100.

Example 108

To produce tagatose from sucrose, a reaction mixture containing 10 g/L sucrose, 50 mM phosphate buffered saline pH 7.0, 5 mM MgCl2, 0.05 U sucrose phosphorylase, 0.05 PGM, 0.05 U PGI, 0.05 U F6PE, and 0.05 U T6PP is incubated at 50° C. for 24 hours. Production of tagatose is quantified as in Example 100.

Example 109

To further increase yields of tagatose from sucrose, 75 mM polyphosphate and 0.05 polyphosphate fructokinase is added to the reaction mixture in example 15. Production of tagatose is quantified as in Example 100.
Psicose

Example 110

To validate psicose production from F6P, 2 g/L F6P was mixed with 1 U/ml P6PE and 1 U/ml P6PP in 50 mM HEPES buffer (pH 7.2) containing 5 mM $MgCl_2$ and 80 μM $CoCl_2$. The reaction was incubated for 6 hours at 50° C. 99% conversion of F6P to psicose was seen via HPLC (Agilent 1100 series) using an Agilent Hi-Plex H-column and refractive index detector. The sample was run in 5 mM $H_2SO_4$ at 0.6 mL/min.

Example 111

To validate production of psicose from maltodextrin, a 0.20 mL reaction mixture containing 20 g/L maltodextrin, 50 mM phosphate buffered saline pH 7.2, 5 mM $MgCl_2$, 80 μM $CoCl_2$, 0.05 U of αGP, 0.05 U PGM, 0.05 U PGI, 0.05 U P6PE and 0.05 U P6PP is incubated at 50° C. for 24 hours. The reaction is stopped via filtration of enzyme with a Vivaspin 2 concentrator (10,000 MWCO). Psicose is detected and quantified using an Agilent 1100 series HPLC with refractive index detector and an Agilent Hi-Plex H-column. The mobile phase is 5 mM $H_2SO_4$, which runs at 0.6 mL/min. Standards of various concentrations of psicose are used to quantify our yield.

Example 112

A reaction mixture containing 200 g/L maltodextrin, 10 mM acetate buffer (pH 5.5), 5 mM $MgCl_2$, 80 μM $CoCl_2$, and 0.1 g/L isoamylase is incubated at 80° C. for 24 hours. This is used to create another reaction mixture containing 20 g/L isoamylase treated maltodextrin, 50 mM phosphate buffered saline pH 7.2, 5 mM $MgCl_2$, 0.05 U of αGP, 0.05 U PGM, 0.05 U PGI, 0.05 U P6PE, and 0.05 U P6PP is incubated at 50° C. for 24 hours. Production of psicose is quantified as in Example 111.

Example 113

A reaction mixture containing 200 g/L maltodextrin, 10 mM acetate buffer (pH 4.5), 5 mM $MgCl_2$, and 1:200 dilution of Novozymes D6 pullulanase is incubated at 50° C. for 4 hours. This is used to create another reaction mixture containing 20 g/L pullulanase treated maltodextrin, 50 mM phosphate buffered saline pH 7.2, 5 mM $MgCl_2$, 80 μM $CoCl_2$, 0.05 U of αGP, 0.05 U PGM, 0.05 U PGI, 0.05 U P6PE, and 0.05 U P6PP is incubated at 50° C. for 24 hours. Production of psicose is quantified as in Example 111.

Example 114

To further increase psicose yields from maltodextrin, 0.05 U 4-glucan transferase (4GT) is added to the reaction described in Example 111.

A 0.2 mL reaction mixture containing 20 g/L isoamylase treated maltodextrin (see example 9), 50 mM phosphate buffered saline pH 7.2, 5 mM $MgCl_2$, 80 μM $CoCl_2$, 0.05 U of αGP, 0.05 U PGM, 0.05 U PGI, 0.05 U P6PE, 0.05 U P6PP, and 0.05 U 4GT is incubated at 50° C. for 24 hours. Production of psicose is quantified as in Example 111.

Example 115

To investigate scale-up, a 20 mL reaction mixture containing 50 g/L isoamylase treated maltodextrin (see Example 10), 50 mM phosphate buffered saline pH 7.2, 5 mM $MgCl_2$, 80 μM $CoCl_2$, 10 U of αGP, 10 U PGM, 10 U PGI, 10 U P6PE, and 10 U P6PP is incubated at 50° C. for 24 hours. Production of psicose was quantified as in Example 111.

Example 116

To further increase psicose yields from maltodextrin, 0.05 U maltose phosphorylase is added to the reaction described in Example 110.

Example 117

To further increase psicose yields from maltodextrin, 0.05 U polyphosphate glucokinase and 75 mM polyphosphate is added to the reaction described in Example 111.

Example 118

To produce psicose from fructose, a reaction mixture containing 10 g/L fructose, 50 mM Tris buffer pH 7.0, 75 mM polyphosphate, 5 mM MgCl2, 80 μM $CoCl_2$, 0.05 U fructose polyphosphate kinase, 0.05 U P6PE, and 0.05 U P6PP is incubated at 50° C. for 24 hours. Production of psicose is quantified as in Example 111.

Example 119

To produce psicose from glucose, a reaction mixture containing 10 g/L glucose, 50 mM Tris buffer pH 7.0, 75 mM polyphosphate, 5 mM $MgCl_2$, 80 μM $CoCl_2$, 0.05 U glucose polyphosphate kinase, 0.05 U PGI, 0.05 U P6PE, and 0.05 U P6PP is incubated at 50° C. for 24 hours. Production of psicose is quantified as in Example 111.

Example 120

To produce psicose from sucrose, a reaction mixture containing 10 g/L sucrose, 50 mM phosphate buffered saline pH 7.0, 5 mM MgCl2, 80 μM $CoCl_2$, 0.05 U sucrose phosphorylase, 0.05 PGM, 0.05 U PGI, 0.05 U P6PE, and 0.05 U P6PP is incubated at 50° C. for 24 hours. Production of psicose is quantified as in Example 111.

Example 121

To further increase yields of psicose from sucrose, 75 mM polyphosphate and 0.05 polyphosphate fructokinase is added to the reaction mixture in example 20. Production of psicose is quantified as in Example 111.

The invention includes all embodiments and variations substantially as hereinbefore described and with reference to the examples and figures. Although various embodiments of the invention are disclosed herein, adaptations and modifications may be made within the scope of the invention in accordance with the common general knowledge of those skilled in this art.

The invention claimed is:

1. A process for preparing galactose from a saccharide, the process comprising:

converting fructose 6-phosphate (F6P) to tagatose 6-phosphate (T6P) catalyzed by fructose 6-phosphate epimerase (F6PE);

converting the T6P to galactose 6-phosphate (Gal6P) catalyzed by galactose 6-phosphate isomerase (Gal6PI); and converting the Gal6P to galactose catalyzed by galactose 6-phosphate phosphatase (Gal6PP).

2. The process of claim 1, further comprising a step of converting glucose 6-phosphate (G6P) to the F6P, wherein the step is catalyzed by a phosphoglucoisomerase (PGI) or PGPMI.

3. The process of claim 2, further comprising the step of converting glucose 1-phosphate (G1P) to the G6P, wherein the step is catalyzed by a phosphoglucomutase (PGM).

4. The process of claim 3, further comprising the step of converting a saccharide to the G1P, wherein the step is catalyzed by at least one enzyme, wherein the saccharide is starch, a starch derivative, or sucrose.

5. The process of claim 4, wherein the at least one enzyme in the step of converting a saccharide to the G1P is selected from the group consisting of an alpha-glucan phosphorylase (αGP), a sucrose phosphorylase, and mixtures thereof.

6. The process of claim 4, wherein the saccharide is starch or a derivative thereof selected from the group consisting of amylose, amylopectin, soluble starch, amylodextrin, maltodextrin, maltose, and glucose, and mixtures thereof.

7. The process of claim 6, further comprising the step of converting starch to a starch derivative wherein the starch derivative is prepared by enzymatic hydrolysis of starch or by acid hydrolysis of starch.

8. The process of claim 6, wherein 4-glucan transferase (4GT) is added to the process.

9. The process of claim 4, wherein the starch derivative is prepared by enzymatic hydrolysis of starch catalyzed by isoamylase, pullulanase, alpha-amylase, or a combination thereof.

10. The process of claim 1, wherein the process steps are conducted at a temperature ranging from about 37° C. to about 95° C., at a pH ranging from about 5.0 to about 9.0, and/or for about 0.5 hours to about 48 hours.

11. The process of claim 1, wherein the process steps are conducted in a single bioreactor.

12. The process of claim 1, wherein the process steps are conducted ATP-free, NAD(P)(H)-free, at a phosphate concentration from about 0.1 mM to about 150 mM, the phosphate is recycled, and/or the catalysis by the Gal6PP involves an energetically favorable chemical reaction.

13. The process of claim 1, wherein the Gal6PI comprises an amino acid sequence having at least 25% sequence identity with SEQ ID No: 18 or 19, and wherein the Gal6PI catalyzes the conversion of T6P to Gal6P.

14. The process of claim 13, wherein the Gal6PI contains a heterodimer consisting of subunits with Rossmann-like αβα sandwich folds.

15. The process of claim 1, wherein the Gal6PP comprises an amino acid sequence having at least 25% sequence identity with SEQ ID No: 20, and wherein said Gal6PP catalyzes the conversion of Gal6P to galactose.

16. The process of claim 15, wherein the Gal6PP contains a Rossmanoid fold domain for catalysis, a C2 capping domain, D×D signature in the 1st β-strand of the Rossmanoid fold, a Thr or Ser at the end of the 2nd β-strand of the Rossmanoid fold, and a GDxxxD signature at the end of the 4th β-strand of the Rossmanoid fold.

\* \* \* \* \*

80

SEQUENCE LISTING

```
Sequence total quantity: 21
SEQ ID NO: 1           moltype = AA  length = 149
FEATURE                Location/Qualifiers
source                 1..149
                       mol_type = protein
                       organism = Clostridium thermocellum
SEQUENCE: 1
MKIGIGSDHG GYNLKREIID FLKKREYEVI DFGTYGTDSV DYPDFGLKVA EAVKGGECDR  60
GIVVCGTGVG ISISANKVPG IRAAVCTNSY MARMSREHND ANILALGERV VGLDLALDIV  120
DTWLKAEFQG GRHSARVGKI GEIEEKYSK                                     149

SEQ ID NO: 2           moltype = AA  length = 154
FEATURE                Location/Qualifiers
source                 1..154
                       mol_type = protein
                       organism = Symbiobacterium thermophilum
SEQUENCE: 2
MRIAIGNDHV GTEMKRAIAA HLESLGHEVV NFGTDSTERT DYPIYGERVA RAVAAGEVDC  60
GILICGTGVG ISLAANKVRG IRAVVCSEPY TARLSKQHNN TNILAFGARV VGVDLAKMIV  120
DEWLNASFEG GRHQRRVDMI ADIERREECG PEGC                              154

SEQ ID NO: 3           moltype = AA  length = 217
FEATURE                Location/Qualifiers
source                 1..217
                       mol_type = protein
                       organism = Rubellimicrobium thermophilum
SEQUENCE: 3
MTSRYDAVVF DLDGTLIDTE SLCNAAGVEA CAALGLPVSG EFFESLAGID DRTRVQLIGE  60
HVGTAVDLSA FLAAWDRLCI ERFAQGIPLK PGAIELLEQI AAAGIPLALA TSSRRGPAED  120
KLRMAGLARH FRTVVTFDDV AAPKPAPDAY LLAVDRLGVP PARALAFEDS ETGARAAHAA  180
GLTVVQVPDL HPTQGAHAHH VASSLLEGAA MAGLLPV                           217

SEQ ID NO: 4           moltype = AA  length = 216
FEATURE                Location/Qualifiers
source                 1..216
                       mol_type = protein
                       organism = Thermotoga maritima
SEQUENCE: 4
MEAVIFDMDG VLMDTEPLYF EAYRRVAESY GKPYTEDLHR RIMGVPEREG LPILMEALEI  60
KDSLENFKKR VHEEKKRVFS ELLKENPGVR EALEFVKSKR IKLALATSTP QREALERLRR  120
LDLEKYFDVM VFGDQVKNGK PDPEIYLLVL ERLNVVPEKV VVFEDSKSGV EAAKSAGIER  180
IYGVVHSLND GKALLEAGAV ALVKPEEILN VLKEVL                           216
```

-continued

```
SEQ ID NO: 5                 moltype = AA  length = 218
FEATURE                      Location/Qualifiers
source                       1..218
                             mol_type = protein
                             organism = Thermoanaerobacterium saccharolyticum
SEQUENCE: 5
MFEAVILDMD GVLIDSEPLH IQLEEEIFKE IGADISLEEH ISFVGTTSHY MWEYVKNKCN   60
VSFTVEELVE MDRKRYFDYI SKHDGAVKPI EGVDELVKEL YSREVRLAVA SSSPIDVIEL   120
VVKKLHLNDY FCELVSGDFV KRSKPYPDIF LYAAEKLGVS PERCLVVEDS NKGVLAAKSA   180
GMKVIGFINP NSGDQDISMA DMVIRSFSEL NYEKLQNI                           218

SEQ ID NO: 6                 moltype = AA  length = 220
FEATURE                      Location/Qualifiers
source                       1..220
                             mol_type = protein
                             organism = Streptomyces thermoautotrophicus
SEQUENCE: 6
MPSSSGGLQA VFFDMDGLLV DTEPTWHEVE AEVMAEYGYA WTPEDRLACL GGPMERTCRY   60
MIERCGADIT VEALGATLVE RMALRVREEV AVQPGAKELL SELIEAGVPR ALVSSSFRVL   120
VDAVLDAVGH DLFVVTVAGD EVARAKPHPE PYLTAAARLG VDPARCVVLE DSPPGVAAAE   180
AAGCLVVAVP SVAPLEPAPR RLVVRSLTEL SLDRLRALIA                         220

SEQ ID NO: 7                 moltype = AA  length = 219
FEATURE                      Location/Qualifiers
source                       1..219
                             mol_type = protein
                             organism = Sphaerobacter thermophilus
SEQUENCE: 7
MSQGVRGVVF DLDGLLVESE EYWEQARREF VSRYGGTWGD DAQQAVMGAN TRQWSRYIRE   60
AFDIPLTEEE IAAAVIARMQ ELYHDHLPLL PGAIPAVRAL ADRYPLAVAS SSPPVLIRFV   120
LAEMGVAECF QSVTSSDEVA HGKPAPDVYH LACERLGVAP EQAVAFEDST AGIAAALAAG   180
LRVIAVPNRS YPPDPDVLRR ADLTLPSLEE FDPAVLEQW                          219

SEQ ID NO: 8                 moltype = AA  length = 400
FEATURE                      Location/Qualifiers
source                       1..400
                             mol_type = protein
                             organism = Pseudonocardia thermophila
SEQUENCE: 8
MELLDNPIRP YAWGSRTVLA ELLGHESPSP HPEAEMWLGA HPGDPSRLRS GESLLDALCA   60
DPEGLLGADR ARKWDGKLPF LLKVLAADEP LSLQAHPSLD QARVGFEREE RAGIARDAPE   120
RNYRDPNHKP ELLCALTEFH ALVGFRPPEK TVELLAALAV PELDAYSQLL TAQPDANGLR   180
ALFTTWITLP QSVLDTLVPA LQAGCVRLAA ADGPFKAEAR TVLELSERYP GDAGVLAAVL   240
LNRVTLQPGE AVYLPAGNLH AYLEGAGIEV MASSDNVLRG GLTPKHVDVP ELLRVLDFHA   300
AVPPVLTGTP DGAWLRYDTP FEEFLLRRLE GDPAAGLVAV PDGGPRIVLC TRGAAVLRGR   360
DEQLDLHRGA SAWLGADDTG LTVEAVEQNT QLFLAGDGLD                         400

SEQ ID NO: 9                 moltype = AA  length = 405
FEATURE                      Location/Qualifiers
source                       1..405
                             mol_type = protein
                             organism = Caldithrix abyssi
SEQUENCE: 9
MKLKFVARPY ELINKIQNYS WGTRNEQAFI PRLLNMAVEP DTPYAELWMG THPNAPSEVV   60
VDGRRILLSE FIKQFPQQIL GTRVIERFGV QLPFLFKVLS AAEALSIQAH PNKQQAEVLH   120
QRDPEHYPDD NHKPEIAIAL DELTALVGFR SLKEMDAVLR TPPEILEFTG PLEFTFEGAR   180
HEEQENRQKF RQFYQTLMLK SQTHATEMEA TLNKIEQKLL QKKKRTERDE WFLKLKKKYG   240
ADVGLFSIYL LNLLHLKKGQ GVFLKAGVPH AYLKGNIVEC MANSDNVVRA GLTPKFKDVK   300
TLIEVLTYET GPVEIYEGAQ NAKYVYKTPV DEFSITHVNL DEKSKLRFFL ETVSIMMVVN   360
GKGEIVFNGG RLAIQKGQSI LLPAEIASFE LVSDGSLEIF SAYVP                   405

SEQ ID NO: 10                moltype = AA  length = 453
FEATURE                      Location/Qualifiers
source                       1..453
                             mol_type = protein
                             organism = Myceliophthora thermophila
SEQUENCE: 10
MQVPLIRLQC GANSYEWGKK GSSSAVARFA AATPSSDFTI EDDRPYAELW MGTHPSNPSK   60
DLSTGRTLLD LVQDNKALLS PSVAARYDNK VPFLFKVLSI NKALSIQAHP NKKLAEELHR   120
KDPKNYPDDN HKPEMAIAIT PFEGLCGFRP LGEIAHFLES VPPLRQLVGD DNAREFAGIV   180
RQNKDNDSKD AVEQNKKALQ KIFGALMSSS EADMAAAAKV LVESAATAGA DFAAGGVAAT   240
SGSTLAELVQ RLHGQFGADY GLFVLFFLNF VTLQPGEALF LRADDIHAYV SGDIIECMAS   300
SDNVVRAGFT PKFKDVDTLV NMLTYSYAPI DEQKMGPSDY PYATLNRTGY SSGSTISFYD   360
PPIEEFSVIR TNLKESGSKA TFDPVDGPSI IICTAGKGKI SVGPTAQEVK EGYVFFVGAS   420
AKCVLESEGS SEDDEFITFK AFCDVEEHRG ASL                                453

SEQ ID NO: 11                moltype = AA  length = 410
FEATURE                      Location/Qualifiers
```

```
source                      1..410
                            mol_type = protein
                            organism = Treponema caldarium
SEQUENCE: 11
MNNKKKPNFY LLKNPIQRYA WGSKHWIQDL LDLSEQDRQG PMAELWMGAH SRSPSIAFTD    60
ETEQPLDKLI QEHPVHFLGD TIAHDFSSLP YLFKILAAAS PLSIQAHPDK QQAEQGFARE   120
AKAGIPLSAE NRNYKDSNHK PEIICAISPF TAMCGFRTQA EIAELLSLLD VTELEQSLVA   180
IQQIDRKEAY RDFLLSLFLL PQQTRERITK HIQAKLPKLE QKHPRYAKEW ELINLFCTLY   240
PGDSAIISPL YLNVLSLNPG EAIFLPAGVL HAYIHGFGVE LMANSDNVLR GGLTPKHIDI   300
KELLNIIRFE SFKPAVLSAQ KTQQGYHIYP SQVREFSLFH VAVTMDKAQQ LMPGTPIILI   360
VLDGCVSIGT EQEKKTLQKG MSVFLPAERE QLILEGSAHI FGATTGEGTR             410

SEQ ID NO: 12                moltype = AA   length = 223
FEATURE                      Location/Qualifiers
source                       1..223
                             mol_type = protein
                             organism = Tepidimonas fonticaldi
SEQUENCE: 12
MTRWRGIRAV LFDLDGTLVD SAPDLGHAAD LMRQRRGLPP LDEAYYRPRA SSGARGMIEA    60
AFGLTPEHPE FEAYRTEYLD TYGQVLTRRT RPFDGVAELI AALDRAQVAW GVVTNKVERF   120
ALPLTAAIPL FATAATVIGG DTTPHPKPHP APLLEAARRL QLPPQACLYV GDDERDIVAG   180
RAAGMPTVAA RYGYLGVAAD VEAWAADAII ESPQALLNFL DLA                     223

SEQ ID NO: 13                moltype = AA   length = 221
FEATURE                      Location/Qualifiers
source                       1..221
                             mol_type = protein
                             organism = Thermomonas hydrothermalis
SEQUENCE: 13
MSARRFPPLV LFDLDGTLLD SAPDMLVTVN RMRAMRGDAP MALDALRPHV SRGARAMIAA    60
SFPALGGEVP AEMVREFLDI YAQVLGQHGA PFDGVVELLA ALEAAGSRWG IVTNKPESLA   120
RQLLPGLGWD ARCAILVGGD SLPERKPHPL PLLHAAGQLG VSCQDCAYVG DDRRDIEAAR   180
AAGMRSVVAL WGYRLPDENP QDWGGDALSP TPQALLDWPL P                       221

SEQ ID NO: 14                moltype = AA   length = 221
FEATURE                      Location/Qualifiers
source                       1..221
                             mol_type = protein
                             organism = Sulfurivirga caldicuralii
SEQUENCE: 14
MREFDCVLFD LDGTLLDTSY DFAWALNTLQ KQESVPLTPY WRIRQTISSG GRAVVKLGFP    60
DADDDATIEAL RERFLALYHE NISVHTDLFP GLEKVLTHLQ EKAVPWGIVT NKPAWLTDKL   120
LGELDLPAQP QTVVSGDTLA VRKPHPEPMW LAAEQCGVAP ERCLYIGDHP RDIEAPRNAG   180
MQSAAALYGF LPLDAEPDSW PADYRYHAPA DILHHMQKVF P                       221

SEQ ID NO: 15                moltype = AA   length = 344
FEATURE                      Location/Qualifiers
source                       1..344
                             mol_type = protein
                             organism = Syntrophothermus lipocalidus
SEQUENCE: 15
MAVEMGPEMM FEFLYNLPAQ FEGCLKMDFS KASGLKKEYA NIVVTGLGGS AIGGDILRCY    60
CQSRLPIPVV VNRDYMLPRF VGPDSLVLAV SYSGNTEETL SAYEDAREKG ASIIAFTTGG   120
KLAEMAALDG NPVITITGGL VPRAATGYLF APLVLVLERL GLVSGASEDV KETVTVLTQL   180
REEIEPGREE DSNRARFIAG QLYQRIPVIW GCSSTSEVAA MRWKGQINEN AKAPAYFNVF   240
PELNHNEIVG FEVPEDLVKK LAVIILRDPD DHGRITKRIE ITKDILQGKV SSVAEVEARG   300
NSFLAKTYSL IYVGDYASVY LAELYGINPT PVQVIDYLKA RMAE                    344

SEQ ID NO: 16                moltype = AA   length = 328
FEATURE                      Location/Qualifiers
source                       1..328
                             mol_type = protein
                             organism = Schleiferia thermophila
SEQUENCE: 16
MLTLIENFPK HLVDAMITAK KASFKQSNRA IKNVIITGLG GSGIGASMVQ DLLSPHAEIP    60
IIVNKDYHLP AFADENTLVI ACSYSGETEE TLAALAEAEE HSCEIAIITS GGTLLQMAKS   120
KNYNYLQMPE GNPPRSMIGY SLVYQLYMLA YYGISRLALD NDIILSSNYL LEFREKIQSQ   180
ARYIAVRLHK KIPAVYACSG FGSLAERFRQ QLNENSKMLA WNGTVPEMNH NELVGWKGGD   240
EHFAAIFIHT PFDDNRNAKR TEISSNIIQN FTSGVFHIHS EGETPLRAFF YLIHITDWIS   300
YYLSELNGVD VMDISAINQL KGELANFN                                      328

SEQ ID NO: 17                moltype = AA   length = 349
FEATURE                      Location/Qualifiers
source                       1..349
                             mol_type = protein
                             organism = Thermodesulfobium narugense
SEQUENCE: 17
MDKNVMNSYV SDIAYHMKDF YKDLTFYKDG KIDLNEIENL IFLGIGGSAI SPKIFTEIMN    60
INKKVYFFST LNGFEALPDP STSFVIAFSY SGNTVETLRS IELIAKDRFR GIGISSGGKI   120
```

-continued

```
VDLCKSLNWQ HIAVPKGRAP RAAMPFTLSI LFKLALSKGW TEYNEDDFWN DIIELSNSKN  180
NFLPEVDFED NVSKRIAYKL ATKKNVIIWG VESISKNIAY RFKSQLEENA KQLSYYSYLP  240
EASHNQIVPI SLVDNKEEYI VLIFRIPQLE SVLVSNIIST VKTFLNSEGI EVLEVFGSGK  300
NHVLAGLDLI YSTDFVSYYL ALLKGIEPEP IEPISRMKVI LNDNLRKAL              349

SEQ ID NO: 18            moltype = AA  length = 141
FEATURE                  Location/Qualifiers
source                   1..141
                         mol_type = protein
                         organism = Lactococcus lactis
SEQUENCE: 18
MAIVVGADLK GTRLKDVVKN FLVEEGFEVI DVTKDGQDFV DVTLAVASEV NKDEQNLGIV  60
IDAYGAGPFM VATKIKGMVA AEVSDERSAY MTRGHNNARM ITVGAEIVGD ELAKNIAKAF  120
VNGKYDGGRH QVRVDMLNKM C                                           141

SEQ ID NO: 19            moltype = AA  length = 312
FEATURE                  Location/Qualifiers
source                   1..312
                         mol_type = protein
                         organism = Lactococcus lactis
SEQUENCE: 19
MRIAIGCDHI VTDVKMAVSE FLKSKGYEVL DFGTYDHVRT HYPIYGKKVG EAVVSGQADL  60
GVCICGTGVG INNAVNKVPG VRSALVRDMT SALYAKEELN ANVIGFGGMI TGGLLMNDII  120
EAFIEAEYKP TEENKKLIAK IEHVETHNAH QADEEFFTEF LEKWDRGEYH DMAIVVGADL  180
KGTRLKDVVK NFLVEEGFEV IDVTKDGQDF VDVTLAVASE VNKDEQNLGI VIDAYGAGPF  240
MVATKIKGMV AAEVSDERSA YMTRGHNNAR MITVGAEIVG DELAKNIAKA FVNGKYDGGR  300
HQVRVDMLNK MC                                                     312

SEQ ID NO: 20            moltype = AA  length = 270
FEATURE                  Location/Qualifiers
source                   1..270
                         mol_type = protein
                         organism = Bacteroides thetaiotaomicron
SEQUENCE: 20
MKYKLIVLDL DGTLTNSKKE ISSRNRETLI RIQEQGIRLV LASGRPTYGI VPLANELRMN  60
EFGGFILSYN GGEIINWESK EMMYENVLPN EVVPVLYECA RTNHLSILTY DGAEIVTENS  120
LDPYVQKEAF LNKMAIRETN DFLTDITLPV AKCLIVGDAG KLIPVESELC IRLQGKINVF  180
RSEPYFLELV PQGIDKALSL SVLLENIGMT REEVIAIGDG YNDLSMIKFA GMGVAMGNAQ  240
EPVKKAADYI TLTNDEDGVA EAIERIFNVP                                  270

SEQ ID NO: 21            moltype = AA  length = 217
FEATURE                  Location/Qualifiers
source                   1..217
                         mol_type = protein
                         organism = Halothermothrix orenii
SEQUENCE: 21
MIEAVIFDMD GVIINSEPIH YKVNQIIYEK LGIKVPRSEY NTFIGKSNTD IWSFLKRKYN  60
LKESVSSLIE KQISGNIKYL KSHEVNPIPG VKPLLDELSE KQITTGLASS SPEIYIETVL  120
EELGLKSYFK VTVSGETVAR GKPEPDIFEK AARILGVEPP HCVVIEDSKN GVNAAKAAGM  180
ICIGYRNEES GDQDLSAADV VVDSLEKVNY QFIKDLI                          217
```